United States Patent
Buechler

(10) Patent No.: US 11,198,911 B2
(45) Date of Patent: Dec. 14, 2021

(54) SYSTEMS AND METHODS FOR ASSESSING COLORECTAL CANCER MOLECULAR SUBTYPE AND RISK OF RECURRENCE AND FOR DETERMINING AND ADMINISTERING TREATMENT PROTOCOLS BASED THEREON

(71) Applicant: University of Notre Dame Du Lac, South Bend, IN (US)

(72) Inventor: Steven Buechler, Granger, IN (US)

(73) Assignee: UNIVERSITY OF NOTRE DAME DU LAC, South Bend, IN (US)

( * ) Notice: Subject to any disclaimer, the term of this patent is extended or adjusted under 35 U.S.C. 154(b) by 0 days.

(21) Appl. No.: 16/978,903

(22) PCT Filed: Mar. 7, 2019

(86) PCT No.: PCT/US2019/021234
§ 371 (c)(1),
(2) Date: Dec. 4, 2020

(87) PCT Pub. No.: WO2019/173644
PCT Pub. Date: Sep. 12, 2019

(65) Prior Publication Data
US 2021/0082540 A1    Mar. 18, 2021

Related U.S. Application Data

(60) Provisional application No. 62/640,157, filed on Mar. 8, 2018.

(51) Int. Cl.
*C12Q 1/6886* (2018.01)
*G16H 50/20* (2018.01)
*G16H 20/40* (2018.01)
*G16H 70/60* (2018.01)
*G16H 10/40* (2018.01)
*G16B 25/10* (2019.01)
*G16B 40/00* (2019.01)
*G16B 30/00* (2019.01)

(52) U.S. Cl.
CPC .......... *C12Q 1/6886* (2013.01); *G16B 25/10* (2019.02); *G16B 30/00* (2019.02); *G16B 40/00* (2019.02); *G16H 10/40* (2018.01); *G16H 20/40* (2018.01); *G16H 50/20* (2018.01); *G16H 70/60* (2018.01); *C12Q 2600/112* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 2006/0195269 | A1 | 8/2006 | Yeatman et al. |
| 2009/0311269 | A1 | 12/2009 | Allen et al. |
| 2010/0190173 | A1 | 7/2010 | Cowens et al. |
| 2010/0292094 | A1 | 11/2010 | Lapointe et al. |
| 2011/0190143 | A1 | 8/2011 | La Garanderie et al. |
| 2020/0407803 | A1* | 12/2020 | Buechler ................ G16H 20/40 |

FOREIGN PATENT DOCUMENTS

| WO | 2017182656 A1 | 10/2017 |
| WO | 2019173647 A1 | 9/2019 |

OTHER PUBLICATIONS

Linnekamp et al. Consensus Molecular Subtypes of Colorectal Can Are Recapitulated in In Vitro and In Vivo Models' Cell Death & Differentiation, Jan. 5, 2018: vol. 25, No. 3, pp. 616-633; abtract; p. 631, col. 2, second paragraph, https://doi.org/10.1038/s41418-017-0011-5.

Buechler, et al. ColoType: a forty gene signature for consensus molecular subtyping of colorectal cancer tumors using whole-genome assay or targeted RNA-sequencing, Scientific Reports, 2020, 10:12123.

Guinney, et al. The consensus molecular subtypes of colorectal cancer, Nature Medicine, vol. 1, No. 11, Nov. 2015, pp. 1350-1363.

Alderdice, M. et al. Prospective patient stratification into robust cancer-cell intrinsic subtypes from colorectal cancer biopsies. The Journal of Pathology 245, 19-28 (2018).

Van Cutsem, E. et al. Randomized Phase III Trial Comparing Biweekly Infusional Fluorouracil/Leucovorin Alone or With Irinotecan in the Adjuvant Treatment of Stage III Colon Cancer: PETACC-3. J. Clin. Oncol. 27, 3117-3125 (2009).

Dienstmann, R. et al. Relative contribution of clinicopathological variables, genomic markers, transcriptomic subtyping and microenvironment features for outcome prediction in stage II/III colorectal cancer. Ann. Oncol. 30, 1622-1629 (2019).

Yang, M. et al. Repurposing EGFR Inhibitor Utility in Colorectal Cancer in Mutant APC and TP53 Subpopulations. Cancer Epidemiol Biomarkers Prev 28, 1141-1152 (2019).

Sinn, B. V. et al. SETER/PR: a robust 18-gene predictor for sensitivity to endocrine therapy for metastatic breast cancer, npj. Breast Cancer 5, (2019).

Uttam, S. et al. Spatial domain analysis predicts risk of colorectal cancer recurrence and infers associated tumor microenvironment networks. Nat Commun 11, 3515 (2020).

Gallén, M., Gallego, R. & Bellmunt, J. Stage II disease, elderly patients, secondary neoplasms, and the MOSAIC trial. J. Clin. Oncol. 31(12) 1609 (2013).

(Continued)

*Primary Examiner* — Channing S Mahatan
(74) *Attorney, Agent, or Firm* — Denise L. Mayfield; Dykema Gossett PLLC

(57) ABSTRACT

Products, systems, and methods for classifying human colorectal cancer into a consensus molecular subtype (CMS) and for assessing risk of recurrence based on CMS scores and based on risk scores derived from abbreviated gene expression profiles, for determining suitable treatment protocols for human colorectal cancer patients based on the determined CMS classification and based on the determined risk of recurrence, and for administering the suitable treatment protocols.

18 Claims, 8 Drawing Sheets

(56) References Cited

OTHER PUBLICATIONS

Wang, G. et al. Strategies to target energy metabolism in consensus molecular subtype 3 along with Kirsten rat sarcoma viral oncogene homolog mutations for colorectal cancer therapy. J. Cell. Physiol. 234, 5601-5612 (2019).

Schlicker, A. et al. Subtypes of primary colorectal tumors correlate with response to targeted treatment in colorectal cell lines. BMC Med Genomics 5, 66 (2012).

Guinney, J. et al. The consensus molecular subtypes of colorectal cancer. Nat. Med. 21, 1350-1356 (2015).

Taleb, J. et al. The Evolving Biomarker Landscape for Treatment Selection in Metastatic Colorectal Cancer. Drugs 79, 1375-1394 (2019).

Lam, M. et al. The potential role of platelets in the consensus molecular subtypes of colorectal cancer. Cancer Metastasis Rev. 36, 273-288 (2017).

Mooi, J. K. et al. The prognostic impact of consensus molecular subtypes (CMS) and its predictive effects for bevacizumab benefit in metastatic colorectal cancer: molecular analysis of the AGITG MAX clinical trial. Ann. Oncol. 29, 2240-2246 (2018).

Liao, Y., Smyth, G. K. & Shi, W. The R package Rsubread is easier, faster, cheaper and better for alignment and quantification of RNA sequencing reads. Nucleic Acids Res. 47, e47 (2019).

Allen, W. L., Dunne, P. D., McDade, S. & Scanlon, E. Transcriptional subtyping and CD8 immunohistochemistry identifies patients with stage II and III colorectal cancer with poor prognosis who benefit from adjuvant. JCO Precis Oncol PO.17.00241 (2018).

Kamal, Y., Schmit, S. L., Hoehn, H. J., Amos, C. I. & Frost, H. R. Transcriptomic Differences between Primary Colorectal Adenocarcinomas and Distant Metastases Reveal Metastatic Colorectal Cancer Subtypes. Cancer Res. 79, 4227-4241 (2019).

Itatani, Y., Kawada, K. & Sakai, Y. Transforming Growth Factor-β Signaling Pathway in Colorectal Cancer and Its Tumor Microenvironment. International Journal of Molecular Sciences 20, 5822 (2019).

Inamori, K. et al. Translational research of VOLTAGE-A: Efficacy predictors of preoperative chemoradiotherapy and consolidation nivolumab in patients with both microsatellite stable and microsatellite instability-high locally advanced rectal cancer. J Clin Oncol 39 (3_supp) 100-100 (2021).

Kamal, Y. et al. Tumor immune infiltration estimated from gene expression profiles predicts colorectal cancer relapse. Oncoimmunology 10, 1862529 (2021).

Trinh, A. et al. Tumour budding is associated with the mesenchymal colon cancer subtype and RAS/RAF mutations: a study of 1320 colorectal cancers with Consensus Molecular Subgroup (CMS) data. Br. J. Cancer 119, 1244-1251 (2018).

Kim, S. R. et al. Tumour sidedness and intrinsic subtypes in patients with stage II/III colon cancer: analysis of NSABP C-07 (NRG Oncology). Br. J. Cancer 118, 629-633 (2018).

International Search Report of PCT/US2019/021234 dated May 8, 2019.

Linnenkamp et al. 'Consensus Molecular Subtypes of Colorectal Cancer Are Recapitulated in In Vitro and In Vivo Models' Cell Death and Differentiation, Jan. 5, 2018; vol. 25, No. 3, pp. 616-633; abstractl p. 631, col. 2, second paragraph.

Guo, Y. et al. Cyclin A2 maintains colon homeostasis and is a prognostic factor in colorectal cancer. J. Clin. Invest. 131, (2021).

Sargent, D. J. et al. Defective Mismatch Repair as a Predictive Marker for Lack of Efficacy of Fluorouracil-Based Adjuvant Therapy in Colon Cancer. J. Clin. Oncol. 28, 3219-3226 (2010).

Anders, S. & Huber, W. Differential expression analysis for sequence count data. Genome Biol 11, R106 (2010).

De Rosa, N. et al. DNA Mismatch Repair Deficiency in Rectal Cancer: Benchmarking Its Impact on Prognosis, Neoadjuvant Response Prediction, and Clinical Cancer Genetics. J. Clin. Oncol. 34, 3039-3046 (2016).

Jongen, J. M. J et al. Downregulation of DNA repair proteins and increased DNA damage in hypoxic colon cancer cells is a therapeutically exploitable vulnerability. Oncotarget 8, 86296-86311 (2017).

Buechler, S. A., Gökmen-Polar, Y. & Badve, S. S. EarlyR: A Robust Gene Expression Signature for Predicting Outcomes of Estrogen Receptor-Positive Breast Cancer. Clin Breast Cancer 19, 17-26.e8 (2019).

Jackstadt, R. et al. Epithelial NOTCH Signaling Rewires the Tumor Microenvironment of Colorectal Cancer to Drive Poor-Prognosis Subtypes and Metastasis. Cancer Cell 36, 319-336.e7 (2019).

Urosevic, J. et al. ERK1/2 Signaling Induces Upregulation of ANGPT2 and CXCR4 to Mediate Liver Metastasis in Colon Cancer. Cancer Res. 80, 4668-4680 (2020).

Smeby, J. et al. Exploratory analyses of consensus molecular subtype-dependent associations of TP53 mutations with immunomodulation and prognosis in colorectal cancer. ESMO Open 4, e000523 (2019).

De Smedt, L. et al. Expression profiling of budding cells in colorectal cancer reveals an EMT-like phenotype and molecular subtype switching. Br. J. Cancer 116, 58-65 (2017).

Liao, Y., Smyth, G. K. & Shi, W. featureCounts: an efficient general purpose program for assigning sequence reads to genomic features. Bioinformatics 30, 923-930 (2014).

Dutton, L. R. et al. Fibroblast-derived Gremlin1 localises to epithelial cells at the base of the intestinal crypt. Oncotarget 10, 4630-4639 (2019).

McCall, M. N., Bolstad, B. M. & Irizarry, R. A. Frozen robust multiarray analysis (fRMA). Biostatistics 11(2) 242-53 (2010).

Marisa, L. et al. Gene expression classification of colon cancer into molecular subtypes: characterization, validation, and prognostic value. PLoS Med. 10, e1001453 (2013).

Budinska, E. et al. Gene expression patterns unveil a new level of molecular heterogeneity in colorectal cancer. J. Pathol. 231, 63-76 (2013).

Kruger, A. J. et al. H&E image-based consensus molecular subtype classification of colorectal cancer using weak Tabeling. J Clin Oncol 38 (15_supp) e16097 (2020).

Liao, T. T. et al. Harnessing stemness and PD-L1 expression by AT-rich interaction domain-containing protein 3B in colorectal cancer. Theranostics 10, 6095-6112 (2020).

Coto-Llerena, M. et al. High Expression of FAP in Colorectal Cancer Is Associated With Angiogenesis and Immunoregulation Processes. Front Oncol 10, 979 (2020).

Hou, Y. et al. High SEMA4C expression promotes the epithelial-mesenchymal transition and predicts poor prognosis in colorectal carcinoma. Aging (Albany NY) 12, 21992-22018 (2020).

Ubink, I. et al. Histopathological and molecular classification of colorectal cancer and corresponding peritoneal metastases. Br J Surg 105, e204-e211 (2018).

Sirinukunwattana, K. et al. Image-based consensus molecular subtype (imCMS) classification of colorectal cancer using deep learning. Gut 70, 544-554 (2021).

Ubink, I. et al. Imatinib treatment of poor prognosis mesenchymal-type primary colon cancer: a proof-of-concept study in the preoperative window period (ImPACCT). BMC Cancer 17, (2017).

Bae, J. M., Yoo, S. Y., Kim, J. H. & Kang, G. H. Immune landscape and biomarkers for immuno-oncology in colorectal cancers. J Pathol Transl Med 54, 351-360 (2020).

Li, Y. et al. Immunohistochemistry-Based Consensus Molecular Subtypes as a Prognostic and Predictive Biomarker for Adjuvant Chemotherapy in Patients with Stage II Colorectal Cancer. Oncologist 25, e1968-e1979 (2020).

Huyghe, N., Baldin, P. & Van den Eynde, M. Immunotherapy with immune checkpoint inhibitors in colorectal cancer what is the future beyond deficient mismatch-repair tumours. Gastroenterol Rep (Oxf) 8, 11-24 (2020).

Lenz, H. J. et al. Impact of Consensus Molecular Subtype on Survival in Patients With Metastatic Colorectal Cancer: Results From CALGB/SWOG 80405 (Alliance). J. Clin. Oncol. 37, 1876-1885 (2019).

(56) References Cited

OTHER PUBLICATIONS

André, T. et al. Improved Overall Survival With Oxaliplatin, Fluorouracil, and Leucovorin as Adjuvant Treatment in Stage II or III Colon Cancer in the MOSAIC Trial. J. Clin. Oncol. 27, 3109-3116 (2009).
Cremolini, C., Antoniotti, C., Stein, A. & Bendell . . . , J. Individual patient data meta-analysis of FOLFOXIRI plus bevacizumab versus doublets plus bevacizumab as initial therapy of unresectable metastatic colorectal . . . Journal of Clinical Oncol. 38(28) 3314-24 (2020).
Fennell, L. et al. Integrative Genome-Scale DNA Methylation Analysis of a Large and Unselected Cohort Reveals 5 Distinct Subtypes of Colorectal Adenocarcinomas. Cell Mol Gastroenterol Hepatol 8, 269-290 (2019).
Sawayama, H., Miyamoto, Y., Ogawa, K., Yoshida, N. & Baba, H. Investigation of colorectal cancer in accordance with consensus molecular subtype classification. Ann Gastroenterol Surg 4, 528-539 (2020).
Mittempergher, L., Delahaye, L. J. M. J. & Witteveen . . . , A. T. MammaPrint and BluePrint molecular diagnostics using targeted RNA next-generation sequencing technology. The Journal of Molecular Diagnostics 21(5) 808-23 (2019).
Scrucca, L., Fop, M., Murphy, T. B. & Raftery, A. E. mclust 5: clustering, classification and density estimation using Gaussian finite mixture models. The R journal 8(1) 289-317 (2016).
Kandimalla, R. et al. Methylation of WNT target genes AXIN2 and DKK1 as robust biomarkers for recurrence prediction in stage II colon cancer. Oncogenesis 6, e308 (2017).
Fraley, C. & Raftery, A. E. Model-Based Clustering, Discriminant Analysis, and Density Estimation. Journal of the American Statistical Association 97, 611-631 (2002).
Loree, J. M. et al. Molecular Landscape of ERBB2/ERBB3 Mutated Colorectal Cancer. J. Natl. Cancer Inst. 110, 1409-1417 (2018).
Martini, G. et al. Molecular subtypes and the evolution of treatment management in metastatic colorectal cancer. Therapeutic Advances in Medical Oncology 12, 175883592093608 (2020).
Currey, N., Jahan, Z., Caldon, C. E. & Tran . . . , P. N. Mouse model of mutated in colorectal cancer gene deletion reveals novel pathways in inflammation and cancer. Cellular and molecular Gastroenterol Hepatol 7(4) 819-839 (2019).
Sveen, A. et al. Multilevel genomics of colorectal cancers with microsatellite instability-clinical impact of JAK1 mutations and consensus molecular subtype 1. Genome Med 9, 46 (2017).
Sanz-Pamplona, R., Gil-Hoyos, R. & López-Doriga . . . , A. Mutanome and expression of immune response genes in microsatellite stable colon cancer. Oncotarget 7(14) 17711-25 (2016).
Van den Bulk, J. et al. Neoantigen-specific immunity in low mutation burden colorectal cancers of the consensus molecular subtype 4. Genome Med 11,87 (2019).
Colloca, G. A., Venturino, A. & Guarneri, D. Neutrophil-related Variables Have Different Prognostic Effect Based on Primary Tumor Location in Patients With Metastatic Colorectal Cancer Receiving Chemotherapy. Clin Colorectal Cancer 18, e343-e348 (2019).
O'Cathail, S. M. et al. NRF2 metagene signature is a novel prognostic biomarker in colorectal cancer. Cancer Genet 248-249, 1-10 (2020).
Yothers, G. et al. Oxaliplatin as Adjuvant Therapy for Colon Cancer: Updated Results of NSABP C-07 Trial, Including Survival and Subset Analyses. J. Clin. Oncol. 29, 3768-3774 (2011).
Kuebler, J. P. et al. Oxaliplatin Combined With Weekly Bolus Fluorouracil and Leucovorin as Surgical Adjuvant Chemotherapy for Stage II and III Colon Cancer: Results From NSABP C-07. J. Clin. Oncol. 25, 2198-2204 (2007).
André, T., Shiu, K. K., Kim, T. W. & Jensen . . . , B. V. Pembrolizumab in microsatellite-instability-high advanced colorectal cancer. N Engl J Med 383(23)2207-18 (2020).
Sachs, M. C. plotROC: a tool for plotting ROC curves. Journal of statistical software 79(2) (2017).
De Sousa E Melo, F. et al. Poor-prognosis colon cancer is defined by a molecularly distinct subtype and develops from serrated precursor lesions. Nat. Med. 19, 614-618 (2013).
Trinh, A. et al. Practical and Robust Identification of Molecular Subtypes in Colorectal Cancer by Immunohistochemistry. Clin Cancer Res 23, 387-398 (2017).
Kwon, Y. et al. Prognosis of stage III colorectal carcinomas with FOLFOX adjuvant chemotherapy can be predicted by molecular subtype. Oncotarget 8, 39367-39381 (2017).
Khan, M. et al. Prognostic Implications of Mucinous Differentiation in Metastatic Colorectal Carcinoma Can Be Explained by Distinct Molecular and Clinicopathologic Characteristics. Clin Colorectal Cancer 17, e699-e709 (2018).
Sadanandam, A. et al. A colorectal cancer classification system that associates cellular phenotype and responses to therapy. Nat. Med. 19, 619-625 (2013).
Ubink, I. et al. A Novel Diagnostic Tool for Selecting Patients With Mesenchymal-Type Colon Cancer Reveals Intratumor Subtype Heterogeneity. J. Natl. Cancer Inst. 109, (2017).
Gelfo, V et al. A Novel Role for the lnterleukin-1 Receptor Axis in Resistance to Anti-EGFR Therapy. Cancers (Basel) 10, (2018).
Ubink, I., Verhaar, E. R., Kranenburg, O. & Goldschmeding, R. A potential role for CCN2/CTGF in aggressive colorectal cancer. J. Cell Commun. Signal. 10, 223-227 (2016).
Francescangeli, F. et al. A pre-existing population of ZEB2+ quiescent cells with stemness and mesenchymal features dictate chemoresistance in colorectal cancer. J Exp Clin Cancer Res 39, 2 (2020).
Le, C. T. A solution for the most basic optimization problem associated with an ROC curve. Statistical methods in medical research 6, 571:84(2006).
Koch, U. & Radtke, F. A third Notch in colorectal cancer progression and metastasis. J. Exp. Med. 217, (2020).
Shinto, E. et al. A Validation Study for Recurrence Risk Stratification of Stage II Colon Cancer Using the 55-Gene Classifier. Oncology 98, 534-541 (2020).
Johnson, W. E., Li, C. & Rabinovic, A. Adjusting batch effects in microarray expression data using empirical Bayes methods. Biostatistics 8(1), 118:27(2007).
QUASAR Group, Q. C. Adjuvant chemotherapy versus observation in patients with colorectal cancer: a randomised study. The Lancet 370(9604):2020-9 (2007).
Tournigand, C., André, T. & Bonnetain . . . , F. Adjuvant therapy with fluorouracil and oxaliplatin in stage II and elderly patients (between ages 70 and 75 years) with colon cancer: subgroup analyses of the . . . J Clin Oncol 30(27):3353-60 (2012).
Varga, J. et al. AKT-dependent NOTCH3 activation drives tumor progression in a model of mesenchymal colorectal cancer. J. Exp. Med. 217, (2020).
Yuki, S., Gamoh, M., Denda, T., Takashima, A. & Takahashi . . . , S. Analysis of consensus molecular subtypes (CMS) classification in the TRICOLORE trial: A randomized phase III trial of S-1 and irinotecan (IRI) plus bevacizumab . . . J Clin Oncol 38(4_supp) 169-169 (2020).
Conroy, J. M., Pabla, S., Glenn, S. T. & Burgher . . . , B. Analytical validation of a next-generation sequencing assay to monitor immune responses in solid tumors. The Journal of Molecular 20(1) 95-109 (2018).
Ragulan, C. et al. Analytical Validation of Multiplex Biomarker Assay to Stratify Colorectal Cancer into Molecular Subtypes. Sci Rep 9, 7665 (2019).
Cherradi, S. et al. Antibody targeting of claudin-1 as a potential colorectal cancer therapy. J Exp Clin Cancer Res 36, 89 (2017).
Mehrvarz Sarshekeh, A. et al. Association of SMAD4 mutation with patient demographics, tumor characteristics, and clinical outcomes in colorectal cancer. PLoS One 12, e0173345 (2017).
Sarshekeh, A. M., Katkhuda, R. & Verma . . . , A. Association of TGF-β expression with intratumoral infiltration of cytotoxic T lymphocytes in patients with microsatellite-stable colorectal cancer. J Clin Oncol 37(15 suppl) 3577-3577 (2019).
Menter, D. G. et al. Back to the Colorectal Cancer Consensus Molecular Subtype Future. Curr Gastroenterol Rep 21, 5 (2019).

(56) References Cited

OTHER PUBLICATIONS

Kuhn, M. Building predictive models in R using the caret package. J Stat Softw 28(5) (2008).

Schmoll, H. J. et al. Capecitabine Plus Oxaliplatin Compared With Fluorouracil/Folinic Acid as Adjuvant Therapy for Stage III Colon Cancer: Final Results of the NO16968 Randomized Controlled Phase III Trial. J. Clin. Oncol. 33, 3733-3740 (2015).

Pilati, C. et al. CDX2 prognostic value in stage II/III resected colon cancer is related to CMS classification. Ann. Oncol. 28, 1032-1035(2017).

Cybulska, M. et al. Challenges in Stratifying the Molecular Variability of Patient-Derived Colon Tumor Xenografts. Biomed Res Int 2018, 2954208 (2018).

Dunne, P. D. et al. Challenging the Cancer Molecular Stratification Dogma: Intratumoral Heterogeneity Undermines Consensus Molecular Subtypes and Potential Diagnostic Value in Colorectal Cancer. Clinical Cancer Research 22, 4095-4104 (2016).

Loree, J. M. et al. Classifying Colorectal Cancer by Tumor Location Rather than Sidedness Highlights a Continuum in Mutation Profiles and Consensus Molecular Subtypes. Clin Cancer Res 24, 1062-1072 (2018).

Willauer, A. N. et al. Clinical and molecular characterization of early-onset colorectal cancer. Cancer 125, 2002-2010 (2019).

Fischer, J. et al. Clinical implications of the genetics of sporadic colorectal cancer. ANZ J Surg 89, 1224-1229 (2019).

Song, N. et al. Clinical Outcome From Oxaliplatin Treatment in Stage II/III Colon Cancer According to Intrinsic Subtypes: Secondary Analysis of NSABP C-07/NRG Oncology Randomized Clinical Trial. JAMA Oncol 2, 1162-1169 (2016).

Marisa, L. et al. Clinical utility of colon cancer molecular subtypes: Validation of two main colorectal molecular classifications on the PETACC-8 phase III trial cohort. J. Clin. Oncol. 35, 3509-3509 (2017).

Kim, H. S. et al. Clinicopathological and biomolecular characteristics of stage IIB/IIC and stage IIIA colon cancer Insight into the survival paradox. J. Surg. Oncol. 120, 423-430 (2019).

Szeto, C. et al. CMS subtypes characterized by high TMB shows immunosuppressive microenvironment that implies resistance to immunotherapy. J Clin Oncol 37(4_supp) 610-610 (2019).

Eide, P. W., Bruun, J., Lothe, R. A. & Sveen, A. CMScaller: an R package for consensus molecular subtyping of colorectal cancer pre-clinical models. Sci Rep 7, 16618 (2017).

Laurent-Puig, P., Marisa, L., Ayadi, M. & Blum, Y. Colon cancer molecular subtype intratumoral heterogeneity and its prognostic impact: An extensive molecular analysis of the PETACC-8. Annals of Oncology 29(supp 8) (2018).

Cannon, E. & Buechler, S. Colon Cancer Tumor Location Defined by Gene Expression May Disagree With Anatomic Tumor Location. Clinical Colorectal Cancer 18, 149-158 (2019).

Saunders, A. S., Bender, D. E., Ray, A. L., Wu, X. & Morris, K. T. Colony-stimulating factor 3 signaling in colon and rectal cancers: Immune response and CMS classification in TCGA data. PLoS One 16, e0247233 (2021).

Sveen, A. et al. Colorectal Cancer Consensus Molecular Subtypes Translated to Preclinical Models Uncover Potentially Targetable Cancer Cell Dependencies. Clinical Cancer Research 24, 794-806 (2018).

Roepman, P. et al. Colorectal cancer intrinsic subtypes predict chemotherapy benefit, deficient mismatch repair and epithelial-to-mesenchymal transition. Int. J. Cancer 134, 552-562 (2014).

Fessler, E. & Medema, J. P. Colorectal Cancer Subtypes: Developmental Origin and Microenvironmental Regulation. Trends in Cancer 2, 505-518 (2016).

Chang, K. et al. Colorectal premalignancy is associated with consensus molecular subtypes 1 and 2. Ann. Oncol. 29, 2061-2067 (2018).

Buechler, S. Comparison of immune activity profiles of microsatellite instable colon tumors to microsatellite stable tumors having high ColoType CMS1-score. J. Clin. Oncol. 39, (suppl 3; abstr 26) (2021).

The Cancer Genome Atlas Network, Comprehensive molecular characterization of human colon and rectal cancer. Nature 487, 330-337 (2012).

Stintzing, S. et al. Consensus molecular subgroups (CMS) of colorectal cancer (CRC) and first-line efficacy of FOLFIRI plus cetuximab or bevacizumab in the FIRE3 (AIO KRK-0306) trial. Ann. Oncol. 30, 1796-1803 (2019).

Mehrvarz Sarshekeh, A. et al. Consensus molecular subtype (CMS) as a novel integral biomarker in colorectal cancer: A phase II trial of bintrafusp alfa in CMS4 metastatic CRC. J Clin Oncol 38 (15_supp) 4084-4084 (2020).

Komor, M. A. et al. Consensus molecular subtype classification of colorectal adenomas. J. Pathol. 246, 266-276 (2018).

Lam, M., Marie, P. K. & Sarshekeh . . . , A. M. Consensus molecular subtypes (CMS) as a marker for treatment and disease biology in metastatic colorectal cancer (CRC). J Clin Oncol 38 (15_supp) 4089-4089 (2020).

Borelli, B., Fontana, E. & Giordano . . . , M. SO-20 Consensus molecular subtypes and CRCAssigner classifications in metastatic colorectal cancer (mCRC): Prognostic and predictive impact in the TRIBE2 study. J Clin Oncol 38 (15_supp) 4016 (2020).

Okita, A., Takahashi, S., Ouchi, K., Inoue, M. & Watanabe . . . , M. Consensus molecular subtypes classification of colorectal cancer as a predictive factor for chemotherapeutic efficacy against metastatic colorectal cancer. Oncotarget 9 (27) 18698-711 (2018).

Korphaisarn, K. et al. Consensus molecular subtypes in colorectal cancer differ by geographic region. J Clin Oncol 38 (15_supp) 4061 (2020).

Miller, S. A., Ghobashi, A. H. & O'Hagan, H. M. Consensus molecular subtyping of colorectal cancers is influenced by goblet cell content. Cancer Genet 254-255, 34-39 (2021).

Wang, H., Cai, X. & Ma, L. Curcumin Modifies Epithelial-Mesenchymal Transition in Colorectal Cancer Through Regulation of miR-200c/EPM5. Cancer Manag Res 12, 9405-9415 (2020).

International Search Report of PCT/US2019/021237, dated Jun. 10, 2019.

European Supplemental Search Report of EP Application No. 20201192.0, dated Apr. 7, 2021.

\* cited by examiner

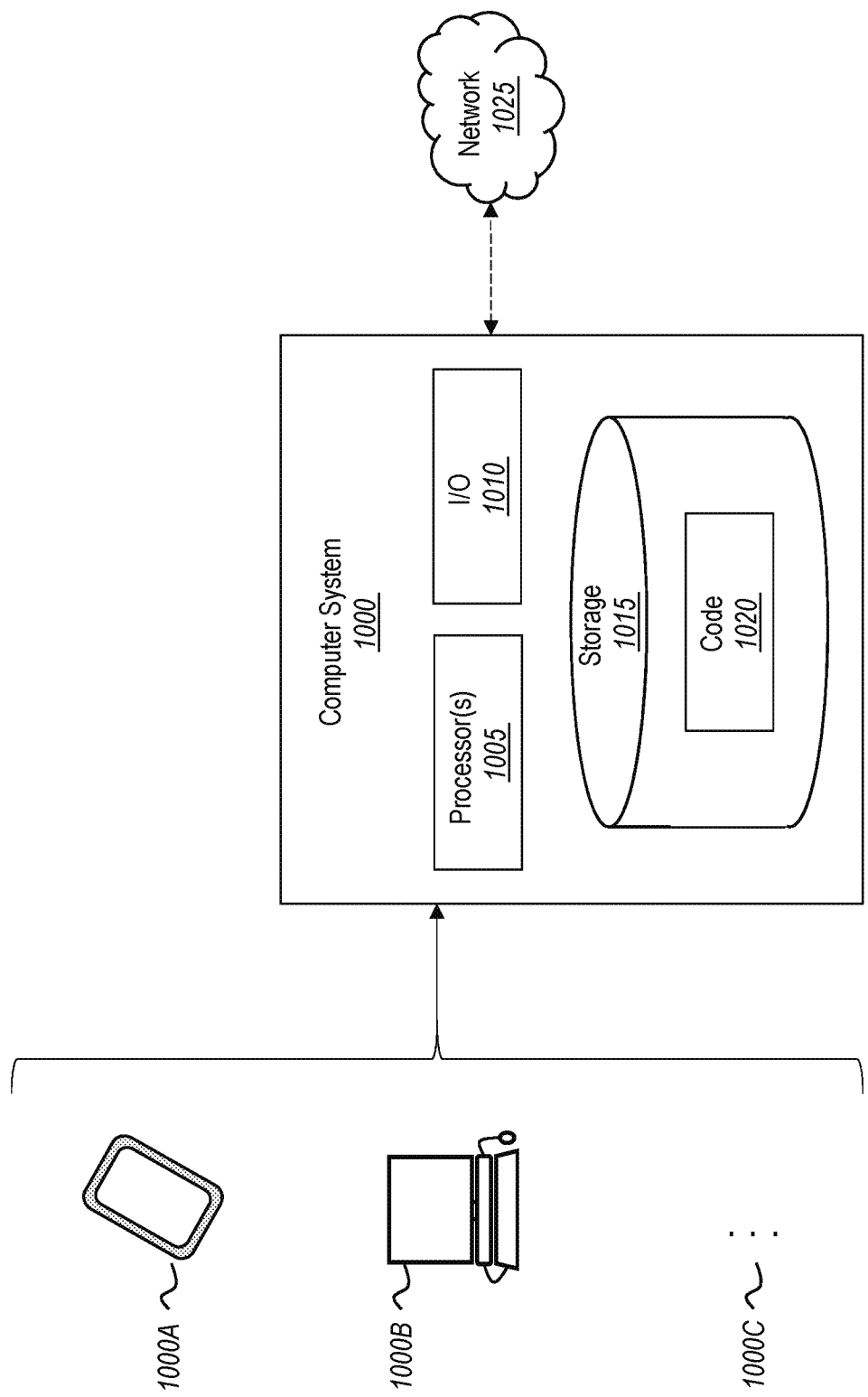

SYSTEMS AND METHODS FOR ASSESSING COLORECTAL CANCER MOLECULAR SUBTYPE AND RISK OF RECURRENCE AND FOR DETERMINING AND ADMINISTERING TREATMENT PROTOCOLS BASED THEREON

CROSS-REFERENCE TO RELATED APPLICATIONS

This application claims the benefit of and priority to U.S. Provisional Patent Application No. 62/640,157, filed on Mar. 8, 2018, entitled "ColortypeR: A Genomic Panel to Predict Molecular Subtype and Risk of Recurrence of a Colorectal Cancer Tumor", the entirety of which is incorporated by reference herein.

BACKGROUND

1. Technical Field

The present disclosure relates to products and methods for determining a molecular subtype and/or risk of recurrence of a colorectal cancer for determining and/or administering a treatment protocol based on the molecular subtype and/or risk of recurrence.

2. The Relevant Technology

Colorectal cancer is the fourth most common type of cancer in the United States and is second only to lung cancer as a cause of cancer-related deaths (see e.g., seer(dot)cancer(dot)gov/statfacts/html/colorect(dot)html). Only 65% of colorectal cancer patients survive for five years after diagnosis. Colon cancer is highly heterogeneous in prognosis and response to treatment. Clinical experience and colon cancer research have led to the understanding that colon cancer is not one disease but occurs as several different subtypes. These subtypes are distinguished by distinct patterns of gene expression that influence or determine tumor biology. Between 2010 and 2014 many papers were published describing methods of classifying colon tumors into molecularly distinct subtypes. Recognizing similarities in many of these subtyping systems, a consortium of experts was formed to derive one subtyping system that inherits the best features from each system. This consortium published the consensus molecular subtypes (CMS) for colon cancer in 2015.

The consensus molecular subtype (CMS) classification system divides colon cancers into 5 district groups, called subtypes, each with distinct biologies and molecular characteristics: CMS1 (MSI Immune), CMS2 (Canonical), CMS3 (Metabolic), CMS4 (Mesenchymal) and Mixed. Publication of this standard classification launched aggressive searches for drugs that are effective in specific CMS subtypes. For example, PD-L1 inhibitors (such as Keytruda®) are likely effective in many CMS1 tumors, but not in CMS4 tumors; and anti-angiogenic agents (such as Avastin®) are likely effective in CMS4 tumors but not CMS1 tumors. The CMS subtype system is very likely to play a major role in colon cancer treatment selection in the near future.

3. Problems in the Art

Clinical trials have shown that various chemotherapeutics benefit some colorectal cancer patients, but not others. To date, no agents have exhibited widespread effectiveness for all types of colorectal cancer. For example, the most widely used form of chemotherapy in colon cancer (fluorouracil and folinic acid) failed to reduce the risk of recurrence for stage II colon cancer in the QUASAR trial (Quasar Collaborative Group et al. 2007). Consequently, the National Comprehensive Cancer Network (NCCN) Guidelines for Colon Cancer (see www(dot)ncn(dot) org/professionals/physician_gls/pdf/colon (dot)pdf) recommends treating stage II colon cancer with observation alone (after surgical removal of tumors); not because expected survival is good—expected survival is only 71% after 5 years—but because no drug seems to be universally beneficial. Conversely, some healthcare providers elect to treat stage II colon cancer with popular or emerging chemotherapeutics as a matter of course, even though the CMS classification and/or risk of recurrence for the cancer might suggest an alternative treatment protocol or course of action.

For colorectal cancer patients, including those at high risk of recurrence and/or those with stage II or stage II colon cancer, not knowing the CMS subtype and/or the risk of recurrence of their cancer may slow or even prevent them from identifying and receiving a life-saving drug. Moreover, subjecting patients with a low risk of relapse to any form of chemotherapy or other treatment would needlessly expose them to the drug's toxic effects. Some stage H colon cancer patients, for example, may have a CMS subtype of cancer for which chemotherapy (e.g., before or after surgical extraction) would be (highly) beneficial, while others would benefit but little from chemotherapy and might needlessly be exposed to the drug's toxic effects. While the NCCN Guidelines for Colon Cancer recommend treating stage II colon cancer with observation alone, this fails to account for the different CMS classifications of the colorectal cancer, which can inform and even determine a more effective and more specific treatment protocol or decision, including if to treat and with what drug(s) to treat. Similarly, CMS classification of the colorectal cancer may help to confirm a decision not to treat and add peace of mind to doctors, patients, and family members. Moreover, a patient with a low recurrence risk colorectal cancers may not benefit significantly from chemotherapy, while patients with high(er) recurrence risk colorectal cancers—even stage II colorectal cancers, for which treatment is not usually recommended—may benefit greatly from treatment.

Although the CMS classification system shows much clinical promise for influencing treatment selection, there are significant hurdles to identifying the CMS subtype of patient's tumor in a normal clinical setting. For example, the methodology and algorithm used by the consortium uses nearly 700 genes to distinguish between the CMS 1-4 subtypes. Assessing the gene expression (or mRNA transcript) levels of these nearly 700 genes is costly, time-consuming, and labor intensive, which complicates adaptation to a clinically applicable diagnostic technology. In particular, the established method for determining a tumor's CMS type requires analysis of tumor tissues using microarray systems, which can be expensive to acquire, operate, maintain, and replace and are typically implemented using a fresh-frozen tumor sample, while standard clinical practice is to preserve tissue in formalin-fixed paraffin-embedded (FFPE) blocks. The authors of the consortium publication admit, however, that their system may not perform well with gene expression measured from FFPE tissue. The use of microarray-based data acquisition platforms for such large numbers of genetic elements can be time-consuming and labor intensive. Similar implementation issues exist for determining a colorectal cancer's risk of recurrence in a clinically-feasible manner.

Accordingly, there are a number of disadvantages in conventional consensus molecular subtype (CMS) determination for colorectal cancer tumors that can be addressed. In particular, there is a critical need for a time- and cost-effective clinical test to determine the consensus molecular subtype, the microsatellite instability, and subtype-specific prognosis for colorectal cancer tumors.

BRIEF SUMMARY

The present disclosure relates to products and methods for determining a molecular subtype and/or risk of recurrence of a colorectal cancer and for determining and/or administering a treatment protocol based on the molecular subtype and/or risk of recurrence. By understanding the CMS subtype and/or risk of recurrence of the cancer, patients and healthcare providers can make informed, cancer treatment-related healthcare decisions based on the biology underlying the patient's cancer. Subtype-specific and/or recurrence risk-related cancer treatments based on these determinations can improve patient outcomes, improve quality of life, reduce treatment delay and/or duration, reduce unnecessary side effects and/or drug toxicity, reduce healthcare costs, and so forth.

While each subtype was originally characterized by hundred(s) of genes expressed in the tumor(s) or cancer cell(s), measuring the expression level of hundreds of genes in a clinical setting in order to elucidate the CMS of a colorectal cancer tumor or tissue sample can be prohibitively expensive, time-consuming, and technically challenging. For instance, the full gene expression profile of a colorectal cancer tissue sample is typically assessed by microarray or RNA sequencing, which are typically executed using a fresh-frozen tumor sample, instead of a formalin-fixed paraffin-embedded (FFPE) blocks according to standard practice.

Technical Solution to Problems in the Art

Embodiments of the present disclosure solve one or more problems in the art with products, systems, and methods for determining the CMS and/or risk of recurrence of a colorectal cancer in a clinically relevant and reasonable manner, so that patients and healthcare providers can determine and/or administer an appropriate colorectal cancer treatment protocol based on the determined CMS and/or risk of recurrence. CMS classification and/or risk of recurrence determined through embodiments of the present disclosure can influence, inform, and/or determine doctor/patient choices with regards to administering treatment protocols. Doctors and patients who might otherwise have elected to treat a colorectal cancer with observation only (following or instead of surgical removal of identified cancer tumors or tissue, for example) may now understand and/or administer a more-effective treatment protocol, which may include treating with chemotherapy and, preferably, a chemotherapy specific for the CMS and/or risk of recurrence of the colorectal cancer, based at least in part on the CMS and/or (high) risk of recurrence of the colorectal cancer. Similarly, doctors and patients who might otherwise have elected to treat colorectal cancer with chemotherapy may now understand and/or administer a more-effective treatment protocol, which may include observation only, based at least in part on the CMS and/or (low) risk of recurrence of the colorectal cancer. Moreover, doctors and patients who might otherwise have elected to treat colorectal cancer with a particular (widely used or generally-accepted) chemotherapy may now understand and/or administer a more-effective treatment protocol, which may include administering a chemotherapy specific for the CMS and/or risk of recurrence of the colorectal cancer, based at least in part on the CMS and/or risk of recurrence of the colorectal cancer.

The CMS of a colorectal cancer is generally defined by the expression of hundreds, if not thousands of genes. In some embodiments of the present disclosure, through mathematical transformation of raw gene expression values into CMS-predictive scores and, where appropriate, application of a CMS classification protocol, the expression level(s) of as few as three highly-predictive genes (per CMS) can serve as a representative or surrogate for the entire CMS-predictive expression profile of the cancer tumor or tissue in order to accurately distinguish between subtypes and determine the CMS of the colorectal cancer based on the CMS scores. In some embodiments, because the expression level of relatively few genes are being assessed, RNA can be extracted from cancer tissue preserved in a FFPE sample block and the expression levels of the suitable and manageable number of genes can be quantified through rapid, inexpensive detection means, such as reverse transcription-polymerase chain reaction (RT-PCR) or RNA sequencing (RNA-seq), instead of microarray based platforms. In similar fashion, through mathematical transformation of raw gene expression values into a recurrence risk score, the expression level(s) of as few as fifteen highly-predictive genes for colorectal cancer recurrence can serve as a representative or surrogate for the entire prognostic recurrence expression profile of the cancer tumor or tissue in order to accurately discern risk of relapse.

Moreover, the use and suitability of the reduced number of highly-predictive genes provides ease, simplicity, efficiency, and cost-effectiveness in showing "analytic validity", a quality control requirement for a commercial diagnostics in various countries, including in the United States. Analytic validity studies the dynamic range, variance and other features of each mRNA species in the diagnostic, and how changes in each gene effects the final test result. Showing analytic validity of a diagnostic test containing or relying on hundred(s) of genes may be difficult, expensive, and time-consuming, or altogether commercially impractical. Thus, embodiments of the present disclosure solve one or more problems in the art by providing an in vitro diagnostic that can be (easily or feasibly) approved by respective government regulatory agencies, such as the U.S. FDA.

Embodiments of the present disclosure also solve one or more problems in the art with products, systems, and methods for determining and reporting the CMS and/or risk or recurrence (or data or information related to the CMS and/or risk or recurrence) of a colorectal cancer in a clinically relevant and reasonable manner, so that patients and healthcare providers can make informed decisions about determining and/or administering an appropriate colorectal cancer treatment protocol based on the determined CMS and/or risk of recurrence. In some embodiments of the present disclosure, a report is generated following analysis of cancer gene expression levels. The report can display, indicate or include value(s) representing the probability of the cancer being of one or more CMS and/or the probability that the cancer will recur in the patient. In some embodiments, the report can display, indicate or include a determination of CMS and/or risk of recurrence. In some embodiments, a CMS report can display, indicate or include a CMS determination, providing the CMS of the colorectal cancer. In some embodiments, the report can display, indicate or include a (recommended or suggested) treatment protocol(s) based at least in part on the CMS determination, or a (recommended or suggested) treatment protocol(s) specific for the CMS of the colorectal cancer. In some embodiments, a risk report can display, indicate or include a probability of recurrence for the colorectal cancer. In some embodiments, a risk report can display, indicate or include a (recommended or suggested) treatment protocol(s) based at least in part on the probability of recurrence for the colorectal cancer.

In one or more embodiments, raw expression data for genes representative of each CMS can be transformed into a comparative and/or continuous CMS score (0-100 or 0-1) representing the (absolute) probability that the analyzed cancer tissue belongs to the respective CMS subtype. Ranking procedures and classification protocol can be used to compare CMS probability scores for each CMS subtype and classify the colorectal cancer into a subtype (CMS1, CMS2, CMS3, CMS4, or mixed/unclassified). Accordingly, some embodiments of the present disclosure include products, systems, and/or methods for using the expression levels of relatively few genes that can recapitulate the gene expression signatures of respective CMS subtypes to generate CMS scores that can be compared in order to assign or classify colorectal cancer into a CMS classification.

Similarly, in some embodiments, raw expression data for genes representative of relapse risk can be transformed into a comparative and/or continuous risk score (0-100 or 0-1) representing the (absolute) probability that the analyzed cancer tissue will return or recur in the patient. Accordingly, some embodiments of the present disclosure include products, systems, and/or methods for using the expression levels of relatively few genes that can recapitulate the gene expression signature of a colorectal cancer recurrence risk profile to generate a risk score that represents colorectal cancer relapse probability and/or predicts relapse.

In a first aspect, the present invention comprises a method of classifying a human colorectal cancer, tumor or tissue into a consensus molecular subtype (CMS).

In a further aspect, the present invention comprises a method of classifying a human colorectal cancer, tumor or tissue into a consensus molecular subtype (CMS) based on the CMS score of an abbreviated gene expression profile.

In a further aspect, the present invention comprises a method of diagnosing a human colorectal cancer, tumor or tissue as belonging to a consensus molecular subtype (CMS).

In a further aspect, the present invention comprises a method of determining a colorectal cancer, tumor or tissue treatment protocol.

In a further aspect, the present invention comprises a method of determining a suitable or recommended colorectal cancer treatment protocol based at least in part on the consensus molecular subtype (CMS) of a colorectal cancer, tumor or tissue.

In a further aspect, the present invention comprises a method of prescribing a suitable colorectal cancer treatment protocol based at least in part on the consensus molecular subtype (CMS) of a colorectal cancer, tumor or tissue.

In a further aspect, the present invention comprises a method of computationally-transforming raw gene expression levels of genes expressed in a colorectal cancer, tumor or tissue sample into one or more consensus molecular subtype (CMS) scores.

In a further aspect, the present invention comprises a method of computationally-transforming raw gene expression levels of genes expressed in a colorectal cancer, tumor or tissue sample into one or more consensus molecular subtype (CMS) scores representative of a probability that the CMS of the colorectal cancer, tumor or tissue is one of CMS1, CMS2, CMS3, CMS4, or mixed subtype.

In a further aspect, the present invention comprises a method of computationally-transforming raw gene expression levels of a clinically-practical number of clinically-relevant genes expressed in a colorectal cancer, tumor or tissue sample into one or more consensus molecular subtype (CMS) scores representative of a probability that the CMS of the colorectal cancer, tumor or tissue is one of CMS1, CMS2, CMS3, CMS4, or mixed subtype.

In a further aspect, the present invention comprises a composition or composition of matter comprising a mixture of cDNA molecules.

In any one or combination of the forgoing aspects, a method, system, kit, or composition according to the present invention can comprise one or more steps, elements, components, or members. It is noted that any of the one or more steps, elements, components, or members of any particular method, system, kit, or composition according to one aspect of the present invention or of the present disclosure is, or may be, applied or applicable to (any) other method(s), system(s), kit(s), or composition(s) according to (any) other aspect(s) of the present invention or of the present disclosure. Moreover, elements, components, or members of any particular system, kit, or composition is, or may be, applied or applicable to (any) method according to (any) other aspect(s) of the present invention or of the present disclosure, and so on and so forth. Thus, the listing, recitation, or disclosure of a particular combination of one or more steps, elements, components, or members of any particular method, system, kit, or composition according to one aspect of the present invention or of the present disclosure is not intended to limit the incorporation or inclusion of said steps, elements, components, or members to only said method, system, kit, or composition.

Listing of exemplary and/or illustrative aspects, embodiments, and/or implementations of the present disclosure and/or invention(s) thereof The following listing provides exemplary and/or illustrative aspects, embodiments, and/or implementations of the present disclosure and/or invention(s) thereof. The listing is provided to disclose and describe certain features of the various exemplary and/or illustrative aspects, embodiments, and/or implementations of the present disclosure and/or invention(s) thereof. Each feature, regardless of how it is presented in the listing, is intended to be disclosed and described independently and not only in the particular combination disclosed herein. Thus, the separation of one or more features from other feature(s) disclosed in connection therewith should not be view or taken as an intermediate generalization of an aspects, embodiments, and/or implementations of the present disclosure and/or invention(s) thereof.

A method of administering a treatment protocol specific for a colorectal cancer to a cancer patient or determining a treatment protocol specific for the colorectal cancer, the method comprising:

obtaining a colorectal cancer tissue sample of unknown consensus molecular subtype (CMS) from a cancer patient;

extracting RNA transcripts from the colorectal cancer tissue sample and quantifying an expression level of at least twelve of the RNA transcripts, the at least twelve RNA transcripts comprising at least three RNA transcripts from each of four groups of genetic elements, each of the four groups of genetic elements defining a CMS gene expression profile specific for a different one of CMS 1, CMS2, CMS3, and CMS4;

determining, based on the expression level of each of the at least three RNA transcripts from a first group of the four groups of genetic elements, a first CMS score representative of a probability that the CMS of the colorectal cancer is CMS1;

determining, based on the expression level of each of the at least three RNA transcripts from a second group of the four groups of genetic elements, a second CMS score representative of a probability that the CMS of the colorectal cancer is CMS2;

determining, based on the expression level of each of the at least three RNA transcripts from a third group of the four groups of genetic elements, a third CMS score representative of a probability that the CMS of the colorectal cancer is CMS3;

determining, based on the expression level of each of the at least three RNA transcripts from a fourth group of the four groups of genetic elements, a fourth CMS score representative of a probability that the CMS of the colorectal cancer is CMS4; and generating a report indicating one or more of:

the first, second, third, and/or fourth CMS scores; and the probability that the CMS of the colorectal cancer is CMS1, CMS2, CMS3, and/or CMS4, wherein one or more of the first, second, third, and/or fourth CMS scores, and the probability that the CMS of the colorectal cancer is CMS1, CMS2, CMS3, and/or CMS4 signifies, at least in part, a treatment protocol specific for the colorectal cancer.

The method, wherein the report is visually displayed on a graphical user interface, the report being generated by a computer system coupled to the graphical user interface, the computer system comprising:

one or more processor(s); and one or more computer-readable hardware storage devices having stored thereon computer-executable instructions that are executable by the one or more processor(s) to cause the computer system to visually display the report.

The method, wherein each step of determining a respective CMS score comprises:

matching the expression level of each RNA transcript from a respective group of genetic elements with a reference expression level of said RNA transcript in a reference data set, each reference expression level corresponding to a scaled value representing the probability that the CMS of a colorectal cancer expressing said RNA transcript at said reference expression level is one of CMS1, CMS2, CMS3, and CMS4; and calculating respective CMS scores based on the respective scaled values for each of the RNA transcripts from the respective group of genetic elements.

The method, wherein the reference data set comprises a curve fit of a population of the respective RNA transcript, the curve fit reflecting the probability that the CMS of a colorectal cancer expressing said RNA transcript at various reference expression levels is one of CMS1, CMS2, CMS3, and CMS4.

The method, wherein calculating the respective CMS scores comprises calculating a mean of the respective scaled values for each of the RNA transcripts from the respective group of genetic elements.

The method, wherein calculating the respective CMS scores comprises:

producing respective CMS pre-scores that inform membership in a respective CMS subtype by ranking risk scores of genes by level of significance in predicting the CMS subtype in the respective reference data set; and selecting at least three of the genes corresponding to at least three of the highest rank genes in the respective reference data set that are also among the highest ranked genes in a second respective reference data set.

The method further comprising administering the treatment protocol specific for the colorectal cancer to the cancer patient.

The method, wherein the treatment protocol specific for the colorectal cancer is further determined by one or more of the stage of the cancer, the grade of the cancer, the metastatic state of the cancer, and the presence or absence of one or more genetic mutations in patient or tissue sample.

The method, wherein the colorectal cancer tissue sample is a formalin-fixed paraffin-embedded (FFPE) colorectal cancer tissue sample and wherein extracting RNA transcripts from the colorectal cancer tissue sample comprises extracting RNA transcripts from the formalin-fixed paraffin-embedded (FFPE) colorectal cancer tissue sample.

The method, wherein quantifying the expression level comprises performing reverse transcription-polymerase chain reaction (RT-PCR).

The method, wherein quantifying the expression level comprises performing RNA sequencing.

The method, wherein each CMS score comprises a number having a scaled value between 0 and 1 or between 0 and 100, or an equivalent thereof.

The method further comprising applying a CMS classification protocol to determine the CMS of the colorectal cancer based on a plurality of CMS score, as follows:

(i) classifying the colorectal cancer with a CMS determination of CMS1 when the first CMS score and the fourth CMS score are each above respective predictive thresholds;

(ii) classifying the colorectal cancer with a CMS determination of CMS4 when the second CMS score and the fourth CMS score are each above respective predictive thresholds and when (i) does not apply;

(iii) selecting from among the first, second, third, and fourth CMS scores a maximal CMS score and classifying the colorectal cancer with a CMS determination selected from the group consisting of CMS1, CMS2, CMS3, and CMS4 based on or corresponding to the maximal CMS score when the maximal CMS score is above the predictive threshold and when neither (i) nor (ii) applies;

(iv) classifying the colorectal cancer with a CMS determination of mixed subtype or unclassified subtype when the first, second, third, and fourth CMS scores are each below the predictive threshold.

The method, wherein the CMS determination indicates, at least in part, a treatment protocol specific for the CMS of the colorectal cancer.

The method, wherein the treatment protocol specific for the CMS of the colorectal cancer is further determined by one or more of the stage of the cancer, the grade of the cancer, the metastatic state of the cancer, and the presence or absence of one or more genetic mutations in patient or tissue sample.

The method further comprising administering the treatment protocol to the cancer patient based at least in part on the CMS determination.

The method, wherein the report indicates one or more of:

the CMS determination;

the CMS of the colorectal cancer;
a treatment protocol based at least in part on the CMS determination; and
a treatment protocol specific for the CMS of the colorectal cancer.
The method, wherein:
the step of determining, based on the expression level of each of the at least five RNA transcripts from a first group of the four groups of genetic elements, a CMS score representative of a probability that the CMS of the colorectal cancer is CMS1, comprises:
(i) matching the expression level of each RNA transcripts from the first group of genetic elements with a corresponding reference expression level of said RNA transcript in a CMS1 reference data set for said RNA transcript, each reference expression level corresponding to a respective scaled value in the respective CMS1 reference data set, each scaled value in the respective CMS1 reference data set representing a probability that the CMS of a colorectal cancer expressing the respective RNA transcript at the respective reference expression level is CMS1; and
(ii) calculating the first CMS score based on the respective scaled values for each of the RNA transcripts from the first group of genetic elements;
the step of determining, based on the expression level of each of the at least five RNA transcripts from a second group of the four groups of genetic elements, a second CMS score representative of a probability that the CMS of the colorectal cancer is CMS2, comprises:
(i) matching the expression level of each RNA transcripts from the second group of genetic elements with a corresponding reference expression level of said RNA transcript in a CMS2 reference data set for said RNA transcript, each reference expression level corresponding to a respective scaled value in the respective CMS2 reference data set, each scaled value in the respective CMS2 reference data set representing a probability that the CMS of a colorectal cancer expressing the respective RNA transcript at the respective reference expression level is CMS2; and
(ii) calculating the second CMS score based on the respective scaled values for each of the RNA transcripts from the second group of genetic elements;
the step of determining, based on the expression level of each of the at least five RNA transcripts from a third group of the four groups of genetic elements, a third CMS score representative of a probability that the CMS of the colorectal cancer is CMS3, comprises:
(i) matching the expression level of each RNA transcripts from the third group of genetic elements with a corresponding reference expression level of said RNA transcript in a CMS3 reference data set for said RNA transcript, each reference expression level corresponding to a respective scaled value in the respective CMS3 reference data set, each scaled value in the respective CMS3 reference data set representing a probability that the CMS of a colorectal cancer expressing the respective RNA transcript at the respective reference expression level is CMS3; and
(ii) calculating the third CMS score based on the respective scaled values for each of the RNA transcripts from the third group of genetic elements; and
the step of determining, based on the expression level of each of the at least five RNA transcripts from a fourth group of the four groups of genetic elements, a fourth CMS score representative of a probability that the CMS of the colorectal cancer is CMS4, comprises:
(i) matching the expression level of each RNA transcripts from the fourth group of genetic elements with a corresponding reference expression level of said RNA transcript in a CMS4 reference data set for said RNA transcript, each reference expression level corresponding to a respective scaled value in the respective CMS4 reference data set, each scaled value in the respective CMS4 reference data set representing a probability that the CMS of a colorectal cancer expressing the respective RNA transcript at the respective reference expression level is CMS4; and
(ii) calculating the fourth CMS score based on the respective scaled values for each of the RNA transcripts from the fourth group of genetic elements;
The method, wherein:
calculating the first CMS score comprises calculating the mean of all the of scaled values for each of the RNA transcripts from the first group of genetic elements;
calculating the second CMS score comprises calculating the mean of all the of scaled values for each of the RNA transcripts from the second group of genetic elements;
calculating the third CMS score comprises calculating the mean of all the of scaled values for each of the RNA transcripts from the third group of genetic elements; and
calculating the fourth CMS score comprises calculating the mean of all the of scaled values for each of the RNA transcripts from the fourth group of genetic elements.
The method, wherein:
calculating the first CMS score further comprises:
producing a first CMS pre-score that informs membership in CMS1 by ranking risk scores of genes by level of significance in predicting membership in CMS1 in the CMS1 reference data set; and
selecting at least three of the genes corresponding to at least three of the highest rank genes in the CMS1 reference data set that are also among the highest ranked genes in a second CMS1 reference data set;
calculating the second CMS score further comprises:
producing a second CMS pre-score that informs membership in CMS2 by ranking risk scores of genes by level of significance in predicting membership in CMS2 in the CMS2 reference data set; and
selecting at least three of the genes corresponding to at least three of the highest rank genes in the CMS2 reference data set that are also among the highest ranked genes in a second CMS2 reference data set;
calculating the third CMS score further comprises:
producing a third CMS pre-score that informs membership in CMS3 by ranking risk scores of genes by level of significance in predicting membership in CMS3 in the CMS3 reference data set; and
selecting at least three of the genes corresponding to at least three of the highest rank genes in the CMS3 reference data set that are also among the highest ranked genes in a second CMS3 reference data set; and
calculating the fourth CMS score further comprises:
producing a fourth CMS pre-score that informs membership in CMS4 by ranking risk scores of genes by level of significance in predicting membership in CMS4 in the CMS4 reference data set; and
selecting at least three of the genes corresponding to at least three of the highest rank genes in the CMS4 reference data set that are also among the highest ranked genes in a second CMS4 reference data set.
The method, wherein the at least twelve RNA transcripts comprise at least sixteen RNA transcripts, the at least sixteen RNA transcripts comprising at least four RNA transcripts from each of the four groups of genetic elements.
The method, wherein the at least twelve RNA transcripts comprise at least twenty RNA transcripts, the at least twenty RNA transcripts comprising at least five RNA transcripts from each of the four groups of genetic elements.

The method, wherein each of the four groups of genetic elements comprises a panel of genes expressed in a population of colorectal cancers having a CMS selected from a different one of CMS1, CMS2, CMS3, and CMS4.

The method, wherein each panel comprises or consists of between five and twenty-five genes expressed in a population of colorectal cancers having a CMS selected from a different one of CMS1, CMS2, CMS3, and CMS4.

The method, wherein:

the first group comprises or consists of the genes represented by or corresponding to ENTREZ IDs 6418, 9219, 10855, 3191, 9037, 10079, 83737, 10140, 8313, 54891, 57798, 998, 7105, 23475, 6431, 3725, 81786, 9554, 1602, 57168, 401474, 139322, 1783, 29966, 80183, 8019, 3549, 27330, and 10451;

the second group comprises or consists of the genes represented by or corresponding to ENTREZ IDs 5326, 112858, 1057, 6780, 23509, 51497, 430, 171023, 25980, 23475, 22919, 80183, 51526, 28951, 1056, 1846, 644, 9054, 55661, 54894, 58490, and 4212;

the third group comprises or consists of the genes represented by or corresponding to ENTREZ IDs 4217, 84666, 8857, 7078, 80150, 4151, 54596, 143458, 84189, 7410, 5937, 25837, 10753, 192134, 201501, 9509, 140828, 84624, 1290, 405753, 1278, 2335, 1295, 3488, 9254, and 155465; and the fourth group comprises or consists of the genes represented by or corresponding to ENTREZ IDs 23414, 30008, 27295, 2737, 143903, 154810, 11037, 7145, 9590, 5178, 23194, 4256, 10000, 1410, 862, 5740, 4286, 83871, 421$_1$, 165, 6695, 1292, 9353, 4131, 8639, 5549, 54796, 147906, and 8828.

The method, wherein:

the at least three RNA transcripts from the first group comprise or consist of RNA transcripts of the genes represented by or corresponding to ENTREZ IDs 9219, 57168, 7105, 23475, and 998;

the at least three RNA transcripts from the second group comprise or consist of RNA transcripts of the genes represented by or corresponding to ENTREZ IDs 112858, 5326, 23509, 6780, and 1846;

the at least three RNA transcripts from the third group comprise or consist of RNA transcripts of the genes represented by or corresponding to ENTREZ IDs 7078, 80150, 84189, 84666, and 5937; and the at least three RNA transcripts from the fourth group comprise or consist of RNA transcripts of the genes represented by or corresponding to ENTREZ IDs 143903, 23414, 11037, 27295, and 165.

A method of accurately determining a consensus molecular subtype of a colorectal cancer from a cancer patient, the method comprising:

obtaining an expression level of at least three colorectal cancer RNA transcripts from a first group of genetic elements, the first group of genetic elements comprising or consisting of the genes represented by or corresponding to ENTREZ IDs 6418, 9219, 10855, 3191, 9037, 10079, 83737, 10140, 8313, 54891, 57798, 998, 7105, 23475, 6431, 3725, 81786, 9554, 1602, 57168, 401474, 139322, 1783, 29966, 80183, 8019, 3549, 27330, and 10451;

obtaining an expression level of at least three colorectal cancer RNA transcripts from a second group of genetic elements, the second group of genetic elements comprising or consisting of the genes represented by or corresponding to ENTREZ IDs 5326, 112858, 1057, 6780, 23509, 51497, 430, 171023, 25980, 23475, 22919, 80183, 51526, 28951, 1056, 1846, 644, 9054, 55661, 54894, 58490, and 4212;

obtaining an expression level of at least three colorectal cancer RNA transcripts from a third group of genetic elements, the third group of genetic elements comprising or consisting of the genes represented by or corresponding to ENTREZ IDs 4217, 84666, 8857, 7078, 80150, 4151, 54596, 143458, 84189, 7410, 5937, 25837, 10753, 192134, 201501, 9509, 140828, 84624, 1290, 405753, 1278, 2335, 1295, 3488, 9254, and 155465;

obtaining an expression level of at least three colorectal cancer RNA transcripts from a fourth group of genetic elements, the fourth group of genetic elements comprising or consisting of the genes represented by or corresponding to ENTREZ IDs 23414, 30008, 27295, 2737, 143903, 154810, 11037, 7145, 9590, 5178, 23194, 4256, 10000, 1410, 862, 4286, 83871, 421$_1$, 165, 6695, 1292, 9353, 4131, 8639, 5549, 54796, 147906, and 8828;

determining, based on the expression level of each of the at least three RNA transcripts from the first group of genetic elements, a first CMS score representative of a probability that the CMS of the colorectal cancer is CMS1;

determining, based on the expression level of each of the at least three RNA transcripts from the second group of genetic elements, a second CMS score representative of a probability that the CMS of the colorectal cancer is CMS2;

determining, based on the expression level of each of the at least three RNA transcripts from the third group of genetic elements, a third CMS score representative of a probability that the CMS of the colorectal cancer is CMS3;

determining, based on the expression level of each of the at least three RNA transcripts from the fourth group of genetic elements, a fourth CMS score representative of a probability that the CMS of the colorectal cancer is CMS4; and generating a report indicating one or more of:

the first, second, third, and/or fourth CMS scores;

the probability that the CMS of the colorectal cancer is CMS1, CMS2, CMS3, and/or CMS4; and a treatment protocol specific for the colorectal cancer, wherein one or more of the first, second, third, and/or fourth CMS scores, and the probability that the CMS of the colorectal cancer is CMS1, CMS2, CMS3, and/or CMS4 indicates, at least in part, the treatment protocol specific for the colorectal cancer.

The method, wherein the report is visually displayed on a graphical user interface, the report being generated by a computer system coupled to the graphical user interface, the computer system comprising:

one or more processor(s); and one or more computer-readable hardware storage devices having stored thereon computer-executable instructions that are executable by the one or more processor(s) to cause the computer system to visually display the report.

The method, wherein each step of determining a respective CMS score comprises:

matching the expression level of each RNA transcript from a respective group of genetic elements with a reference expression level of said RNA transcript in a reference data set, each reference expression level corresponding to a scaled value representing the probability that the CMS of a colorectal cancer expressing said RNA transcript at said reference expression level is one of CMS1, CMS2, CMS3, and CMS4; and calculating respective CMS scores based on the respective scaled values for each of the RNA transcripts from the respective group of genetic elements.

The method, wherein the reference data set comprises a curve fit of a population of the respective RNA transcript, the curve fit reflecting the probability that the CMS of a colorectal cancer expressing said RNA transcript at various reference expression levels is one of CMS1, CMS2, CMS3, and CMS4.

The method, wherein calculating the respective CMS scores comprises calculating a mean of the respective scaled values for each of the RNA transcripts from the respective group of genetic elements.

The method, wherein calculating the respective CMS scores comprises:
producing a first CMS pre-score that informs membership in CMS1 by ranking risk scores of genes by level of significance in predicting membership in CMS1 in the CMS1 reference data set; and
selecting at least three of the genes corresponding to at least three of the highest rank genes in the CMS1 reference data set that are also among the highest ranked genes in a second CMS1 reference data set;
calculating the second CMS score further comprises:
producing a second CMS pre-score that informs membership in CMS2 by ranking risk scores of genes by level of significance in predicting membership in CMS2 in the CMS2 reference data set; and
selecting at least three of the genes corresponding to at least three of the highest rank genes in the CMS2 reference data set that are also among the highest ranked genes in a second CMS2 reference data set;
calculating the third CMS score further comprises:
producing a third CMS pre-score that informs membership in CMS3 by ranking risk scores of genes by level of significance in predicting membership in CMS3 in the CMS3 reference data set; and
selecting at least three of the genes corresponding to at least three of the highest rank genes in the CMS3 reference data set that are also among the highest ranked genes in a second CMS3 reference data set; and
calculating the fourth CMS score further comprises:
producing a fourth CMS pre-score that informs membership in CMS4 by ranking risk scores of genes by level of significance in predicting membership in CMS4 in the CMS4 reference data set; and
selecting at least three of the genes corresponding to at least three of the highest rank genes in the CMS4 reference data set that are also among the highest ranked genes in a second CMS4 reference data set.

The method, further comprising determining a treatment protocol specific for the colorectal cancer and, optionally, administering the treatment protocol specific for the colorectal cancer to the cancer patient, wherein one or more of the first, second, third, and/or fourth CMS scores, and the probability that the CMS of the colorectal cancer is CMS1, CMS2, CMS3, and/or CMS4 indicates, at least in part, the treatment protocol specific for the colorectal cancer.

The method, wherein the treatment protocol specific for the colorectal cancer is further determined by one or more of the stage of the cancer, the grade of the cancer, the metastatic state of the cancer, and the presence or absence of one or more genetic mutations in patient or tissue sample.

The method, wherein each step of obtaining an expression level of at least three RNA transcripts comprises:
optionally extracting RNA transcripts from a colorectal cancer tissue sample from the cancer patient; and
quantifying the expression level of the at least three of the RNA transcripts.

The method, wherein the colorectal cancer tissue sample is a formalin-fixed paraffin-embedded (FFPE) colorectal cancer tissue sample and wherein extracting RNA transcripts from the colorectal cancer tissue sample comprises extracting RNA transcripts from the formalin-fixed paraffin-embedded (FFPE) colorectal cancer tissue sample.

The method, wherein quantifying the expression level comprises performing RNA sequencing and/or reverse transcription-polymerase chain reaction (RT-PCR).

The method, wherein each CMS score comprises a number having a scaled value between 0 and 1 or between 0 and 100, or an equivalent thereof.

The method further comprising applying a CMS classification protocol to determine the CMS of the colorectal cancer based on a plurality of CMS score, as follows:
(v) classifying the colorectal cancer with a CMS determination of CMS1 when the first CMS score and the fourth CMS score are each above respective predictive thresholds;
(vi) classifying the colorectal cancer with a CMS determination of CMS4 when the second CMS score and the fourth CMS score are each above respective predictive thresholds and when (i) does not apply;
(vii) selecting from among the first, second, third, and fourth CMS scores a maximal CMS score and classifying the colorectal cancer with a CMS determination selected from the group consisting of CMS1, CMS2, CMS3, and CMS4 based on or corresponding to the maximal CMS score when the maximal CMS score is above the predictive threshold and when neither (i) nor (ii) applies;
(viii) classifying the colorectal cancer with a CMS determination of mixed subtype or unclassified subtype when the first, second, third, and fourth CMS scores are each below the predictive threshold.

The method, wherein the report further indicates one or more of:
the CMS determination;
the CMS of the colorectal cancer;
a treatment protocol based at least in part on the CMS determination; and
a treatment protocol specific for the CMS of the colorectal cancer.

The method, wherein:
the step of determining the CMS score representative of the probability that the CMS of the colorectal cancer is CMS1, comprises:
(iii) matching the expression level of each RNA transcripts from the first group of genetic elements with a corresponding reference expression level of said RNA transcript in a CMS1 reference data set for said RNA transcript, each reference expression level corresponding to a respective scaled value in the respective CMS1 reference data set, each scaled value in the respective CMS1 reference data set representing a probability that the CMS of a colorectal cancer expressing the respective RNA transcript at the respective reference expression level is CMS1; and
(iv) calculating the first CMS score based on the respective scaled values for each of the RNA transcripts from the first group of genetic elements;
the step of determining the CMS score representative of the probability that the CMS of the colorectal cancer is CMS2, comprises:
(iii) matching the expression level of each RNA transcripts from the second group of genetic elements with a corresponding reference expression level of said RNA transcript in a CMS2 reference data set for said RNA transcript, each reference expression level corresponding to a respective scaled value in the respective CMS2 reference data set, each scaled value in the respective CMS2 reference data set representing a probability that the CMS of a colorectal cancer expressing the respective RNA transcript at the respective reference expression level is CMS2; and (iv) calculating the second CMS score based on the respective scaled values for each of the RNA transcripts from the second group of genetic elements;

the step of determining the CMS score representative of the probability that the CMS of the colorectal cancer is CMS3, comprises:

(iii) matching the expression level of each RNA transcripts from the third group of genetic elements with a corresponding reference expression level of said RNA transcript in a CMS3 reference data set for said RNA transcript, each reference expression level corresponding to a respective scaled value in the respective CMS3 reference data set, each scaled value in the respective CMS3 reference data set representing a probability that the CMS of a colorectal cancer expressing the respective RNA transcript at the respective reference expression level is CMS3; and (iv) calculating the third CMS score based on the respective scaled values for each of the RNA transcripts from the third group of genetic elements; and the step of determining the CMS score representative of the probability that the CMS of the colorectal cancer is CMS4, comprises:

(iii) matching the expression level of each RNA transcripts from the fourth group of genetic elements with a corresponding reference expression level of said RNA transcript in a CMS4 reference data set for said RNA transcript, each reference expression level corresponding to a respective scaled value in the respective CMS4 reference data set, each scaled value in the respective CMS4 reference data set representing a probability that the CMS of a colorectal cancer expressing the respective RNA transcript at the respective reference expression level is CMS4; and (iv) calculating the fourth CMS score based on the respective scaled values for each of the RNA transcripts from the fourth group of genetic elements;

The method, wherein:
calculating the first CMS score comprises calculating the mean of all the of scaled values for each of the RNA transcripts from the first group of genetic elements;
calculating the second CMS score comprises calculating the mean of all the of scaled values for each of the RNA transcripts from the second group of genetic elements;
calculating the third CMS score comprises calculating the mean of all the of scaled values for each of the RNA transcripts from the third group of genetic elements; and
calculating the fourth CMS score comprises calculating the mean of all the of scaled values for each of the RNA transcripts from the fourth group of genetic elements.

The method, wherein:
calculating the first CMS score further comprises:
producing a first CMS pre-score that informs membership in CMS1 by ranking risk scores of genes by level of significance in predicting membership in CMS1 in the CMS1 reference data set; and
selecting at least three of the genes corresponding to at least three of the highest rank genes in the CMS1 reference data set that are also among the highest ranked genes in a second CMS1 reference data set;
calculating the second CMS score further comprises:
producing a second CMS pre-score that informs membership in CMS2 by ranking risk scores of genes by level of significance in predicting membership in CMS2 in the CMS2 reference data set; and selecting at least three of the genes corresponding to at least three of the highest rank genes in the CMS2 reference data set that are also among the highest ranked genes in a second CMS2 reference data set;
calculating the third CMS score further comprises:
producing a third CMS pre-score that informs membership in CMS3 by ranking risk scores of genes by level of significance in predicting membership in CMS3 in the CMS3 reference data set; and
selecting at least three of the genes corresponding to at least three of the highest rank genes in the CMS3 reference data set that are also among the highest ranked genes in a second CMS3 reference data set; and
calculating the fourth CMS score further comprises:
producing a fourth CMS pre-score that informs membership in CMS4 by ranking risk scores of genes by level of significance in predicting membership in CMS4 in the CMS4 reference data set; and
selecting at least three of the genes corresponding to at least three of the highest rank genes in the CMS4 reference data set that are also among the highest ranked genes in a second CMS4 reference data set.

The method, wherein:
the first group comprises or consists of the genes represented by or corresponding to ENTREZ IDs 6418, 9219, 10855, 3191, 9037, 10079, 83737, 10140, 8313, 54891, 57798, 998, 7105, 23475, 6431, 3725, 81786, 9554, 1602, 57168, 401474, 139322, 1783, 29966, 80183, 8019, 3549, 27330, and 10451;
the second group comprises or consists of the genes represented by or corresponding to ENTREZ IDs 5326, 112858, 1057, 6780, 23509, 51497, 430, 171023, 25980, 23475, 22919, 80183, 51526, 28951, 1056, 1846, 644, 9054, 55661, 54894, 58490, and 4212;
the third group comprises or consists of the genes represented by or corresponding to ENTREZ IDs 4217, 84666, 8857, 7078, 80150, 4151, 54596, 143458, 84189, 7410, 5937, 25837, 10753, 192134, 201501, 9509, 140828, 84624, 1290, 405753, 1278, 2335, 1295, 3488, 9254, and 155465; and
the fourth group comprises or consists of the genes represented by or corresponding to ENTREZ IDs 23414, 30008, 27295, 2737, 143903, 154810, 11037, 7145, 9590, 5178, 23194, 4256, 10000, 1410, 862, 4286, 83871, 421$_1$, 165, 6695, 1292, 9353, 4131, 8639, 5549, 54796, 147906, and 8828.

The method, wherein:
the at least three RNA transcripts from the first group comprise or consist of RNA transcripts of the genes represented by or corresponding to ENTREZ IDs 9219, 57168, 7105, 23475, and 998;
the at least three RNA transcripts from the second group comprise or consist of RNA transcripts of the genes represented by or corresponding to ENTREZ IDs 112858, 5326, 23509, 6780, and 1846;
the at least three RNA transcripts from the third group comprise or consist of RNA transcripts of the genes represented by or corresponding to ENTREZ IDs 7078, 80150, 84189, 84666, and 5937; and
the at least three RNA transcripts from the fourth group comprise or consist of RNA transcripts of the genes represented by or corresponding to ENTREZ IDs 143903, 23414, 11037, 27295, and 165

A method of classifying a human colorectal cancer tumor into a consensus molecular subtype (CMS) based on a CMS score derived from an abbreviated gene expression profile, the method comprising:

obtaining an expression level of at least three RNA transcripts from a colorectal cancer tissue sample, the at least three RNA transcripts being selected from a first group of genetic elements that define a first CMS profile for one of CMS1, CMS2, CMS3, and CMS4;

determining, based on the expression level of each of the at least three RNA transcripts from the first group of genetic elements, a first CMS score representative of a probability that the CMS of the colorectal cancer corresponds with the CMS of the first CMS profile; and optionally, classifying the colorectal cancer with a CMS determination corresponding to the CMS of the first CMS profile based at least in part on the first CMS score, wherein the first CMS score is above a predictive threshold.

The method further comprising generating a report indicating one or more of the probability of recurrence for the colorectal cancer and a treatment protocol based at least in part on the probability of recurrence for the colorectal cancer.

The method further comprising:

obtaining an expression level of at least three RNA transcripts selected from a second group of genetic elements that define a second CMS profile for one of CMS1, CMS2, CMS3, and CMS4 that is different from the CMS of the first CMS profile, the at least three RNA transcripts from the second group of genetic elements being from the colorectal cancer tissue sample; and determining, based on the expression level of each of the at least three RNA transcripts from the second group of genetic elements, a second CMS score representative of a probability that the CMS of the colorectal cancer corresponds with the CMS of the second CMS profile.

The method, wherein the step of classifying the colorectal cancer with a CMS determination corresponding to the CMS of the first CMS profile is further based on the second CMS score. The method, wherein the step of classifying the colorectal cancer with a CMS determination corresponding to the CMS of the first CMS profile The method further comprising:

obtaining an expression level of at least three RNA transcripts selected from a third group of genetic elements that define a third CMS profile for one of CMS1, CMS2, CMS3, and CMS4 that is different from the CMS of the first CMS profile and the second CMS profile, the at least three RNA transcripts from the third group of genetic elements being from the colorectal cancer tissue sample; and determining, based on the expression level of each of the at least three RNA transcripts from the third group of genetic elements, a third CMS score representative of a probability that the CMS of the colorectal cancer corresponds with the CMS of the third CMS profile.

The method, wherein the step of classifying the colorectal cancer with a CMS determination corresponding to the CMS of the first CMS profile is further based on the third CMS score.

The method further comprising:

obtaining an expression level of at least three RNA transcripts selected from a fourth group of genetic elements that define a fourth CMS profile for one of CMS1, CMS2, CMS3, and CMS4 that is different from the CMS of the first CMS profile and the second CMS profile and the third CMS profile, the at least three RNA transcripts from the fourth group of genetic elements being from the colorectal cancer tissue sample; and determining, based on the expression level of each of the at least three RNA transcripts from the fourth group of genetic elements, a fourth CMS score representative of a probability that the CMS of the colorectal cancer corresponds with the CMS of the fourth CMS profile.

The method, wherein the step of classifying the colorectal cancer with a CMS determination corresponding to the CMS of the first CMS profile is further based on the fourth CMS score.

The method, wherein:

the at least three RNA transcripts from the first group comprise or consist of RNA transcripts of the genes represented by or corresponding to ENTREZ IDs 9219, 57168, 7105, 23475, and 998;

the at least three RNA transcripts from the second group comprise or consist of RNA transcripts of the genes represented by or corresponding to ENTREZ IDs 112858, 5326, 23509, 6780, and 1846;

the at least three RNA transcripts from the third group comprise or consist of RNA transcripts of the genes represented by or corresponding to ENTREZ IDs 7078, 80150, 84189, 84666, and 5937; and the at least three RNA transcripts from the fourth group comprise or consist of RNA transcripts of the genes represented by or corresponding to ENTREZ IDs 143903, 23414, 11037, 27295, and 165.

The method, wherein the step of obtaining an expression level of at least three RNA transcripts comprises:

extracting RNA transcripts from the colorectal cancer tissue sample; and quantifying the expression level of the at least three of the RNA transcripts.

The method, wherein the CMS determination indicates, at least in part, a suitable treatment protocol specific for the CMS of the colorectal cancer.

The method further comprising administering a treatment protocol to the human patient based at least in part on the CMS determination.

The method further comprising generating a report indicating one or more of the CMS determination, the CMS of the colorectal cancer, a treatment protocol based at least in part on the CMS determination, and a treatment protocol specific for the CMS of the colorectal cancer.

The method, wherein determining a CMS score comprises:

matching the expression level of each RNA transcript with a reference expression level of said RNA transcript in a respective reference data set, each reference expression level corresponding to a scaled value representing the probability that the CMS of a colorectal cancer expressing said RNA transcript at said reference expression level is one of CMS1, CMS2, CMS3, and CMS4; and calculating the CMS score based on the respective scaled values for each of the RNA transcripts.

The method, wherein calculating the CMS score comprises calculating a mean of the respective scaled values for each of the RNA transcripts from the respective group of genetic elements.

The method, wherein each reference data set comprises a curve fit of a population of the respective RNA transcript, the curve fit reflecting the probability that the CMS of a colorectal cancer expressing said RNA transcript at each reference expression level is one of CMS1, CMS2, CMS3, and CMS4.

The method, wherein the first group of genetic elements comprises a panel of genes expressed in a population of colorectal cancers having a CMS selected from CMS1, CMS2, CMS3, and CMS4.

The method, wherein the panel comprises or consists of between five and twenty-five genes expressed in a population of colorectal cancers having a CMS selected from CMS1, CMS2, CMS3, and CMS4.

A method of determining a risk of recurrence for a colorectal cancer in a human patient, the method comprising:
extracting RNA transcripts from a tissue sample of the colorectal cancer;
quantifying an expression level of at least fifteen of the RNA transcripts, the at least fifteen RNA transcripts selected from a group of genetic elements that define a risk of recurrence for the colorectal cancer;
determining, based on the expression level of the at least fifteen RNA transcripts, a risk score representative of a probability of recurrence for the colorectal cancer, and
generating a report indicating one or more of the probability of recurrence for the colorectal cancer and a treatment protocol based at least in part on the probability of recurrence for the colorectal cancer.

The method, wherein each step of determining a risk score comprises:
matching the expression level of each RNA transcript from a respective group of genetic elements with a reference expression level of said RNA transcript in a reference data set, each reference expression level corresponding to a scaled value representing the probability of recurrence for a colorectal cancer expressing said RNA transcript at said reference expression level; and
calculating the risk score based on the respective scaled values for each of the RNA transcripts from the respective group of genetic elements.

The method, wherein the probability of recurrence for the colorectal cancer is substantially independent of consensus molecular subtype (CMS) of the colorectal cancer.

The method, wherein the colorectal cancer is a stage-2 (stage II) or stage-3 (stage III) colon cancer or rectal cancer.

The method, wherein the at least fifteen of the RNA transcripts comprises at least twenty RNA transcripts.

The method, wherein the at least fifteen of the RNA transcripts comprises at least twenty-five RNA transcripts.

The method, wherein the at least fifteen of the RNA transcripts comprises between fifteen and sixty RNA transcripts.

The method, wherein the group of genetic elements comprises a panel of genes expressed in a population of recurring colorectal cancers.

The method, wherein the panel comprises or consists of between fifteen and sixty genes expressed in a population of recurring colorectal cancers.

The method, wherein the group of genetic elements comprises or consists of a subset of genes represented by or corresponding to the following symbols GTSE, TM4SF1, MYADM, RAPGEF6, AHNAK2, PRPF38B, RTN2, BLACAT1, ATP9A, TMEM43, SERPINE1, SMARCC2, ZSCAN18, ARHGEF7, KNL1, SRGAP1, NUP37, SRSF5, CARMN, RARG, ESC02, MPHOSPH9, PAPPA, GUCY1A2, DHRS9, PNRC1, B3GNT7, ARHGEF10, CHEK1, RHBDD1, PSD4, SIN3B, PLXNA3, KCNE4, TM2D1, TRAK1, GGT7, TMEM237, LAMB3, DIS3L2, RABL3, AMACR, ABCC3, ATAD2B, LARP7, SEC23B, FAM3C, NAA25, OBSL1, MUM1, HDAC9, PLXND1, FLT1, CALM1, FN1, KLK8, SREK1, DOCK6, RALGDS, IDI1, TJP2, GABPB1-AS1, DDX1$_1$, ZNF107, SLC35D2, LINC00668, ATF7IP, WDR36, APOL6, DENR, SFXN4, RAF1, AP1G2, SLC26A3, and TMEM144, the group of genetic elements preferably comprising or consisting of genes represented by or corresponding to ENTREZ IDs 51512, 113146, 91663, 4071, 79023, 2335, 5069, 5054, 728264, 6253, 23704, 6430, 51735, 10079, 1111, 55119, 3914, 2977, 101669762, 65062, 10198, 9712, 79188, 84852, and 8874.

The method, wherein the at least fifteen RNA transcripts comprises at least twenty RNA transcripts of genes represented by or corresponding to ENTREZ IDs 51512, 113146, 91663, 4071, 79023, 2335, 5069, 5054, 728264, 6253, 23704, 6430, 51735, 10079, 1111, 551 19, 3914, 2977, 101669762, 65062, 10198, 9712, 79188, 84852, and 8874.

A method of determining a risk of recurrence for a colorectal cancer in a human patient, the method comprising:
obtaining respective expression levels of at least fifteen RNA transcripts, the at least fifteen RNA transcripts selected from a group of genetic elements that define a risk of recurrence for the colorectal cancer, the group of genetic elements comprising or consisting of a subset of genes represented by or corresponding to the following symbols GTSE1, TM4SF1, MYADM, RAPGEF6, AHNAK2, PRPF38B, RTN2, BLACAT1, ATP9A, TMEM43, SERPINE1, SMARCC2, ZSCAN18, ARHGEF7, KNL1, SRGAP1, NUP37, SRSF5, CARMN, RARG, ESC02, MPHOSPH9, PAPPA, GUCY1A2, DHRS9, PNRC1, B3GNT7, ARHGEF10, CHEK1, RHBDD1, PSD4, SIN3B, PLXNA3, KCNE4, TM2D1, TRAK1, GGT7, TMEM237, LAMB3, DIS3L2, RABL3, AMACR, ABCC3, ATAD2B, LARP7, SEC23B, FAM3C, NAA25, OBSL1, MUM1, HDAC9, PLXND1, FLT1, CALM1, FN1, KLK8, SREK1, DOCK6, RALGDS, IDI1, TJP2, GABPB1-AS1, DDX1$_1$, ZNF107, SLC35D2, LINC00668, ATF7P, WDR36, APOL6, DENR, SFXN4, RAF1, AP1G2, SLC26A3, and TMEM144, the group of genetic elements preferably comprising or consisting of genes represented by or corresponding to ENTREZ IDs 51512, 113146, 91663, 4071, 79023, 2335, 5069, 5054, 728264, 6253, 23704, 6430, 51735, 10079, 1111, 551 19, 3914, 2977, 101669762, 65062, 10198, 9712, 79188, 84852, and 8874;
determining, based on the expression level of the at least fifteen RNA transcripts, a risk score representative of a probability of recurrence for the colorectal cancer, and
generating a report indicating one or more of the probability of recurrence for the colorectal cancer and a treatment protocol based at least in part on the probability of recurrence for the colorectal cancer.

The method, wherein the step of determining a risk score comprises:
matching the expression level of each RNA transcript from the group of genetic elements with a reference expression level of said RNA transcript in a reference data set, each reference expression level corresponding to a scaled value representing the probability of recurrence for a colorectal cancer expressing said RNA transcript at said reference expression level; and
calculating the risk score based on the respective scaled values for each of the RNA transcripts from the group of genetic elements.

The method, wherein calculating the risk score comprises calculating a mean of the respective scaled values for each of the RNA transcripts from the group of genetic elements.

The method, wherein the respective reference data set comprises a curve fit of a population of the respective RNA transcript, the curve fit reflecting the probability of recurrence for a colorectal cancer expressing said RNA transcript at said reference expression level.

The method, wherein the probability of recurrence for the colorectal cancer is substantially independent of consensus molecular subtype (CMS) of the colorectal cancer.

D6. The method of claim D, wherein the colorectal cancer is a stage-2 (stage II) or stage-3 (stage III) colon cancer or rectal cancer.

The method, wherein the at least fifteen of the RNA transcripts comprises at least twenty RNA transcripts.

The method, wherein the at least fifteen of the RNA transcripts comprises at least twenty-five RNA transcripts.

The method, wherein the at least fifteen of the RNA transcripts comprises between fifteen and twenty-five RNA transcripts.

The method, wherein the step of obtaining respective expression levels of at least fifteen RNA transcripts comprises (i) optionally extracting the RNA transcripts from a tissue sample of the colorectal cancer and (ii) quantifying the expression level of each RNA transcript.

The method, wherein the colorectal cancer tissue sample is a formalin-fixed paraffin-embedded (FFPE) colorectal cancer tissue sample and wherein extracting RNA transcripts from the colorectal cancer tissue sample comprises extracting RNA transcripts from the formalin-fixed paraffin-embedded (FFPE) colorectal cancer tissue sample.

The method, wherein quantifying the expression level comprises performing RNA sequencing and/or reverse transcription-polymerase chain reaction (RT-PCR).

The method, wherein the risk score comprises a number having a scaled value between 0 and 1 or between 0 and 100, or an equivalent thereof.

The method, wherein the group of genetic elements comprises or consists of genes represented by or corresponding to the following symbols GTSE, TM4SF1, MYADM, RAPGEF6, AHNAK2, PRPF38B, RTN2, BLACAT1, ATP9A, TMEM43, SERPINE1, SMARCC2, ZSCAN18, ARHGEF7, KNL1, SRGAP1, NUP37, SRSF5, CARMN, RARG, ESC02, MPHOSPH9, PAPPA, GUCY1A2, DHRS9, PNRC1, B3GNT7, ARHGEF10, CHEK1, RHBDD1, PSD4, SIN3B, PLXNA3, KCNE4, TM2D1, TRAK, GGT7, TMEM237, LAMB3, DIS3L2, RABL3, AMACR, ABCC3, ATAD2B, LARP7, SEC23B, FAM3C, NAA25, OBSL1, MUM1, HDAC9, PLXND1, FLT1, CALM1, FN1, KLK8, SREK1, DOCK6, RALGDS, IDI1, TJP2, GABPB1-AS1, DDX1 $_1$, ZNF107, SLC35D2, LINC00668, ATF7IP, WDR36, APOL6, DENR, SFXN4, RAF1, AP1G2, SLC26A3, and TMEM144, the group of genetic elements preferably comprising or consisting of genes represented by or corresponding to ENTREZ IDs 51512, 113146, 91663, 4071, 79023, 2335, 5069, 5054, 728264, 6253, 23704, 6430, 51735, 10079, 1111, 551 19, 3914, 2977, 101669762, 65062, 10198, 9712, 79188, 84852, and 8874.

The method, wherein the at least fifteen RNA transcripts comprises at least twenty RNA transcripts of genes represented by or corresponding to ENTREZ IDs 51512, 113146, 91663, 4071, 79023, 2335, 5069, 5054, 728264, 6253, 23704, 6430, 51735, 10079, 1111, 551 19, 3914, 2977, 101669762, 65062, 10198, 9712, 79188, 84852, and 8874.

A system comprising:
one or more processor(s); and
one or more computer-readable hardware storage devices having stored thereon computer-executable instructions that are executable by the one or more processor(s) to cause the computer system to performs one or more of the steps of any preceding claim.

A non-transitory computer-readable storage medium storing instructions that, when executed by one or more processors, performs one or more of the steps of any preceding claim.

A computer system comprising:
one or more processor(s); and
one or more computer-readable hardware storage devices having stored thereon computer-executable instructions that are executable by the one or more processor(s) to cause the computer system to visually display a report by causing the computer system to:

identify expression levels of each of at least twelve RNA transcripts from a colorectal cancer tissue sample of unknown consensus molecular subtype (CMS), the at least twelve RNA transcripts comprising at least three RNA transcripts from each of four groups of genetic elements, each of the four groups of genetic elements defining a CMS gene expression profile specific for a different one of CMS1, CMS2, CMS3, and CMS4;

determine, based on an expression level of each of at least three RNA transcripts from a first group of the four groups of genetic elements, a first CMS score representative of a probability that the CMS of the colorectal cancer is CMS1, the first group of genetic elements comprising or consisting of at least 3 of the genes represented by or corresponding to ENTREZ IDs 6418, 9219, 10855, 3191, 9037, 10079, 83737, 10140, 8313, 54891, 57798, 998, 7105, 23475, 6431, 3725, 81786, 9554, 1602, 57168, 401474, 139322, 1783, 29966, 80183, 8019, 3549, 27330, and 10451;

determine, based on an expression level of each of at least three RNA transcripts from a second group of the four groups of genetic elements, a second CMS score representative of a probability that the CMS of the colorectal cancer is CMS2, the second group of genetic elements comprising or consisting of at least 3 of the genes represented by or corresponding to ENTREZ IDs 5326, 112858, 1057, 6780, 23509, 51497, 430, 171023, 25980, 23475, 22919, 80183, 51526, 28951, 1056, 1846, 644, 9054, 55661, 54894, 58490, and 4212;

determine, based on an expression level of each of at least three RNA transcripts from a third group of the four groups of genetic elements, a third CMS score representative of a probability that the CMS of the colorectal cancer is CMS3, the third group of genetic elements comprising or consisting of at least 3 of the genes represented by or corresponding to ENTREZ IDs 4217, 84666, 8857, 7078, 80150, 4151, 54596, 143458, 84189, 7410, 5937, 25837, 10753, 192134, 201501, 9509, 140828, 84624, 1290, 405753, 1278, 2335, 1295, 3488, 9254, and 155465;

determine, based on an expression level of each of at least three RNA transcripts from a fourth group of the four groups of genetic elements, a fourth CMS score representative of a probability that the CMS of the colorectal cancer is CMS4, the fourth group of genetic elements comprising or consisting of at least 3 of the genes represented by or corresponding to ENTREZ IDs 23414, 30008, 27295, 2737, 143903, 154810, 11037, 7145, 9590, 5178, 23194, 4256, 10000, 1410, 862, 4286, 83871, 421 $_1$, 165, 6695, 1292, 9353, 4131, 8639, 5549, 54796, 147906, and 8828; and generating the report, the report indicating one or more of:
the first, second, third, and/or fourth CMS score;
the probability that the CMS of the colorectal cancer is CMS1, CMS2, CMS3, and/or CMS4; and
a CMS classification or determination for the colorectal cancer;
the CMS of the colorectal cancer;
a treatment protocol based at least in part on the first, second, third, and/or fourth CMS score, the probability that the CMS of the colorectal cancer is CMS1, CMS2, CMS3, and/or CMS4, the CMS classification or determination, and the CMS of the colorectal cancer; and
a treatment protocol specific for the CMS of the colorectal cancer, a treatment protocol specific for the colorectal cancer,
The computer system, wherein the report is visually displayed on a graphical user interface coupled to the computer system.
The computer system, wherein the computer-executable instructions are further executable by the one or more processor(s) to cause the computer system to perform any one or more of the step of any preceding claim.

A computer system comprising:
one or more processor(s); and
one or more computer-readable hardware storage devices having stored thereon computer-executable instructions that are executable by the one or more processor(s) to cause the computer system to visually display a report by causing the computer system to:
identify respective expression levels of at least fifteen RNA transcripts from a colorectal cancer tissue sample, the at least fifteen RNA transcripts selected from a group of genetic elements that define a risk of recurrence for the colorectal cancer, the group of genetic elements comprising or consisting of genes represented by or corresponding to the following symbols GTSE1, TM4SF1, MYADM, RAPGEF6, AHNAK2, PRPF38B, RTN2, BLACAT1, ATP9A, TMEM43, SERPINE1, SMARCC2, ZSCAN18, ARHGEF7, KNL1, SRGAP1, NUP37, SRSF5, CARMN, RARG, ESC02, MPHOSPH9, PAPPA, GUCY1A2, DHRS9, PNRC1, B3GNT7, ARHGEF10, CHEK1, RHBDD1, PSD4, SIN3B, PLXNA3, KCNE4, TM2D1, TRAK1, GGT7, TMEM237, LAMB3, DIS3L2, RABL3, AMACR, ABCC3, ATAD2B, LARP7, SEC23B, FAM3C, NAA25, OBSL1, MUM1, HDAC9, PLXND1, FLT1, CALM1, FN1, KLK8, SREK1, DOCK6, RALGDS, IDI1, TJP2, GABPB1-AS1, DDX1 $_1$, ZNF107, SLC35D2, LINC00668, ATF7IP, WDR36, APOL6, DENR, SFXN4, RAF1, AP1G2, SLC26A3, and TMEM144, the group of genetic elements preferably comprising or consisting of genes represented by or corresponding to ENTREZ IDs 51512, 113146, 91663, 4071, 79023, 2335, 5069, 5054, 728264, 6253, 23704, 6430, 51735, 10079, 1111, 551 19, 3914, 2977, 101669762, 65062, 10198, 9712, 79188, 84852, and 8874;
determine, based on the expression level of the at least fifteen RNA transcripts, a risk score representative of a probability of recurrence for the colorectal cancer, and
generate a report indicating one or more of the probability of recurrence for the colorectal cancer and a treatment protocol based at least in part on the probability of recurrence for the colorectal cancer.
The computer system, wherein the report is visually displayed on a graphical user interface coupled to the computer system.
The computer system, wherein the computer-executable instructions are further executable by the one or more processor(s) to cause the computer system to perform any one or more of the step of any preceding claim.

A composition, comprising a mixture of cDNA molecules corresponding to at least twelve RNA transcripts, the at least twelve RNA transcripts comprising at least three RNA transcripts from each of four groups of genetic elements, each of the four groups of genetic elements defining a CMS gene expression profile specific for a different one of CMS1, CMS2, CMS3, and CMS4, the at least twelve RNA transcripts comprising:
at least three RNA transcripts from a first group of genetic elements, the first group comprising or consisting of the genes represented by or corresponding to ENTREZ IDs 6418, 9219, 10855, 3191, 9037, 10079, 83737, 10140, 8313, 54891, 57798, 998, 7105, 23475, 6431, 3725, 81786, 9554, 1602, 57168, 401474, 139322, 1783, 29966, 80183, 8019, 3549, 27330, and 10451; at least three RNA transcripts from a second group of genetic elements, the second group comprising or consisting of the genes represented by or corresponding to ENTREZ IDs 5326, 112858, 1057, 6780, 23509, 51497, 430, 171023, 25980, 23475, 22919, 80183, 51526, 28951, 1056, 1846, 644, 9054, 55661, 54894, 58490, and 4212;
at least three RNA transcripts from a third group of genetic elements, the third group comprising or consisting of the genes represented by or corresponding to ENTREZ IDs 4217, 84666, 8857, 7078, 80150, 4151, 54596, 143458, 84189, 7410, 5937, 25837, 10753, 192134, 201501, 9509, 140828, 84624, 1290, 405753, 1278, 2335, 1295, 3488, 9254, and 155465; and
at least three RNA transcripts from a fourth group of genetic elements, the fourth group comprising or consisting of the genes represented by or corresponding to ENTREZ IDs 23414, 30008, 27295, 2737, 143903, 154810, 11037, 7145, 9590, 5178, 23194, 4256, 10000, 1410, 862, 4286, 83871, 421 $_1$, 165, 6695, 1292, 9353, 4131, 8639, 5549, 54796, 147906, and 8828.

A composition, comprising a mixture of cDNA molecules corresponding to at least twelve RNA transcripts, the at least twelve RNA transcripts comprising at least three RNA transcripts from each of four groups of genetic elements, each of the four groups of genetic elements defining a CMS gene expression profile specific for a different one of CMS1, CMS2, CMS3, and CMS4, the at least twelve RNA transcripts comprising:
at least three RNA transcripts from a first group of genetic elements, the first group comprising or consisting of the genes represented by or corresponding to ENTREZ IDs 9219, 57168, 7105, 23475, and 998;
at least three RNA transcripts from a second group of genetic elements, the second group comprising or consisting of the genes represented by or corresponding to ENTREZ IDs 112858, 5326, 23509, 6780, and 1846;
at least three RNA transcripts from a third group of genetic elements, the third group comprising or consisting of the genes represented by or corresponding to ENTREZ IDs 7078, 80150, 84189, 84666, and 5937; and
at least three RNA transcripts from a fourth group of genetic elements, the fourth group comprising or consisting of the genes represented by or corresponding to ENTREZ IDs 143903, 23414, 11037, 27295, and 165.

A composition, comprising a mixture of cDNA molecules corresponding to at least fifteen RNA transcripts from a group of genetic elements that define a risk of recurrence for a colorectal cancer, the group of genetic elements comprising or consisting of the genes represented by or corresponding to the following symbols GTSE1, TM4SF1, MYADM, RAPGEF6, AHNAK2, PRPF38B, RTN2, BLACAT1, ATP9A, TMEM43, SERPINE1, SMARCC2, ZSCAN18, ARHGEF7, KNL1, SRGAP1, NUP37, SRSF5, CARMN, RARG, ESC02, MPHOSPH9, PAPPA, GUCY1A2, DHRS9, PNRC1, B3GNT7, ARHGEF10, CHEK1, RHBDD1, PSD4, SIN3B, PLXNA3, KCNE4, TM2D1, TRAK1, GGT7, TMEM237, LAMB3, DIS3L2, RABL3, AMACR, ABCC3, ATAD2B, LARP7, SEC23B, FAM3C, NAA25, OBSL1, MUM1, HDAC9, PLXND1, FLT1, CALM1, FN1, KLK8, SREK1, DOCK6, RALGDS, IDI1, TJP2, GABPB1-AS1, DDX1 $_1$, ZNF107, SLC35D2, LINC00668, ATF7IP, WDR36, APOL6, DENR, SFXN4, RAF1, AP1G2, SLC26A3, and TMEM144.

A composition, comprising a mixture of cDNA molecules corresponding to at least fifteen RNA transcripts from a group of genetic elements that define a risk of recurrence for a colorectal cancer, the group of genetic elements comprising or consisting of the genes represented by or corresponding to ENTREZ IDs 51512, 113146, 91663, 4071, 79023, 2335, 5069, 5054, 728264, 6253, 23704, 6430, 51735, 10079, 1111, 551 19, 3914, 2977, 101669762, 65062, 10198, 9712, 79188, 84852, and 8874.

A method of confirming or modifying a cancer treatment protocol for a patient with colon or rectal cancer, the method comprising:
performing the method of any one of the claims to determine if the colon or rectal cancer is of consensus molecular subtype (CMS) is CMS1, CMS2, CMS3, CMS4, or mixed subtype; and
(i) recommending or administering treatment with a chemotherapeutic when the colon or rectal cancer is CMS4; or
(ii) performing the method of any one of the claims to determine if the probability of recurrence of the colon or rectal cancer is sufficiently high to recommend or administer treatment with the chemotherapeutic when the colon or rectal cancer is CMS1, CMS2, CMS3, or mixed subtype.
The method, wherein the chemotherapeutic is or comprises FOLFOX or FOLFIRI.
The method, wherein the chemotherapeutic is or comprises:
fluorouracil, oxaliplatin, and folinic acid, preferably leucovorin calcium; and/or
fluorouracil, irinotecan, and folinic acid, preferably leucovorin calcium.
The method further comprising:
recommending or administering treatment with the chemotherapeutic when the probability of recurrence is greater than or equal to a predetermined risk threshold; or
recommending or administering an observation protocol when the probability of recurrence is less than a predetermined risk threshold.
The method, wherein the predetermined risk threshold is or comprises a probability of recurrence greater than or equal to about forty-one percent or 0.41 for the colon or rectal cancer.
The method, wherein the colon or rectal cancer is stage IIA or stage IIB colon or rectal cancer.

A method of confirming or modifying a cancer treatment protocol for a patient with colon or rectal cancer, the method comprising:
performing the method of any one of the claims to determine if the colon or rectal cancer is of consensus molecular subtype (CMS) is CMS1, CMS2, CMS3, CMS4, or mixed subtype; and
(i) recommending or administering treatment with a chemotherapeutic when the colon or rectal cancer is CMS2; or
(ii) performing the method of any one of the claims to determine if the probability of recurrence of the colon or rectal cancer is sufficiently high to recommend or administer treatment with the chemotherapeutic when the colon or rectal cancer is CMS1, CMS3, CMS4, or mixed subtype.
The method, wherein the chemotherapeutic is or comprises cetuximab.
The method, wherein the chemotherapeutic is or comprises a monoclonal antibody that inhibits activity of the gene EGFR.
The method further comprising:
recommending or administering treatment with the chemotherapeutic when the probability of recurrence is greater than or equal to a predetermined risk threshold; or
recommending or administering an observation protocol when the probability of recurrence is less than a predetermined risk threshold.

The method, wherein the predetermined risk threshold is or comprises a probability of recurrence greater than or equal to about forty-one percent or 0.41 for the colon or rectal cancer. The method, wherein the colon or rectal cancer is metastatic colon or rectal cancer.

Additional aspects, features, advantages, and exemplary embodiments of the present disclosure will be set forth in the description which follows, and in part will be obvious from the description, or may be learned by the practice thereof. Various aspects, features, and advantages may also be realized and obtained by means of the instruments and combinations particularly pointed out in the specification and appended claims. These and other aspects, features, and advantages will become more fully apparent from the following description and appended claims, or may be learned by the practice of the embodiments set forth hereinafter.

BRIEF DESCRIPTION OF THE DRAWINGS

FIG. 10 illustrates a computer system in accordance with an embodiment or aspect of the present disclosure.

DETAILED DESCRIPTION

Figure 1A:
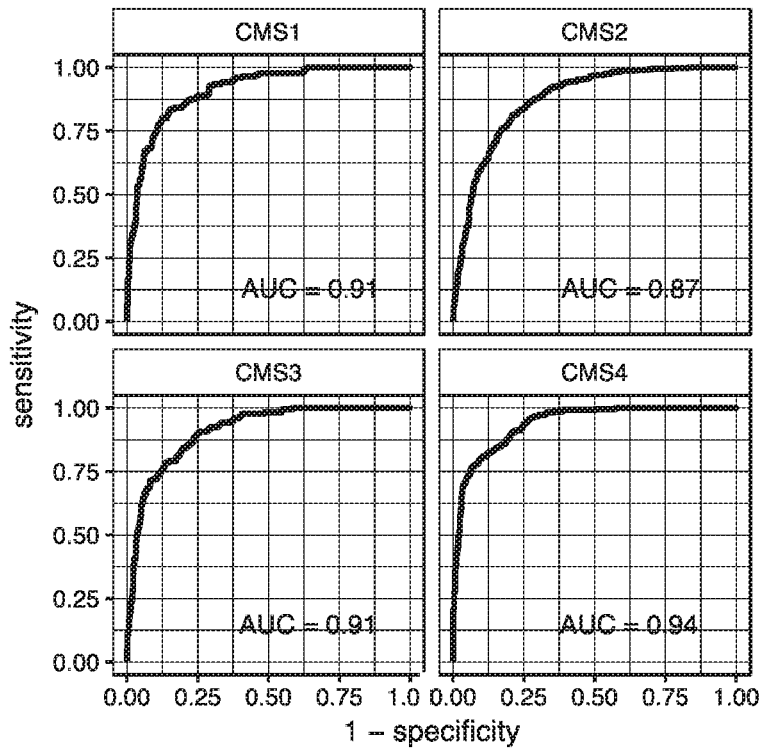
FIGS. 1A-1B illustrate receiver operator characteristic (ROC) curves for (A) Affymetrix validation set, and (B) the COAD validation set, in accordance with an embodiment of the present disclosure.

Before describing various aspects embodiments of the present disclosure in detail, it is to be understood that this disclosure is not limited only to the specific parameters, verbiage, and description of the particularly exemplified systems, methods, and/or products that may vary from one embodiment to the next. Thus, while certain embodiments of the present disclosure will be described in detail, with reference to specific features (e.g., configurations, parameters, properties, steps, components, etc.), the descriptions are illustrative and are not to be construed as limiting the scope of the present disclosure and/or the claimed invention.

In addition, the terminology used herein is for the purpose of describing the embodiments and is not necessarily intended to limit the scope of the present disclosure and/or the claimed invention.

While the detailed description is separated into sections, the section headers and contents within each section are for organizational purposes only and are not intended to be self-contained descriptions and embodiments or to limit the scope of the description or the claims. Rather, the contents of each section within the detailed description are intended to be read and understood as a collective whole, where elements of one section may pertain to and/or inform other sections. Accordingly, embodiments specifically disclosed within one section may also relate to and/or serve as additional and/or alternative embodiments in another section having the same and/or similar products, methods, and/or terminology.

To facilitate understanding, like references (i.e., like naming of features, parameters, components and/or elements) may be used, where possible, to designate like elements common to different embodiments of the present disclosure.

For the sake of brevity, the present disclosure may recite a list or range of numerical values. It will be appreciated, however, that where such a list or range of numerical values (e.g., greater than, less than, up to, at least, and/or about a certain value, and/or between two recited values) is disclosed or recited, any specific value or range of values falling within the disclosed values or list or range of values is likewise specifically disclosed and contemplated herein.

Abbreviated List of Defined Terms

To assist in understanding the scope and content of the foregoing and forthcoming written description and appended claims, a select few terms are defined directly below.

Unless defined otherwise, all technical and scientific terms used herein have the same meaning as commonly understood by one of ordinary skill in the art to which the present disclosure pertains.

Various aspects of the present disclosure, including systems, methods, and/or products may be illustrated with reference to one or more embodiments, which are exemplary in nature. As used herein, the term "embodiment" means "serving as an example, instance, or illustration," and should not necessarily be construed as preferred or advantageous over other aspects disclosed herein. In addition, reference to an "embodiment" of the present disclosure or invention is intended to provide an illustrative example without limiting the scope of the invention, which is indicated by the appended claims.

As used in this specification and the appended claims, the singular forms "a," "an" and "the" each contemplate, include, and specifically disclose both the singular and plural referents, unless the context clearly dictates otherwise. For example, reference to a "protein" contemplates and specifically discloses one, as well as a plurality of (e.g., two or more, three or more, etc.) proteins. Similarly, use of a plural referent does not necessarily require a plurality of such referents, but contemplates, includes, specifically discloses, and/or provides support for a single, as well as a plurality of such referents, unless the context clearly dictates otherwise.

As used throughout this disclosure, the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, the term "product(s)" includes devices, apparatus, assemblies, systems, and so forth. Similarly, the term "method" includes processes, procedures, steps, and so forth.

As used herein, a "feature" or "aspect" of the present disclosure or embodiment disclosed herein refers to a property, attribute, component, element, member, part, portion, (method) step, or other facet of the subject matter at hand.

The word "or" as used herein generally means any one member of a particular list, but also includes any combination of two or more members of said list. Similarly, the term "and" can be interchangeable with the terms "or," either of which can be understood to mean "and/or".

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The terms "comprising", "consisting of", and "consisting essentially of" can be alternatively used. When one of these three terms is used, the presently disclosed and claimed subject matter can include the use of either of the other two terms.

The terms "plurality" and "at least two" are used interchangeably.

The term "patient," as used herein, is synonymous with the term "subject" and generally refers to any animal under the care of a medical professional, as that term is defined herein, with particular reference to (i) humans (under the care of a doctor, nurse, or medical assistant or volunteer) and (ii) non-human animals, such as non-human mammals (under the care of a veterinarian or other veterinary professional, assistant, or volunteer).

The terms "medical professional" as used herein, generally refers to any individual or entity that is responsible for or participates in providing health care to an animal, including human and non-human animals, such as non-human mammals, with particular emphasis on licensed health care providers or unlicensed providers, such as assistants, technicians, and/or volunteers, particularly those covered under the (blanket) license or insurance of a health care provider. This term may, when contextually appropriate, include an oncologist, a surgeon, a physician's assistant, a nurse, a phlebotomist, a veterinarian, etc.

The term "cancer" refers to an abnormal, typically uncontrolled, growth of cells. A "cancerous cell" as used herein comprises a malignant cell having an abnormal, typically uncontrolled, growth. As such, the term cancer is an umbrella term encompassing a plurality of different distinctive diseases characterized by malignant cells growing in a typically uncontrolled manner.

The term "diagnosis," or diagnosing," and similar terms, as used herein, is not intended to convey or require (in all cases) a certified, regulatory-compliant, medical diagnosis, as required or regulated by the U.S. Food and Drug Administration (FDA) or any other government or non-government entity, organization, or agency. Rather, "diagnosis," or diagnosing," and similar terms, as used herein, relates to providing information that may be indicative of a condition and/or helpful in making a determination related to the condition.

All publications, patents, and patent applications cited herein, whether supra or infra, are hereby incorporated by reference in their entirety to the same extent as if each individual publication, patent, or patent application was specifically and individually indicated to be incorporated by reference.

Certain aspects of the present disclosure may be presented using a discovery-validation paradigm, as outlined in further detail, below. Data used during discovery and validation are typically described separate from methodology leading to the discovery. Discovery and validation of CMS and Risk are each covered in separate sections. Tables of summary characteristics of data and genes comprising the panels, along with figures supporting the results and presented in separate subsequent sections.

Various aspects and/or embodiments of the present disclosure comprise or relate to an inventive colorectal cancer classifier (system and/or methodology). The classifier can be effective for identifying the CMS subtype of a colorectal cancer, tumor or tissue or indicating a probability (score) of the colorectal cancer, tumor or tissue being of a particular CMS classification. Given a primary colorectal tumor sample, the CMS classifier uses measurements of a manageable number (e.g., between 3 and about 50) of genes (e.g., by measuring mRNA expression thereof) to derive numerical scores, from which the sample's CMS subtype is predicted or inferred. While the full expression profile of hundreds of CMS classification genes (per CMS subtype) was originally derived using microarray data, the relatively few number of genes and the manner in which mRNA measurements are combined to derive a prediction allow for easy translation adaptation to a clinical test.

CMS classifier is one component or aspect of the inventive diagnostic or classifier, system, tool, and/or methodology. Another (optional) component or aspect includes the inventive Risk classifier. The Risk classifier/methodology, as disclosed herein, comprises and/or relies a genomic score derived from the expression of a manageable number (e.g., between about 15 and about 60) of genes (e.g., by measuring mRNA expression) that estimates a colorectal cancer patient's risk of recurrence. The Risk classifier is significantly prognostic within each CMS subtype and is prognostic independent of CMS classification and/or the CMS classifier methodology, making it universally valid and/or applicable in assessing colorectal cancer.

Thus, using the inventive classifier (system, tool, and/or methodology) a doctor can identify those colorectal cancer patients in need of (aggressive, chemotherapy) treatment, and the most effective drug for each patient. Doctors and patients can make informed healthcare decisions related to cancer treatment in a timely, cost-effective, and clinically-feasible manner. Moreover, treatment decisions can be made quickly, which can save and/or extend a patient's life, especially when the cancer is an aggressive or fast-growing cancer. Low-risk patients can have rapid peace of mind in knowing that chemotherapy will not be administered (e.g., following surgical removal of the cancer. Each of the foregoing provides a meaningful improvement over existing colorectal cancer assessment options.

CMS Classifier Methodology

Certain embodiments of the present disclosure relate to the initial discovery that a data-processed, 20-gene expression signature, comprised of five genes from each of the four CMS categories, can accurately define CMS subtypes for primary colorectal cancer tumor samples. As discussed in further detail herein, however, the expression level of as few as three CMS-predictive genes (per CMS subtype) can be effective in accurately defining CMS subtypes for colorectal cancer.

Patient Cohorts with Whole-Genome Analysis

Various embodiments of the present disclosure were developed and preliminarily validated using genome-wide gene expression data from multiple cohorts. Table 1 presents characteristics of colorectal cancer samples used for training and validation of CMS classification embodiments of the present disclosure in each of three cohorts. A first cohort; Cohort A (n=1888) includes gene expression data from colorectal cancer samples hybridized to Affymetrix hgu13plus2 arrays obtained from Colorectal Cancer Subtyping Consortium (CRCSC, Synapse Project 2623706, see www(dot)synapse(dot)org) comprised of the datasets GSE13067, GSE13294, GSE14333, GSE17536, GSE2109, GSE23878, GSE35896, GSE37892, GSE39582, KFSYCC. Duplicate samples in the GSE14333 and GSE17536 were eliminated. Gene expression values normalized using fRMA were obtained from the Synapse Project 2623706 for all datasets except GSE2109. For GSE2109, the CEL files available on the Synapse archive were normalized using fRMA and batch corrected to the other cohorts using combat.

TABLE 1

| | Cohort A (Affymetrix) | | Cohort B (COAD) | | Cohort C (PETACC3) | |
|---|---|---|---|---|---|---|
| | training (n = 683)* | validation (n = 1205)† | training (n = 189) | validation (n = 193) | training (n = 342) | validation (n = 346) |
| assay platform | Affymetrix hgu133plus2 | Affymetrix hgu133plus2 | RNA-seq | RNA-seq | custom array | custom array |
| stage (1/2/3/4/NA) | 61/293/241/88/0 | 134/206/164/30/612 | 28/65/58/15/7 | 29/62/48/14/2 | NA | NA |
| median age | 68 | 70 | 67 | 69 | NA | NA |
| msi/mss/NA | 72/402/209 | 86/133/653 | 32/133/8 | 28/123/4 | NA | NA |
| CMS§ 1/2/3/4/NONE [n (%)] | 117 (17)/281 (41)/ 81 (12)/141 (21)/ 63 (9) | 133 (15)/315 (36)/ 121 (14)/200 (23)/ 101 (12) | 28 (16)/60 (35)/ 25 (14)/41 (24)/ 19 (11) | 26 (17)/59 (32)/ 24 (15)/37 (24)/ 18 (12) | 39 (11)/120 (35)/ 36 (11)/72 (21)/ 75 (22) | 39 (11)/121 (35)/ 37 (11)/73 (21)/ 76 (22) |

*Formed from datasets (n): GSE17536 (167), GSE39582 (516).
†Formed from datasets (n): GSE13067 (69), GSE13294 (150), GSE14333 (149), GSE2109 (264), GSE23878 (31), GSE35896 (57), GSE37892 (121), KFSYCC (276).
§The CMS classification as reported by CRCSC combining the network and random forest classifiers.

Clinical characteristics and the Colorectal Cancer Subtyping Consortium (CRCSC) consensus molecular subtype classifications for each sample in Cohort A were also obtained from Synapse Project 2623706 and summarized herein. For the purpose of deriving and validating the CMS classifier and/or methodology, Cohort A was partitioned into training (n=683) and validation (n=1205) sets. The training set was defined to be all samples in the datasets GSE17536 and GSE39582.

Raw RNA-sequencing alignments (BAM files) were obtained from Genomic Data Commons (gdc(dot)cancer(dot)gov) for the TCGA colon cancer samples (COAD, n=382) and rectal cancer samples (READ, n=136). While normalized count data (FPKM-UQ) is available for these cohorts from Genomic Data Commons, we chose to compute count data for these cohorts using common analytical methods to facilitate comparison of the inventive classifier/methodology across the cohorts. We aligned the BAM files to the Ensembl version 90 human genome (ensembl(dot)org/index(dot)html) using the Bioconductor package Rsubread. Raw count values were normalized as transcripts per million (TPM) and gene expression values measured as log base 2 of TPM values. Patient-level clinical data and CMS classifications for COAD and READ were obtained from Synapse Project 2623706. Relapse-free survival data for COAD was obtained from Broad GDAC Firehose (gdac(dot)broadinstitute.(dot)org). To support the development of the inventive classifier/methodology, COAD was divided into training (n=189) and validation sets (n=193) balanced for CRCSC CMS subtypes.

Data from Cohort C (n=688), consisting of samples from the PETACC3 clinical trial for which mRNA was hybridized to the Almac custom Affymetrix microarray platform, were obtained from Synapse Project 2623706. The cohort was randomly divided into training (n=342) and validation (n=346) sets balanced for CRCSC CMS subtype.

The CRCSC reports CMS classifications obtained by network analysis, the random forest classifier, and a "CMS-fmal" classification that agrees with the network classification when there is a consensus among the contributing classifiers and agrees with the random forest classifier for non-consensus samples. In the present disclosure, the term "CRCSC CMS subtype" refers to "CMS-fmal" unless otherwise specified.

To train and validate recurrence risk related embodiments of the present disclosure, Cohort D was formed, which included samples from Cohort A for which relapse-free survival data is available. Table 2 presents characteristics of the colon cancer samples used for training and validation of these embodiments of the present disclosure. Included on Table 2 is additional data on Cohort B relevant to evaluation of a prognostic signature.

TABLE 2

| partition | Cohort D | | Cohort B | |
|---|---|---|---|---|
| | training (n = 203) | validation (n = 683) | training (n = 189) | validation (n = 193) |
| assay platform | Affymetrix hgu133plus2 | Affymetrix hgu133plus2 | RNA-seq | RNA-seq |
| dataset (n) | GSE14333 (91), GSE39582 (112) | GSE14333 (28), GSE17536 (138), GSE37892 (121), GSE39522 (396) | COAD (189) | COAD (193) |
| stage (1/2/3/4/NA) | 25/102/70/6/0 | 59/307/262/55/0 | 28/65/58/15/7 | 29/62/48/14/2 |
| T-stage (1/2/3/4/NA) | 2/9/77/17/98 | 9/32/260/85/297 | 6/24/126/16/1 | 4/34/104/13/0 |
| RFS 5-yr event (no/yes) | 152/51 | 494/189 | 129/44 | 128/27 |
| median follow up (months) | 44.4 | 42 | 19 | 26 |

Multistate Gene Models for Classification and Prognosis

The genomic scores used in the classification methods were defined using multistate methodology. This method associates the expression values of a gene in a cohort of samples with a vector of numbers termed the gene's risk score, comprised of a number between 0 and 1 for each sample in the cohort. A gene's risk score is derived from the vector of expression values by fitting a gaussian mixture model with resampling. In some cases, the expression values for a gene may give rise to multiple risk scores depending on the complexity of the mixture model fit.

The use of gene risk scores enables predictive scores to be computed using the same algorithm in multiple cohorts in which gene expression was measured with different technologies, as follows. Given cohorts S1 and S2 with similar clinical features and a gene g, consider risk scores r1 and r2 for g in S1 and S2, respectively. To assess the numerical equivalence of r1 and r2, we fit loess smoothing models L1, L2 for r1, r2 with respect to the vectors of risk score quantiles, x1, x2, respectively. Concatenate x1 and x2 to form the vector x and use L1 and L2 to predict curves s1 and s2 over x. In this way, we have extended r1 and r2 to curves s1 and s2 over a common domain. We define r1 and r2 to be equivalent risk scores if a linear fit of s1 to s2 has $R^2 \geq 0.90$.

The notion of equivalent risk scores for a gene g was used in two ways in the derivation of classifications. First, in selecting genes and risk scores for inclusion in the protocol, we restricted attention to those for which there are equivalent risk scores in all cohorts considered here (Cohorts A-C). Secondly, after selecting a preferred risk score for a gene g in one cohort, such as the Affymetrix training set, if there were multiple equivalent risk scores for g in a second cohort, such as COAD, we selected the one with maximal $R^2$ value, computed as above.

Statistical Methods

All statistical analyses were performed using R (www(dot)r-project(dot)org) and Bioconductor packages (bioconductor(dot)org). The package mclust was used for fitting mixture models, and survival analysis was performed with the survival package. The significance of a Cox proportional hazards (CPH) model was assessed with the P value of the logrank score test. The significance of a multivariate CPH over a CPH using a subset of the variables by applying a Chi-squared test to the differences of log-likelihoods of the two CPH models. The proportional hazard condition was tested with the cox.zph function. The expected survival at a time point for each value of a continuous variable will be estimated from a CPH using the rms package.

In a Cox proportional hazards model, the default hazard ratio represents the increased risk due to an increase of 1 unit in the covariate. For a continuous score (0-100), we reported the hazard ratio in increments of 50 so that the hazard ratio is numerically comparable to a hazard ratio for a discrete binary variable.

The ability of a continuous score to predict membership in a subtype will be assessed visually with the receiver operator characteristic (ROC) curve which plots sensitivity (y-axis) by 1—specificity (x-axis) for all values of the score. The ROC curve is a test of how the probability of membership varies with values of the continuous score. The area under the ROC curve (AUC) gives a numerical measure of a score's predictive significance. The quality of the prediction is better than random if AUC is >0.5 and improves as AUC increases up to 1.

The inventive subtyping methodology defines a discrete classification that predicts the four subtypes of the CRCSC CMS classification. The quality of the prediction was assessed using the overall accuracy, along with the sensitivity, specificity and balanced accuracy (mean of the sensitivity and specificity) for CMS1-4. These statistics were computed using the confusion Matrix function of the caret package.

Given a CMSpre-score S computed from gene risk scores predictive of a CMS in a cohort f samples, the positive predictive value (PPV) of a value v of S, is the ratio of the number of subtype samples with score≥v over the total number of samples with score≥v in the cohort. From the set PPV values associated with values of S, we used less smoothing to define a smooth non-decreasing score (0-1), called the CMS score. In the discrete CMS classifier, S was replaced with the associated CMS score.

CMS Pre-Score

For each CMS subtype, the inventive classifier/methodology includes or produces continuous score (0-100), subsequently called a CMS pre-score, that informs membership in the subtype. The genes used to define the scores that inform CMS 1-4 were selected by analysis of candidate genes in the Affymetrix training set and COAD training set. Specifically, for each of CMS 1-4, we first ranked the risk scores of genes by the level of significance in predicting the subtype in the Affymetrix training set. Table 3a presents the genes from which the CMS1-4 scores were computed. Specifically, Table 3a presents the 100 highest ranked candidate genes for CMS subtype predictive scores for each of CMS1-4. Then, for each subtype, we selected the 5 highly rank genes in the table of candidates, which were also highly ranked in COAD training set, as the preferred panel of genes to define the CMS scores.

TABLE 3a

| CMS subtype | ENTREZID | SYMBOL | p-value | Values subtype enriched | Rank | Preferred panel member |
|---|---|---|---|---|---|---|
| CMS1 | 6418 | SET | 2.10E−102 | low | 1 | |
| CMS1 | 9219 | MTA2 | 5.21E−89 | high | 2 | X |
| CMS1 | 10855 | HPSE | 5.32E−83 | high | 3 | |
| CMS1 | 3191 | HNRNPL | 1.11E−75 | high | 4 | |
| CMS1 | 9037 | SEMA5A | 4.44E−75 | low | 5 | |
| CMS1 | 10079 | ATP9A | 7.23E−75 | low | 6 | |
| CMS1 | 83737 | ITCH | 2.23E−74 | low | 7 | |
| CMS1 | 10140 | TOB1 | 2.29E−69 | low | 8 | |
| CMS1 | 8313 | AXIN2 | 2.76E−69 | low | 9 | |
| CMS1 | 54891 | INO80D | 9.88E−69 | low | 10 | |
| CMS1 | 57798 | GATAD1 | 1.15E−68 | low | 11 | |
| CMS1 | 998 | CDC42 | 7.38E−68 | low | 12 | X |
| CMS1 | 7105 | TSPAN6 | 4.42E−66 | low | 13 | X |
| CMS1 | 23475 | QPRT | 8.75E−66 | low | 14 | X |
| CMS1 | 6431 | SRSF6 | 3.37E−64 | high | 15 | |
| CMS1 | 3725 | JUN | 2.07E−61 | low | 16 | |
| CMS1 | 81786 | TRIM7 | 2.19E−61 | high | 17 | |
| CMS1 | 9554 | SEC22B | 2.70E−61 | low | 18 | |
| CMS1 | 1602 | DACH1 | 3.55E−60 | low | 19 | |
| CMS1 | 57168 | ASPHD2 | 3.86E−60 | high | 20 | X |
| CMS1 | 401474 | SAMD12 | 6.88E−60 | low | 21 | |
| CMS1 | 139322 | APOOL | 9.43E−60 | low | 22 | |
| CMS1 | 1783 | DYNC1L12 | 2.31E−59 | low | 23 | |
| CMS1 | 29966 | STRN3 | 5.24E−59 | high | 24 | |
| CMS1 | 80183 | RUBCNL | 2.54E−58 | low | 25 | |
| CMS1 | 8019 | BRD3 | 3.38E−57 | low | 26 | |
| CMS1 | 3549 | IHH | 3.78E−56 | low | 27 | |
| CMS1 | 27330 | RPS6KA6 | 6.86E−56 | low | 28 | |
| CMS1 | 10451 | VAV3 | 2.62E−55 | low | 29 | |
| CMS1 | 57211 | ADGRG6 | 1.69E−54 | high | 30 | |
| CMS1 | 81617 | CAB39L | 1.90E−54 | low | 31 | |
| CMS1 | 30811 | HUNK | 3.01E−54 | low | 32 | |
| CMS1 | 92211 | CDHR1 | 1.13E−53 | low | 33 | |
| CMS1 | 29974 | A1CF | 2.00E−53 | low | 34 | |
| CMS1 | 7453 | WARS | 2.05E−53 | high | 35 | |
| CMS1 | 10578 | GNLY | 2.52E−53 | high | 36 | |
| CMS1 | 54749 | EPDR1 | 4.20E−53 | low | 37 | |
| CMS1 | 4925 | NUCB2 | 1.04E−52 | high | 38 | |
| CMS1 | 54866 | PPP1R14D | 1.48E−52 | low | 39 | |
| CMS1 | 330 | BIRC3 | 2.77E−52 | high | 40 | |
| CMS1 | 64710 | NUCKS1 | 5.17E−52 | low | 41 | |

TABLE 3a-continued

| CMS subtype | ENTREZID | SYMBOL | p-value | Values subtype enriched | Rank | Preferred panel member |
|---|---|---|---|---|---|---|
| CMS1 | 10299 | 6-Mar | 7.43E−52 | low | 42 | |
| CMS1 | 3717 | JAK2 | 8.66E−52 | high | 43 | |
| CMS1 | 9547 | CXCL14 | 2.00E−51 | low | 44 | |
| CMS1 | 31 | ACACA | 2.17E−51 | high | 45 | |
| CMS1 | 222171 | PRR15 | 2.33E−51 | low | 46 | |
| CMS1 | 23014 | FBXO21 | 3.27E−51 | low | 47 | |
| CMS1 | 128866 | CHMP4B | 3.97E−51 | low | 48 | |
| CMS1 | 10656 | KHDRBS3 | 6.03E−51 | low | 49 | |
| CMS1 | 23657 | SLC7A11 | 1.15E−50 | high | 50 | |
| CMS1 | 9262 | STK17B | 3.47E−50 | high | 51 | |
| CMS1 | 51056 | LAP3 | 1.21E−49 | high | 52 | |
| CMS1 | 5500 | PPP1CB | 1.56E−49 | low | 53 | |
| CMS1 | 55000 | TUG1 | 1.80E−49 | low | 54 | |
| CMS1 | 5920 | RARRES3 | 4.20E−49 | high | 55 | |
| CMS1 | 22824 | HSPA4L | 1.26E−48 | high | 56 | |
| CMS1 | 11168 | PSIP1 | 1.30E−48 | high | 57 | |
| CMS1 | 9852 | EPM2AIP1 | 6.64E−48 | low | 58 | |
| CMS1 | 54894 | RNF43 | 8.00E−48 | low | 59 | |
| CMS1 | 2935 | GSPT1 | 2.70E−47 | low | 60 | |
| CMS1 | 10160 | FARP1 | 5.66E−47 | low | 61 | |
| CMS1 | 29126 | CD274 | 9.23E−47 | high | 62 | |
| CMS1 | 115362 | GBP5 | 1.05E−46 | high | 63 | |
| CMS1 | 387695 | C10orf99 | 1.27E−46 | low | 64 | |
| CMS1 | 5727 | PTCH1 | 3.72E−46 | low | 65 | |
| CMS1 | 219285 | SAMD9L | 4.57E−46 | high | 66 | |
| CMS1 | 2786 | GNG4 | 7.74E−46 | low | 67 | |
| CMS1 | 55661 | DDX27 | 7.97E−46 | low | 68 | |
| CMS1 | 359948 | IRF2BP2 | 8.34E−46 | low | 69 | |
| CMS1 | 259282 | BOD1L1 | 9.20E−46 | high | 70 | |
| CMS1 | 56937 | PMEPA1 | 1.17E−45 | low | 71 | |
| CMS1 | 4155 | MBP | 1.19E−45 | high | 72 | |
| CMS1 | 4152 | MBD1 | 2.60E−45 | high | 73 | |
| CMS1 | 83481 | EPPK1 | 3.89E−45 | high | 74 | |
| CMS1 | 56938 | ARNTL2 | 4.36E−45 | high | 75 | |
| CMS1 | 56829 | ZC3HAV1 | 7.47E−45 | high | 76 | |
| CMS1 | 83992 | CTTNBP2 | 8.91E−45 | low | 77 | |
| CMS1 | 57805 | CCAR2 | 1.21E−44 | high | 78 | |
| CMS1 | 28951 | TRIB2 | 1.57E−44 | high | 79 | |
| CMS1 | 80833 | APOL3 | 2.20E−44 | high | 80 | |
| CMS1 | 57216 | VANGL2 | 6.66E−44 | low | 81 | |
| CMS1 | 79442 | LRRC2 | 6.75E−44 | low | 82 | |
| CMS1 | 85407 | NKD1 | 1.07E−43 | low | 83 | |
| CMS1 | 200958 | MUC20 | 4.14E−43 | low | 84 | |
| CMS1 | 9306 | SOCS6 | 6.86E−43 | high | 85 | |
| CMS1 | 54509 | RHOF | 8.59E−43 | high | 86 | |
| CMS1 | 444 | ASPH | 8.62E−43 | high | 87 | |
| CMS1 | 169981 | SPIN3 | 9.37E−43 | low | 88 | |
| CMS1 | 5229 | PGGT1B | 1.20E−42 | low | 89 | |
| CMS1 | 7020 | TFAP2A | 1.62E−42 | high | 90 | |
| CMS1 | 79758 | DHRS12 | 1.81E−42 | low | 91 | |
| CMS1 | 11274 | USP18 | 3.02E−42 | high | 92 | |
| CMS1 | 80323 | CCDC68 | 3.42E−42 | high | 93 | |
| CMS1 | 55328 | RNLS | 4.31E−42 | low | 94 | |
| CMS1 | 51703 | ACSL5 | 4.99E−42 | low | 95 | |
| CMS1 | 10512 | SEMA3C | 6.47E−42 | low | 96 | |
| CMS1 | 2177 | FANCD2 | 1.18E−41 | high | 97 | |
| CMS1 | 6772 | STAT1 | 1.53E−41 | high | 98 | |
| CMS1 | 10206 | TRIM13 | 1.55E−41 | low | 99 | |
| CMS1 | 388610 | TRNP1 | 2.55E−41 | high | 100 | |
| CMS2 | 5326 | PLAGL2 | 8.13E−84 | high | 1 | X |
| CMS2 | 112858 | TP53RK | 9.89E−71 | high | 2 | X |
| CMS2 | 1057 | CELP | 2.12E−62 | high | 3 | |
| CMS2 | 6780 | STAU1 | 2.60E−62 | high | 4 | X |
| CMS2 | 23509 | POFUT1 | 5.34E−61 | high | 5 | X |
| CMS2 | 51497 | NELFCD | 3.66E−60 | high | 6 | |
| CMS2 | 430 | ASCL2 | 4.23E−60 | high | 7 | |
| CMS2 | 171023 | ASXL1 | 3.47E−59 | high | 8 | |
| CMS2 | 25980 | AAR2 | 2.91E−57 | high | 9 | |
| CMS2 | 23475 | QPRT | 3.96E−57 | high | 10 | |
| CMS2 | 22919 | MAPRE1 | 4.94E−56 | high | 11 | |
| CMS2 | 80183 | RUBCNL | 8.19E−56 | high | 12 | |
| CMS2 | 51526 | OSER1 | 2.76E−55 | high | 13 | |
| CMS2 | 28951 | TRIB2 | 3.57E−55 | low | 14 | |
| CMS2 | 1056 | CEL | 6.26E−55 | high | 15 | |
| CMS2 | 1846 | DUSP4 | 7.71E−54 | low | 16 | X |
| CMS2 | 644 | BLVRA | 9.93E−53 | low | 17 | |
| CMS2 | 9054 | NFS1 | 3.20E−52 | high | 18 | |

TABLE 3a-continued

| CMS subtype | ENTREZID | SYMBOL | p-value | Values subtype enriched | Rank | Preferred panel member |
|---|---|---|---|---|---|---|
| CMS2 | 55661 | DDX27 | 4.90E−52 | high | 19 | |
| CMS2 | 54894 | RNF43 | 1.58E−51 | high | 20 | |
| CMS2 | 58490 | RPRD1B | 2.79E−51 | high | 21 | |
| CMS2 | 4212 | MEIS2 | 5.58E−49 | low | 22 | |
| CMS2 | 128866 | CHMP4B | 9.82E−47 | high | 23 | |
| CMS2 | 140831 | ZSWIM3 | 1.20E−45 | high | 24 | |
| CMS2 | 84647 | PLA2G12B | 1.22E−45 | high | 25 | |
| CMS2 | 23314 | SATB2 | 1.32E−45 | high | 26 | |
| CMS2 | 7105 | TSPAN6 | 2.99E−45 | high | 27 | |
| CMS2 | 54915 | YTHDF1 | 1.90E−44 | high | 28 | |
| CMS2 | 81786 | TRIM7 | 4.00E−44 | low | 29 | |
| CMS2 | 10160 | FARP1 | 4.84E−43 | high | 30 | |
| CMS2 | 55076 | TMEM45A | 7.47E−43 | low | 31 | |
| CMS2 | 6624 | FSCN1 | 7.65E−43 | low | 32 | |
| CMS2 | 8836 | GGH | 2.65E−42 | high | 33 | |
| CMS2 | 7020 | TFAP2A | 7.45E−42 | low | 34 | |
| CMS2 | 5874 | RAB27B | 3.80E−41 | low | 35 | |
| CMS2 | 8942 | KYNU | 4.56E−41 | low | 36 | |
| CMS2 | 51012 | PRELID3B | 7.63E−41 | high | 37 | |
| CMS2 | 11264 | PXMP4 | 8.67E−41 | high | 38 | |
| CMS2 | 387119 | CEP85L | 1.96E−40 | low | 39 | |
| CMS2 | 25984 | KRT23 | 3.78E−40 | high | 40 | |
| CMS2 | 9194 | SLC16A7 | 4.06E−40 | low | 41 | |
| CMS2 | 55107 | ANO1 | 1.67E−39 | low | 42 | |
| CMS2 | 7529 | YWHAB | 4.00E−39 | high | 43 | |
| CMS2 | 4935 | GPR143 | 5.35E−39 | high | 44 | |
| CMS2 | 23305 | ACSL6 | 8.27E−39 | high | 45 | |
| CMS2 | 81572 | PDRG1 | 8.91E−39 | high | 46 | |
| CMS2 | 6556 | SLC11A1 | 1.20E−38 | low | 47 | |
| CMS2 | 128486 | FITM2 | 2.11E−38 | high | 48 | |
| CMS2 | 135228 | CD109 | 2.15E−38 | low | 49 | |
| CMS2 | 284252 | KCTD1 | 2.21E−38 | low | 50 | |
| CMS2 | 10551 | AGR2 | 2.39E−38 | low | 51 | |
| CMS2 | 51654 | CDK5RAP1 | 2.46E−38 | high | 52 | |
| CMS2 | 5321 | PLA2G4A | 3.71E−38 | low | 53 | |
| CMS2 | 10267 | RAMP1 | 5.11E−38 | low | 54 | |
| CMS2 | 1820 | ARID3A | 7.54E−38 | high | 55 | |
| CMS2 | 687 | KLF9 | 9.17E−38 | low | 56 | |
| CMS2 | 10079 | ATP9A | 1.47E−37 | high | 57 | |
| CMS2 | 81704 | DOCK8 | 2.07E−37 | low | 58 | |
| CMS2 | 2786 | GNG4 | 3.10E−37 | high | 59 | |
| CMS2 | 100505592 | GAPLINC | 5.51E−37 | low | 60 | |
| CMS2 | 59272 | ACE2 | 7.42E−37 | high | 61 | |
| CMS2 | 80704 | SLC19A3 | 9.44E−37 | high | 62 | |
| CMS2 | 7089 | TLE2 | 1.16E−36 | high | 63 | |
| CMS2 | 2918 | GRM8 | 3.95E−36 | high | 64 | |
| CMS2 | 100505783 | OSER1-AS1 | 4.90E−36 | high | 65 | |
| CMS2 | 57148 | RALGAPB | 2.56E−35 | high | 66 | |
| CMS2 | 5509 | PPP1R3D | 3.20E−35 | high | 67 | |
| CMS2 | 5552 | SRGN | 3.67E−35 | low | 68 | |
| CMS2 | 92689 | FAM114A1 | 5.28E−35 | low | 69 | |
| CMS2 | 85407 | NKD1 | 5.55E−35 | high | 70 | |
| CMS2 | 8856 | NR1I2 | 7.14E−35 | high | 71 | |
| CMS2 | 1396 | CRIP1 | 9.70E−35 | low | 72 | |
| CMS2 | 57446 | NDRG3 | 1.09E−34 | high | 73 | |
| CMS2 | 128346 | C1orf162 | 1.24E−34 | low | 74 | |
| CMS2 | 2069 | EREG | 1.33E−34 | high | 75 | |
| CMS2 | 10451 | VAV3 | 1.83E−34 | high | 76 | |
| CMS2 | 4688 | NCF2 | 4.82E−34 | low | 77 | |
| CMS2 | 7850 | IL1R2 | 5.04E−34 | low | 78 | |
| CMS2 | 79442 | LRRC2 | 1.28E−33 | high | 79 | |
| CMS2 | 493869 | GPX8 | 1.52E−33 | low | 80 | |
| CMS2 | 155465 | AGR3 | 1.66E−33 | low | 81 | |
| CMS2 | 643977 | FLJ32255 | 2.22E−33 | low | 82 | |
| CMS2 | 26115 | TANC2 | 2.24E−33 | low | 83 | |
| CMS2 | 10687 | PNMA2 | 3.69E−33 | low | 84 | |
| CMS2 | 79980 | DSN1 | 3.99E−33 | high | 85 | |
| CMS2 | 83658 | DYNLRB1 | 4.12E−33 | high | 86 | |
| CMS2 | 4069 | LYZ | 6.79E−33 | low | 87 | |
| CMS2 | 5203 | PFDN4 | 8.62E−33 | high | 88 | |
| CMS2 | 7130 | TNFAIP6 | 9.65E−33 | low | 89 | |
| CMS2 | 60436 | TGIF2 | 9.99E−33 | high | 90 | |
| CMS2 | 54890 | ALKBH5 | 1.88E−32 | low | 91 | |
| CMS2 | 51507 | RTFDC1 | 1.92E−32 | high | 92 | |
| CMS2 | 2213 | FCGR2B | 3.36E−32 | low | 93 | |
| CMS2 | 6532 | SLC6A4 | 4.80E−32 | high | 94 | |
| CMS2 | 83998 | REG4 | 5.89E−32 | low | 95 | |

TABLE 3a-continued

| CMS subtype | ENTREZID | SYMBOL | p-value | Values subtype enriched | Rank | Preferred panel member |
|---|---|---|---|---|---|---|
| CMS2 | 5948 | RBP2 | 8.04E−32 | high | 96 | |
| CMS2 | 25816 | TNFAIP8 | 1.07E−31 | low | 97 | |
| CMS2 | 9945 | GFPT2 | 1.28E−31 | low | 98 | |
| CMS2 | 3223 | HOXC6 | 1.34E−31 | low | 99 | |
| CMS2 | 5732 | PTGER2 | 1.74E−31 | low | 100 | |
| CMS3 | 4217 | MAP3K5 | 7.60E−52 | high | 1 | |
| CMS3 | 84666 | RETNLB | 1.32E−48 | high | 2 | X |
| CMS3 | 8857 | FCGBP | 6.06E−47 | high | 3 | |
| CMS3 | 7078 | TIMP3 | 9.32E−46 | low | 4 | X |
| CMS3 | 80150 | ASRGL1 | 1.26E−44 | high | 5 | X |
| CMS3 | 4151 | MB | 2.13E−41 | high | 6 | |
| CMS3 | 54596 | L1TD1 | 3.97E−40 | high | 7 | |
| CMS3 | 143458 | LDLRAD3 | 3.11E−39 | low | 8 | |
| CMS3 | 84189 | SLITRK6 | 3.69E−39 | high | 9 | X |
| CMS3 | 7410 | VAV2 | 9.99E−39 | low | 10 | |
| CMS3 | 5937 | RBMS1 | 1.14E−38 | low | 11 | X |
| CMS3 | 25837 | RAB26 | 1.33E−38 | high | 12 | |
| CMS3 | 10753 | CAPN9 | 2.08E−38 | high | 13 | |
| CMS3 | 192134 | B3GNT6 | 3.64E−38 | high | 14 | |
| CMS3 | 201501 | ZBTB7C | 1.26E−35 | high | 15 | |
| CMS3 | 9509 | ADAMTS2 | 1.42E−35 | low | 16 | |
| CMS3 | 140828 | LINC00261 | 1.88E−34 | high | 17 | |
| CMS3 | 84624 | FNDC1 | 2.27E−34 | low | 18 | |
| CMS3 | 1290 | COL5A2 | 2.53E−34 | low | 19 | |
| CMS3 | 405753 | DUOXA2 | 2.20E−33 | high | 20 | |
| CMS3 | 1278 | COL1A2 | 3.15E−33 | low | 21 | |
| CMS3 | 2335 | FN1 | 7.18E−33 | low | 22 | |
| CMS3 | 1295 | COL8A1 | 9.65E−33 | low | 23 | |
| CMS3 | 3488 | IGFBP5 | 1.35E−32 | low | 24 | |
| CMS3 | 9254 | CACNA2D2 | 1.78E−32 | high | 25 | |
| CMS3 | 155465 | AGR3 | 1.92E−32 | high | 26 | |
| CMS3 | 1428 | CRYM | 1.93E−31 | high | 27 | |
| CMS3 | 767 | CA8 | 4.08E−31 | high | 28 | |
| CMS3 | 375056 | MIA3 | 5.00E−31 | high | 29 | |
| CMS3 | 863 | CBFA2T3 | 7.38E−31 | high | 30 | |
| CMS3 | 51655 | RASD1 | 1.18E−30 | high | 31 | |
| CMS3 | 1462 | VCAN | 3.55E−30 | low | 32 | |
| CMS3 | 1306 | COL15A1 | 4.93E−30 | low | 33 | |
| CMS3 | 7058 | THBS2 | 1.33E−29 | low | 34 | |
| CMS3 | 2762 | GMDS | 1.76E−29 | high | 35 | |
| CMS3 | 5732 | PTGER2 | 2.21E−29 | high | 36 | |
| CMS3 | 3624 | INHBA | 2.28E−29 | low | 37 | |
| CMS3 | 10551 | AGR2 | 2.31E−29 | high | 38 | |
| CMS3 | 6678 | SPARC | 2.79E−29 | low | 39 | |
| CMS3 | 1277 | COL1A1 | 4.12E−29 | low | 40 | |
| CMS3 | 4583 | MUC2 | 1.16E−28 | high | 41 | |
| CMS3 | 5265 | SHPINA1 | 1.37E−28 | high | 42 | |
| CMS3 | 83998 | REG4 | 1.37E−28 | high | 43 | |
| CMS3 | 11228 | RASSF8 | 1.40E−28 | low | 44 | |
| CMS3 | 6695 | SPOCK1 | 1.53E−28 | low | 45 | |
| CMS3 | 23213 | SULF1 | 4.65E−28 | low | 46 | |
| CMS3 | 800 | CALD1 | 7.39E−28 | low | 47 | |
| CMS3 | 23158 | TBC1D9 | 1.11E−27 | low | 48 | |
| CMS3 | 4585 | MUC4 | 1.44E−27 | high | 49 | |
| CMS3 | 3373 | HYAL1 | 2.14E−27 | high | 50 | |
| CMS3 | 57535 | KIAA1324 | 2.47E−27 | high | 51 | |
| CMS3 | 474 | ATOH1 | 6.71E−27 | high | 52 | |
| CMS3 | 1051 | CEBPB | 7.06E−27 | low | 53 | |
| CMS3 | 11167 | FSTL1 | 8.28E−27 | low | 54 | |
| CMS3 | 1281 | COL3A1 | 8.68E−27 | low | 55 | |
| CMS3 | 3371 | TNC | 2.01E−26 | low | 56 | |
| CMS3 | 138065 | RNF183 | 2.05E−26 | high | 57 | |
| CMS3 | 27290 | SPINK4 | 2.63E−26 | high | 58 | |
| CMS3 | 3092 | HIP1 | 2.70E−26 | low | 59 | |
| CMS3 | 2983 | GUCY1B3 | 6.04E−26 | low | 60 | |
| CMS3 | 2200 | FBN1 | 1.11E−25 | low | 61 | |
| CMS3 | 2619 | GAS1 | 1.45E−25 | low | 62 | |
| CMS3 | 112609 | MRAP2 | 2.62E−25 | high | 63 | |
| CMS3 | 9945 | GFPT2 | 4.39E−25 | low | 64 | |
| CMS3 | 50863 | NTM | 6.59E−25 | low | 65 | |
| CMS3 | 6938 | TCF12 | 7.22E−25 | high | 66 | |
| CMS3 | 283651 | HMGN2P46 | 7.47E−25 | high | 67 | |
| CMS3 | 57221 | ARFGEF3 | 7.71E−25 | high | 68 | |
| CMS3 | 1293 | COL6A3 | 9.51E−25 | low | 69 | |
| CMS3 | 8522 | GAS7 | 1.09E−24 | low | 70 | |
| CMS3 | 9742 | IFT140 | 1.20E−24 | high | 71 | |
| CMS3 | 43849 | KLK12 | 1.54E−24 | high | 72 | |

TABLE 3a-continued

| CMS subtype | ENTREZID | SYMBOL | p-value | Values subtype enriched | Rank | Preferred panel member |
|---|---|---|---|---|---|---|
| CMS3 | 100505501 | LOC100505501 | 2.02E−24 | high | 73 | |
| CMS3 | 8537 | BCAS1 | 3.35E−24 | high | 74 | |
| CMS3 | 9783 | RIMS3 | 3.79E−24 | high | 75 | |
| CMS3 | 59345 | GNB4 | 4.08E−24 | low | 76 | |
| CMS3 | 1373 | CPS1 | 4.74E−24 | high | 77 | |
| CMS3 | 123036 | TC2N | 6.84E−24 | high | 78 | |
| CMS3 | 3671 | ISLR | 6.89E−24 | low | 79 | |
| CMS3 | 8038 | ADAM12 | 7.80E−24 | low | 80 | |
| CMS3 | 23563 | CHST5 | 8.21E−24 | high | 81 | |
| CMS3 | 84662 | GLIS2 | 9.66E−24 | low | 82 | |
| CMS3 | 2069 | EREG | 1.66E−23 | low | 83 | |
| CMS3 | 25803 | SPDEF | 1.96E−23 | high | 84 | |
| CMS3 | 3816 | KLK1 | 2.22E−23 | high | 85 | |
| CMS3 | 11012 | KLK11 | 2.94E−23 | high | 86 | |
| CMS3 | 80055 | PGAP1 | 3.45E−23 | high | 87 | |
| CMS3 | 399959 | MIR100HG | 3.47E−23 | low | 88 | |
| CMS3 | 81849 | ST6GALNAC5 | 3.81E−23 | low | 89 | |
| CMS3 | 6947 | TCN1 | 3.82E−23 | high | 90 | |
| CMS3 | 6926 | TBX3 | 5.30E−23 | high | 91 | |
| CMS3 | 399948 | COLCA1 | 5.37E−23 | high | 92 | |
| CMS3 | 59277 | NTN4 | 8.05E−23 | high | 93 | |
| CMS3 | 94121 | SYTL4 | 8.19E−23 | low | 94 | |
| CMS3 | 2487 | FRZB | 1.11E−22 | high | 95 | |
| CMS3 | 55 | ACPP | 1.73E−22 | high | 96 | |
| CMS3 | 1179 | CLCA1 | 2.10E−22 | high | 97 | |
| CMS3 | 7033 | TFF3 | 3.35E−22 | high | 98 | |
| CMS3 | 80114 | BICC1 | 3.63E−22 | low | 99 | |
| CMS3 | 8828 | NRP2 | 4.18E−22 | low | 100 | |
| CMS4 | 23414 | ZFPM2 | 5.59E−109 | high | 1 | X |
| CMS4 | 30008 | EFEMP2 | 2.25E−103 | high | 2 | |
| CMS4 | 27295 | PDLIM3 | 1.74E−101 | high | 3 | X |
| CMS4 | 2737 | GLI3 | 2.41E−101 | high | 4 | |
| CMS4 | 143903 | LAYN | 4.30E−100 | high | 5 | X |
| CMS4 | 154810 | AMOTL1 | 9.59E−99 | high | 6 | |
| CMS4 | 11037 | STON1 | 6.67E−98 | high | 7 | X |
| CMS4 | 7145 | TNS1 | 2.08E−95 | high | 8 | |
| CMS4 | 9590 | AKAP12 | 7.55E−93 | high | 9 | |
| CMS4 | 5178 | PEG3 | 1.31E−92 | high | 10 | |
| CMS4 | 23194 | FBXL7 | 5.11E−91 | high | 11 | |
| CMS4 | 4256 | MGP | 6.15E−91 | high | 12 | |
| CMS4 | 10000 | AKT3 | 1.01E−90 | high | 13 | |
| CMS4 | 1410 | CRYAB | 4.52E−89 | high | 14 | |
| CMS4 | 862 | RUNX1T1 | 1.91E−88 | high | 15 | |
| CMS4 | 5740 | PTGIS | 2.54E−86 | high | 16 | |
| CMS4 | 4286 | MITF | 4.26E−86 | high | 17 | |
| CMS4 | 83871 | RAB34 | 7.47E−86 | high | 18 | |
| CMS4 | 4211 | MEIS1 | 3.93E−85 | high | 19 | |
| CMS4 | 165 | AEBP1 | 4.62E−85 | high | 20 | X |
| CMS4 | 6695 | SPOCK1 | 5.42E−85 | high | 21 | |
| CMS4 | 1292 | COL6A2 | 6.01E−85 | high | 22 | |
| CMS4 | 9353 | SLIT2 | 8.82E−85 | high | 23 | |
| CMS4 | 4131 | MAP1B | 2.68E−84 | high | 24 | |
| CMS4 | 8639 | AOC3 | 1.07E−83 | high | 25 | |
| CMS4 | 5549 | PRELP | 9.07E−83 | high | 26 | |
| CMS4 | 54796 | BNC2 | 3.81E−82 | high | 27 | |
| CMS4 | 147906 | DACT3 | 5.03E−82 | high | 28 | |
| CMS4 | 8828 | NRP2 | 8.54E−82 | high | 29 | |
| CMS4 | 91653 | BOC | 2.15E−81 | high | 30 | |
| CMS4 | 57616 | TSHZ3 | 2.71E−81 | high | 31 | |
| CMS4 | 144165 | PRICKLE1 | 1.15E−80 | high | 32 | |
| CMS4 | 6383 | SDC2 | 1.29E−79 | high | 33 | |
| CMS4 | 4675 | NAP1L3 | 2.04E−79 | high | 34 | |
| CMS4 | 439921 | MXRA7 | 6.53E−77 | high | 35 | |
| CMS4 | 51309 | ARMCX1 | 2.88E−76 | high | 36 | |
| CMS4 | 7424 | VEGFC | 5.16E−76 | high | 37 | |
| CMS4 | 56967 | C14orf132 | 7.77E−76 | high | 38 | |
| CMS4 | 10082 | GPC6 | 8.65E−75 | high | 39 | |
| CMS4 | 5136 | PDE1A | 1.70E−74 | high | 40 | |
| CMS4 | 151887 | CCDC80 | 2.81E−74 | high | 41 | |
| CMS4 | 25927 | CNRIP1 | 4.91E−74 | high | 42 | |
| CMS4 | 57608 | KIAA1462 | 5.76E−74 | high | 43 | |
| CMS4 | 1346 | COX7A1 | 3.56E−73 | high | 44 | |
| CMS4 | 192668 | CYS1 | 1.99E−72 | high | 45 | |
| CMS4 | 1842 | ECM2 | 2.11E−72 | high | 46 | |
| CMS4 | 1000 | CDH2 | 5.56E−72 | high | 47 | |
| CMS4 | 9902 | MRC2 | 2.28E−71 | high | 48 | |
| CMS4 | 1296 | COL8A2 | 3.18E−71 | high | 49 | |

TABLE 3a-continued

| CMS subtype | ENTREZID | SYMBOL | p-value | Values subtype enriched | Rank | Preferred panel member |
|---|---|---|---|---|---|---|
| CMS4 | 1311 | COMP | 7.33E−71 | high | 50 | |
| CMS4 | 25925 | ZNF521 | 8.15E−71 | high | 51 | |
| CMS4 | 399959 | MIR100HG | 9.16E−71 | high | 52 | |
| CMS4 | 123920 | CMTM3 | 2.03E−70 | high | 53 | |
| CMS4 | 83700 | JAM3 | 2.54E−70 | high | 54 | |
| CMS4 | 50507 | NOX4 | 6.32E−70 | high | 55 | |
| CMS4 | 2121 | EVC | 1.52E−69 | high | 56 | |
| CMS4 | 23111 | SPG20 | 6.10E−69 | high | 57 | |
| CMS4 | 10278 | EFS | 9.58E−69 | high | 58 | |
| CMS4 | 5010 | CLDN11 | 1.82E−68 | high | 59 | |
| CMS4 | 85453 | TSPYL5 | 8.87E−68 | high | 60 | |
| CMS4 | 58494 | JAM2 | 8.93E−68 | high | 61 | |
| CMS4 | 114907 | FBXO32 | 9.99E−68 | high | 62 | |
| CMS4 | 8434 | RECK | 1.05E−67 | high | 63 | |
| CMS4 | 25802 | LMOD1 | 2.20E−67 | high | 64 | |
| CMS4 | 57198 | ATP8B2 | 2.29E−67 | high | 65 | |
| CMS4 | 128553 | TSHZ2 | 2.70E−67 | high | 66 | |
| CMS4 | 83604 | TMEM47 | 3.20E−67 | high | 67 | |
| CMS4 | 1687 | DFNA5 | 3.25E−67 | high | 68 | |
| CMS4 | 401097 | C3orf80 | 1.07E−66 | high | 69 | |
| CMS4 | 1281 | COL3A1 | 5.87E−66 | high | 70 | |
| CMS4 | 9945 | GFPT2 | 6.77E−66 | high | 71 | |
| CMS4 | 26353 | HSPB8 | 6.95E−66 | high | 72 | |
| CMS4 | 10979 | FERMT2 | 8.30E−66 | high | 73 | |
| CMS4 | 79745 | CLIP4 | 1.49E−65 | high | 74 | |
| CMS4 | 27303 | RBMS3 | 3.89E−65 | high | 75 | |
| CMS4 | 284119 | CAVIN1 | 4.67E−65 | high | 76 | |
| CMS4 | 25959 | KANK2 | 1.02E−64 | high | 77 | |
| CMS4 | 1009 | CDH11 | 1.11E−64 | high | 78 | |
| CMS4 | 5350 | PLN | 1.18E−64 | high | 79 | |
| CMS4 | 11117 | EMILIN1 | 4.41E−64 | high | 80 | |
| CMS4 | 84168 | ANTXR1 | 2.15E−63 | high | 81 | |
| CMS4 | 7077 | TIMP2 | 2.41E−63 | high | 82 | |
| CMS4 | 79827 | CLMP | 2.73E−63 | high | 83 | |
| CMS4 | 5587 | PRKD1 | 3.72E−63 | high | 84 | |
| CMS4 | 1264 | CNN1 | 6.28E−63 | high | 85 | |
| CMS4 | 1545 | CYP1B1 | 1.02E−62 | high | 86 | |
| CMS4 | 83872 | HMCN1 | 1.38E−62 | high | 87 | |
| CMS4 | 166336 | PRICKLE2 | 2.12E−62 | high | 88 | |
| CMS4 | 7060 | THBS4 | 3.04E−62 | high | 89 | |
| CMS4 | 23704 | KCNE4 | 5.09E−62 | high | 90 | |
| CMS4 | 1136 | CHRNA3 | 5.10E−62 | high | 91 | |
| CMS4 | 8910 | SGCE | 5.48E−62 | high | 92 | |
| CMS4 | 7345 | UCHL1 | 1.95E−61 | high | 93 | |
| CMS4 | 253827 | MSRB3 | 3.36E−61 | high | 94 | |
| CMS4 | 8483 | CILP | 4.92E−61 | high | 95 | |
| CMS4 | 134111 | UBE2QL1 | 7.20E−61 | high | 96 | |
| CMS4 | 7220 | TRPC1 | 1.02E−60 | high | 97 | |
| CMS4 | 55228 | PNMAL1 | 1.11E−60 | high | 98 | |
| CMS4 | 7043 | TGFB3 | 6.23E−60 | high | 99 | |
| CMS4 | 8572 | PDLIM4 | 6.30E−60 | high | 100 | |

In some embodiments of the present disclosure, a suitable number of genes that are statistically predictive of membership in the CMS1 subtype can be included in a first group of genes (or genetic elements), from which a smaller number of representative genes can be selected for analysis. Based on the gene expression level (e.g., as measured through RNA quantification) of each of the representative genes from the first group of genetic elements, a first CMS score representative of a probability that the CMS of the colorectal cancer is CMS1 can be determined. For example, in at least one embodiment, the 20 highest ranking genes (e.g., by p-value analysis), that are statistically predictive of membership in the CMS1 subtype can be included in the first group of genes. The expression level of 5 of these 20 genes can be determined and used to calculate a first CMS score representative of a probability that the CMS of the colorectal cancer is CMS1.

Alternatively, the 25 highest ranking genes, 30 highest ranking genes, 35 highest ranking genes, 40 highest ranking genes, 45 highest ranking genes, 50 highest ranking genes, 60 highest ranking genes, 70 highest ranking genes, 80 highest ranking genes, and so forth, or the 18 highest ranking genes, 16 highest ranking genes, Is highest ranking genes, 12 highest ranking genes, 10 highest ranking genes, 8 highest ranking genes, 6 highest ranking genes, 5 highest ranking genes, and so forth, that are statistically predictive of membership in the CMS1 subtype can be included in the first group of genes. In certain embodiments, any suitable number of genes between the 3 highest ranking genes and all 100 genes that are statistically predictive of membership in the CMS1 subtype can be included in the first group of genes.

In some embodiments, using the highest-ranking genes may not be required. For instance, in some embodiments, the first group of genes may include genes that are statistically predictive of membership in CMS1 but are ranked lower than other (higher ranking) genes. In some embodiments, the first group of genes may include (at least) 4, 5, 6, 7, 8, 9, 10, 11, 12, 13, 14, 15, 16, 18, 20, 25, 30, or more genes that are not among the very highest-ranking genes. For instance, in at least one embodiment, one or more of the top 5, 10, 15, 20, 25, or 30 highest-ranking genes may not be included in the first group of genetic elements.

Similarly, any suitable number of representative genes, out of or from the first group of genes, can be selected for analysis. For example, at least 3 genes from the first group of genes can be selected for analysis. The respective expression levels of these 3 representative genes (or the RNA transcripts thereof) can be determined and used to calculate the first CMS score representative of a probability that the CMS of the colorectal cancer is CMS1. Thus, the CMS classifier methodology can include determining, based on the expression level of each of the at least three RNA transcripts from a first group of genetic elements, a first CMS score representative of a probability that the CMS of the colorectal cancer is CMS1.

In some embodiments, at least 4, 5, 6, 7, 8, 9, 10, 11, 12, 13, 14, 15, 20, or 25 genes (or RNA transcripts) from the first group can be measured to calculate the first CMS score. In some embodiments, less than 100, 90, 80, 70, 60, 50, 40, 30, 25, 20, 15, 10, 9, 8, 7, 6, 5, or 4 genes (or RNA transcripts) from the first group can be measured to calculate the first CMS score. In some embodiments, (about) between 3 and 100, between 3 and 80, between 3 and 60, between 3 and 50, between 3 and 25, between 3 and 20, between 3 and 15, between 3 and 10, between 3 and 8, between 3 and 5, between 4 and 80, between 4 and 60, between 4 and 50, between 4 and 25, between 4 and 20, between 4 and 15, between 4 and 10, between 4 and 8, between 4 and 5, between 5 and 80, between 5 and 60, between 5 and 50, between 5 and 25, between 5 and 20, between 5 and 15, between 5 and 10, or between 5 and 8 genes (or RNA transcripts), or any number of genes or range of numbers of genes therebetween, from the first group can be measured to calculate the first CMS score.

In some embodiments, the selected representative genes (or RNA transcripts), or number thereof, can be the top or highest-ranking genes or number of genes (i.e., the most predictive of membership in the CMS1 subtype). In certain embodiments, some of the selected representative genes (or RNA transcripts), or number thereof, can be among the top genes or number of genes predictive of membership in the CMS1 subtype, while others of the selected representative genes (or RNA transcripts), or number thereof, can be less predictive of membership in the CMS1 subtype than other genes (or RNA transcripts) that are not included in the group or set of representative genes (or RNA transcripts). In some embodiments, the selected representative genes (or RNA transcripts), or number thereof, can be still be predictive of membership in the CMS1 subtype, but may be less predictive than genes (or RNA transcripts) that are not included in the set of representative genes (or RNA transcripts).

In similar manner, in some embodiments of the present disclosure, a suitable number of genes that are statistically predictive of membership in the CMS2 subtype can be included in a second group of genetic elements, from which a smaller number of representative genes can be selected for analysis. Based on the gene expression level (e.g., as measured through RNA quantification) of each of the representative genes from the second group of genetic elements, a second CMS score representative of a probability that the CMS of the colorectal cancer is CMS2 can be determined. For example, in at least one embodiment, the 20 highest ranking genes (e.g., by p-value analysis), that are statistically predictive of membership in the CMS2 subtype can be included in the second group of genes. The expression level of 5 of these 20 genes can be determined and used to calculate a second CMS score representative of a probability that the CMS of the colorectal cancer is CMS2. Alternative numbers, ranges, types, and/or rankings of genes (or RNA transcripts) set for, illustratively, with reference to CMS1 are incorporated for CMS2.

Likewise, in some embodiments of the present disclosure, a suitable number of genes that are statistically predictive of membership in the CMS3 subtype can be included in a third group of genetic elements, from which a smaller number of representative genes can be selected for analysis. Based on the gene expression level (e.g., as measured through RNA quantification) of each of the representative genes from the third group of genetic elements, a third CMS score representative of a probability that the CMS of the colorectal cancer is CMS3 can be determined. For example, in at least one embodiment, the 20 highest ranking genes (e.g., by p-value analysis), that are statistically predictive of membership in the CMS3 subtype can be included in the third group of genes. The expression level of 5 of these 20 genes can be determined and used to calculate a third CMS score representative of a probability that the CMS of the colorectal cancer is CMS3. Alternative numbers, ranges, types, and/or rankings of genes (or RNA transcripts) set for, illustratively, with reference to CMS 1 are incorporated for CMS3.

Moreover, in some embodiments of the present disclosure, a suitable number of genes that are statistically predictive of membership in the CMS4 subtype can be included in a fourth group of genetic elements, from which a smaller number of representative genes can be selected for analysis. Based on the gene expression level (e.g., as measured through RNA quantification) of each of the representative genes from the fourth group of genetic elements, a fourth CMS score representative of a probability that the CMS of the colorectal cancer is CMS4 can be determined. For example, in at least one embodiment, the 20 highest ranking genes (e.g., by p-value analysis), that are statistically predictive of membership in the CMS4 subtype can be included in the fourth group of genes. The expression level of 5 of these 20 genes can be determined and used to calculate a fourth CMS score representative of a probability that the CMS of the colorectal cancer is CMS4. Alternative numbers, ranges, types, and/or rankings of genes (or RNA transcripts) set for, illustratively, with reference to CMS1 are incorporated for CMS4.

By comparing the CMS score for CMS1 with the CMS score for CMS2 with the CMS score for CMS3 with the CMS score for CMS4, one can determine which score represents the highest level of predictive confidence for CMS subtyping or classification. This comparison may determine a maximal CMS score. As described in further detail herein, in some embodiments, one or more of the CMS scores can be above a threshold level of predictive confidence for CMS subtyping or classification.

In Table 3a, the number in the p-value column represents the p-value of a statistical test for predictive significance of the gene's risk score in Affymetrix training set. In the values subtype enriched column, "low" means low expression values of gene are more likely to be in the subtype and "high" means high expression values of gene are more likely to be in the subtype. A mark ("X") in the preferred panel member column indicates the genes included in a preferred panel defined by ranking in both Affymetrix training set and COAD training set. Thus, a preferred panel comprises the genes presented in Table 3b.

TABLE 3b

| CMS subtype | ENTREZID | SYMBOL | p-value | Values subtype enriched | Rank | Preferred panel member |
|---|---|---|---|---|---|---|
| CMS1 | 9219 | MTA2 | 5.21E-89 | high | 2 | X |
| CMS1 | 998 | CDC42 | 7.38E-68 | low | 12 | X |
| CMS1 | 7105 | TSPAN6 | 4.42E-66 | low | 13 | X |
| CMS1 | 23475 | QPRT | 8.75E-66 | low | 14 | X |
| CMS1 | 57168 | ASPHD2 | 3.86E-60 | high | 20 | X |
| CMS2 | 5326 | PLAGL2 | 8.13E-84 | high | 1 | X |
| CMS2 | 112858 | TP53RK | 9.89E-71 | high | 2 | X |
| CMS2 | 6780 | STAU1 | 2.60E-62 | high | 4 | X |
| CMS2 | 23509 | POFUT1 | 5.34E-61 | high | 5 | X |
| CMS2 | 1846 | DUSP4 | 7.71E-54 | low | 16 | X |
| CMS3 | 84666 | RETNLB | 1.32E-48 | high | 2 | X |
| CMS3 | 7078 | TIMP3 | 9.32E-46 | low | 4 | X |
| CMS3 | 80150 | ASRGL1 | 1.26E-44 | high | 5 | X |
| CMS3 | 84189 | SLITRK6 | 3.69E-39 | high | 9 | X |
| CMS3 | 5937 | RBMS1 | 1.14E-38 | low | 11 | X |
| CMS4 | 23414 | ZFPM2 | 5.59E-109 | high | 1 | X |
| CMS4 | 27295 | PDLIM3 | 1.74E-101 | high | 3 | X |
| CMS4 | 143903 | LAYN | 4.30E-100 | high | 5 | X |
| CMS4 | 11037 | STON1 | 6.67E-98 | high | 7 | X |
| CMS4 | 165 | AEBP1 | 4.62E-85 | high | 20 | X |

In an alternative embodiment, 20 or more genes can make up each group of genetic elements. Table 3c, for example, includes 29 of the predictively-significant genes for which the CMS subtype column has the value CMS1, 22 of the predictively-significant genes for which the CMS subtype column has the value CMS2, 26 of the predictively-significant genes for which the CMS subtype column has the value CMS3, and 29 of the predictively-significant genes for which the CMS subtype column has the value CMS4.

TABLE 3c

| CMS subtype | ENTREZID | Symbol | Rank | Direction |
|---|---|---|---|---|
| CMS1 | 6418 | SET | 1 | − |
| CMS1 | 9219 | MTN2 | 2 | + |
| CMS1 | 10855 | HPSE | 3 | + |
| CMS1 | 3191 | HNRNPL | 4 | − |
| CMS1 | 9037 | SEMA5A | 5 | + |
| CMS1 | 10079 | ATP9A | 6 | + |
| CMS1 | 83737 | ITCH | 7 | + |
| CMS1 | 10140 | TOB1 | 8 | − |
| CMS1 | 8313 | AXIN2 | 9 | + |
| CMS1 | 54891 | INO80D | 10 | − |
| CMS1 | 57798 | GATAD1 | 11 | + |
| CMS1 | 998 | CDC42 | 12 | − |
| CMS1 | 7105 | TSPAN6 | 13 | + |
| CMS1 | 23475 | QPRT | 14 | + |
| CMS1 | 6431 | SRSF6 | 15 | − |
| CMS1 | 3725 | JUN | 16 | + |
| CMS1 | 81786 | TRIM7 | 17 | + |
| CMS1 | 9554 | SEC22B | 18 | − |
| CMS1 | 1602 | DACH1 | 19 | + |
| CMS1 | 57168 | ASPHD2 | 20 | + |
| CMS1 | 401474 | SAMD12 | 21 | + |
| CMS1 | 139322 | APOOL | 22 | + |
| CMS1 | 1783 | DYNC1LI2 | 23 | + |
| CMS1 | 29966 | STRN3 | 24 | + |
| CMS1 | 80183 | RUBCNL | 25 | + |
| CMS1 | 8019 | BRD3 | 26 | + |
| CMS1 | 3549 | IHH | 27 | + |
| CMS1 | 27330 | RPS6KA6 | 28 | + |
| CMS1 | 10451 | VAV3 | 29 | + |
| CMS2 | 5326 | PLAGL2 | 1 | + |
| CMS2 | 112858 | TP53RK | 2 | + |
| CMS2 | 1057 | CELP | 3 | + |
| CMS2 | 6780 | STAU1 | 4 | + |
| CMS2 | 23509 | POFUT1 | 5 | + |
| CMS2 | 51497 | NELFCD | 6 | + |
| CMS2 | 430 | ASCL2 | 7 | + |
| CMS2 | 171023 | ASXL1 | 8 | + |

TABLE 3c-continued

| CMS subtype | ENTREZID | Symbol | Rank | Direction |
|---|---|---|---|---|
| CMS2 | 25980 | AAR2 | 9 | + |
| CMS2 | 23475 | QPRT | 10 | + |
| CMS2 | 22919 | MAPRE1 | 11 | + |
| CMS2 | 80183 | RUBCNL | 12 | + |
| CMS2 | 51526 | OSER1 | 13 | + |
| CMS2 | 28951 | TRIB2 | 14 | + |
| CMS2 | 1056 | CEL | 15 | + |
| CMS2 | 1846 | DUSP4 | 16 | + |
| CMS2 | 644 | BLVRA | 17 | + |
| CMS2 | 9054 | NFS1 | 18 | + |
| CMS2 | 55661 | DDX27 | 19 | + |
| CMS2 | 54894 | RNF43 | 20 | + |
| CMS2 | 58490 | RPRD1B | 21 | + |
| CMS2 | 4212 | MEIS2 | 22 | + |
| CMS3 | 4217 | MAP3K5 | 1 | + |
| CMS3 | 84666 | RETNLB | 2 | + |
| CMS3 | 8857 | FCGBP | 3 | + |
| CMS3 | 7078 | TIMP3 | 4 | + |
| CMS3 | 80150 | ASRGL1 | 5 | + |
| CMS3 | 4151 | MB | 6 | + |
| CMS3 | 54596 | L1TD1 | 7 | + |
| CMS3 | 143458 | LDLRAD3 | 8 | + |
| CMS3 | 84189 | SLITRKE | 9 | + |
| CMS3 | 7410 | VAV2 | 10 | + |
| CMS3 | 5937 | RBMS1 | 11 | + |
| CMS3 | 25837 | RAB26 | 12 | + |
| CMS3 | 10753 | CAPN9 | 13 | + |
| CMS3 | 192134 | B3GNT6 | 14 | + |
| CMS3 | 201501 | ZBTB7C | 15 | + |
| CMS3 | 9509 | ADAMTS2 | 16 | + |
| CMS3 | 140828 | LINC00261 | 17 | + |
| CMS3 | 84624 | FNDC1 | 18 | + |
| CMS3 | 1290 | COL5A2 | 19 | + |
| CMS3 | 405753 | DUOXA2 | 20 | + |
| CMS3 | 1278 | COL1A2 | 21 | + |
| CMS3 | 2335 | FN1 | 22 | + |
| CMS3 | 1295 | COL8A1 | 23 | + |
| CMS3 | 3488 | IGFBP5 | 24 | + |
| CMS3 | 9254 | CACNA2D2 | 25 | + |
| CMS3 | 155465 | AGR3 | 26 | + |
| CMS4 | 23414 | ZFPM2 | 1 | + |
| CMS4 | 30008 | EFEMP2 | 2 | + |
| CMS4 | 27295 | PDLIM3 | 3 | + |
| CMS4 | 2737 | GLI3 | 4 | + |
| CMS4 | 143903 | LAYN | 5 | + |
| CMS4 | 154810 | AMOTL1 | 6 | + |
| CMS4 | 11037 | STON1 | 7 | + |
| CMS4 | 7145 | TNS1 | 8 | + |
| CMS4 | 9590 | AKAP12 | 9 | + |

TABLE 3c-continued

| CMS subtype | ENTREZID | Symbol | Rank | Direction |
|---|---|---|---|---|
| CMS4 | 5178 | PEG3 | 10 | + |
| CMS4 | 23194 | FBXL7 | 11 | + |
| CMS4 | 4256 | MGP | 12 | + |
| CMS4 | 10000 | AKT3 | 13 | + |
| CMS4 | 1410 | CRYAB | 14 | + |
| CMS4 | 862 | RUNX1T1 | 15 | + |
| CMS4 | 5740 | PTGIS | 16 | + |
| CMS4 | 4286 | MITF | 17 | + |
| CMS4 | 83871 | RAB34 | 18 | + |
| CMS4 | 4211 | MEIS1 | 19 | + |
| CMS4 | 165 | AEBP1 | 20 | + |
| CMS4 | 6695 | SPOCK1 | 21 | + |
| CMS4 | 1292 | COL6A2 | 22 | + |
| CMS4 | 9353 | SLIT2 | 23 | + |
| CMS4 | 4131 | MAP1B | 24 | + |
| CMS4 | 8639 | AOC3 | 25 | + |
| CMS4 | 5549 | PRELP | 26 | + |
| CMS4 | 54796 | BNC2 | 27 | + |
| CMS4 | 147906 | DACT3 | 28 | + |
| CMS4 | 8828 | NRP2 | 29 | + | direction is "+" if increasing expressing predicts membership, it is "−", otherwise.

Alternatively, a preferred panel can comprise the genes representing the top 3, 4, 5, 6, 7, 8, 9, 10, 11, 12, 13, 14, 15, 16, 17, 18, 19, 20, 21, 22, 23, 24, or 25 (or more) predictive genes in each CMS.

A CMS1 score can be derived by computing the mean of the gene risk scores of a distinguished set of gene risk scores from among the candidate genes from each group. In certain embodiments, the expression of any 3, 4, 5, 6, or more genes may be used to determine a CMS1 score that gives a statistically significant prediction. To select a preferred panel of genes, one may compare the fits of gene risk scores in the CMS-training data, TCGA-COAD and PETACC-3, giving preference to the genes in which the proportions of samples with gene risk scores above 0.5 are the closest. Restricting to the preferred candidates, one may compute a CMS1 score, for example, for increasing numbers of genes.

In at least one embodiment, inclusion of more than 5 genes from any predictive group of genes may not add further to (or enhance) the predictive nature of the CMS score calculated therefrom. In an illustrative embodiment, a CMS1 score derived from the 5 preferred genes in Table 3d an result in an optimal score for prediction of CMS1, a CMS2 score derived from the preferred genes in Table 3d can result in an optimal score for prediction of CMS2, a CMS3 score derived from the 5 preferred genes in Table 3d can result in an optimal score for prediction of CMS3, and CMS4 score derived from the 5 preferred genes in Table 3d can result in an optimal score for prediction of CMS4.

TABLE 3d

| CMS subtype | ENTREZID | symbol | rank | direction |
|---|---|---|---|---|
| CMS1 | 9219 | MTA2 | 1 | + |
| CMS1 | 57168 | ASPHD2 | 2 | + |
| CMS1 | 7105 | TSPAN6 | 3 | − |
| CMS1 | 23475 | QPRT | 4 | − |
| CMS1 | 998 | CDC42 | 5 | − |
| CMS2 | 112858 | TP53RK | 1 | + |
| CMS2 | 5326 | PLAGL2 | 2 | + |
| CMS2 | 23509 | POFUT1 | 3 | + |
| CMS2 | 6780 | STAU1 | 4 | + |
| CMS2 | 1846 | DUSP4 | 5 | − |
| CMS3 | 7078 | TIMP3 | 1 | − |
| CMS3 | 80150 | ASRGL1 | 2 | + |
| CMS3 | 84189 | SLITRK6 | 3 | + |
| CMS3 | 84666 | RETNLB | 4 | + |
| CMS3 | 5937 | RBMS1 | 5 | − |
| CMS4 | 143903 | LAYN | 1 | + |
| CMS4 | 23414 | ZFPM2 | 2 | + |
| CMS4 | 11037 | STON1 | 3 | + |
| CMS4 | 27295 | PDLIM3 | 4 | + |
| CMS4 | 165 | AEBP1 | 5 | + |

As outlined above, candidate genes were assessed in both the Affymetrix training set and the COAD training set to avoid biasing the selection to a single training set or assay technology. After extending the risk scores from Affymetrix training set to Affymetrix validation set and the COAD training set to COAD validation set, as described herein, the CMS scores were defined for the entire Affymetrix and COAD data sets. The following method of derivation provides a more detailed disclosure of the CMS determination process:

1. Let X denote the set of all risk scores in Cohort A training set for all Affymetrix hgu133plus2 probes that are annotated to an Entrez ID, and have an equivalent risk score in the COAD training set.
2. Rank order the risk scores in X by the p-value of a linear model having response variable the risk score and covariate an indicator for CMS1.
3. Let Y be the top 25 ranked risk scores in X.
4. Let Z be the risk scores in the COAD training set that are equivalent to the scores in Y, and rank these by linear dependence with CMS1 membership in the COAD training set.
5. Re-order both Y and Z by the means of the rankings from the two training sets.
6. Form a candidate multigene score, S5, as the mean of the 5 highest ranked multistate scores for each sample in the Affymetrix and COAD training sets.
7. Define S7, S10 and S12 using the top ranked 7, 10 or 12 genes.
8. Using the scores as predictors of membership in CMS1, the AUC values for S5, S7, S10, S12 are 0.955, 0.955, 0.960, 0.955 in the Affymetrix training set, and 0.868, 0.873, 0.877, 0.870 in the COAD training set.
9. Given that the values of S5 are near the maxima for both training sets, this 5-gene score will be selected as CMS1 pre-score.

The above method of derivation was repeated for CMS2-4. For each subset, the 5-gene score was found to be optimal.

Data Processing for Classification into Subtypes Using the CMS Scores

Illustratively, a sample will be classified into that subtype whose score predicts subtype membership with the highest probability. Based on this assumption, in the algorithm we addressed the issues (1) for none of the subtypes is the score high enough to justify classification to that subtype, and (2) two or more scores predict subtype membership with high probability. Probabilities for subtype membership, and possible thresholds were defined using the Affymetrix training set. From among these candidates, we selected the classification algorithm that yielded the maximal mean balanced accuracy for all CMS subtypes in the Affymetrix and COAD training sets, and successfully classified at least 80% of samples. Balanced accuracies were only computed for samples classified into CMS1-4 by both the inventive system and the CRCSC system.

For each CMS subtype pre-score, compute the subtype's CMS score in the Affymetrix training set using the CRCSC CMS subtypes. The CMS score value for a sample x in the COAD cohort and the validation sets was defined by identifying the sample y in the Affymetrix training set whose subtype pre-score is closest to that of x, and assigning to x the CMS score value of y.

Candidates for a baseline threshold of a CMS score, for example the CMS1 score, under which we would not classify a sample into CMS1, were selected as follows. Let m be the number of samples in the CRCSC CMS1 subtype in the Affymetrix training set. For a number e≥1, let $b_e$ be the value of the CMS1 score so that e*m samples in the Affymetrix training set have CMS1 score≥$b_e$. In the classification algorithm, a sample will not be classified into CMS1 if the CMS1 score is <$b_e$. As candidates for baseline thresholds, identify b e values for e=1.10, 1.15, 1.20, 1.25, 1.30, for each CMS subtype.

For the subtype CMS scores and candidate baseline thresholds described above, we evaluated possible CMS classification protocol (or decision tree classifiers protocol) using the mean balanced accuracies in predicting the CRCSC CMS subtypes for all subtypes in both the Affymetrix and COAD training sets. In selecting between classifiers with similar mean balanced accuracies we gave priority to one with a greater percentage of classified samples. The choice of baseline threshold of the classifier with maximal mean balanced accuracy was e×1.25. The steps defining a preferred CMS classification protocol (classifier) is as follows, in order:
1. Given a sample x in the cohort, compute the subtype PPV-score values for x, for all CMS subtypes;
2. If none of the CMS score values of x are greater than the (respective) baseline threshold, then x is classified as mixed subtype (or unclassified subtype);
3. If for only one of the CMS scores is the value of x above the (respective) baseline threshold, then classify x into the subtype for that CMS score;
4. If the CMS scores of x for both CMS2 and CMS4 are above the (respective) baseline thresholds and the CMS score of x for CMS1 is below the (respective) baseline threshold, classify x into CMS4;
5. If the CMS scores of x for both CMS1 and CMS4 are above the (respective) baseline thresholds, classify x into CMS1;
6. If none of 1-5 apply, then classify x into the subtype whose CMS score is maximal.

Thus, if the CMS score of x for CMS1 is the highest score above its threshold (i.e., above its baseline threshold and is maximal), x is always classified into CMS1, regardless of the CMS scores of x for any other CMS2-4. On the contrary, if the CMS score of x for CMS2 is the highest score above its threshold, x is not necessarily CMS2—because if, for example, the CMS score of x for CMS4 is also above its threshold (and the CMS score of x for CMS1 is below its threshold), x is classified as CMS4 even though the CMS score of x for CMS4 is below the CMS score of x for CMS2. However, just because the CMS score of x for CMS1 is above its threshold does not mean that x is automatically classified as CMS1. If, for example, the respective the CMS scores of x for CMS2 and/or CMS3 are above their thresholds and above the CMS score of x for CMS 1 (and the CMS score of x for CMS4 is below its threshold), x would be classified with the higher of CMS2 and CMS3. But, if the CMS score of x for CMS4 is also above its threshold, x is instead classified as CMS1, even though it is not the highest score.

Accordingly, certain embodiments of the present disclosure can include a step (or process) of applying a CMS classification protocol to determine the CMS of a colorectal cancer based on a plurality of CMS scores (e.g., subtype CMS score values for the colorectal cancer, for all four CMS subtypes), as follows:
(ix) classifying the colorectal cancer with a CMS determination of CMS1 when the first CMS score (for CMS1) and the fourth CMS score (for CMS4) are each above respective predictive thresholds;
(x) classifying the colorectal cancer with a CMS determination of CMS4 when the second CMS score (for CMS2) and the fourth CMS score (for CMS4) are each above respective predictive thresholds and when (i) does not apply;
(xi) selecting from among the first, second, third, and fourth CMS scores (for CMS1, CMS2, CMS3, and CMS4, respectively) a maximal CMS score and classifying the colorectal cancer with a CMS determination selected from the group consisting of CMS1, CMS2, CMS3, and CMS4 based on the maximal CMS score or corresponding to the CMS of the maximal CMS score when the maximal CMS score is above the predictive threshold and when neither (i) nor (ii) applies;
(xii) classifying the colorectal cancer with a CMS determination of mixed subtype or unclassified subtype when the first, second, third, and fourth CMS scores (for CMS1, CMS2, CMS3, and CMS4, respectively) are each below the predictive threshold.

Table 4 presents CMS subtypes predicted by the inventive classifier/methodology compared to the CRCSC CMS subtypes in confusion matrices for the Affymetrix and COAD training sets, including the sensitivity, specificity and balanced accuracies.

TABLE 4

| Classifier | Affymetrix training CRCSC subtypes | | | | | COAD training CRCSC subtypes | | | | |
| --- | --- | --- | --- | --- | --- | --- | --- | --- | --- | --- |
| Subtype | CMS1 | CMS2 | CMS3 | CMS4 | NONE | CMS1 | CMS2 | CMS3 | CMS4 | NONE |
| CMS1 | 101 | 0 | 6 | 12 | 5 | 24 | 1 | 3 | 6 | 4 |
| CMS2 | 3 | 235 | 9 | 8 | 19 | 1 | 53 | 1 | 1 | 7 |
| CMS3 | 1 | 2 | 59 | 1 | 6 | 1 | 2 | 17 | 0 | 0 |
| CMS4 | 2 | 21 | 1 | 112 | 5 | 2 | 2 | 1 | 37 | 6 |
| NONE | 10 | 23 | 6 | 8 | 28 | 4 | 6 | 4 | 1 | 5 |
| sensitivity* | 0.94 | 0.90 | 0.89 | 0.84 | | 0.86 | 0.91 | 0.77 | 0.84 | |
| specificity* | 0.96 | 0.96 | 0.98 | 0.96 | | 0.92 | 0.97 | 0.98 | 0.95 | |
| balanced accuracy* | 0.95 | 0.93 | 0.94 | 0.89 | | 0.89 | 0.94 | 0.87 | 0.90 | |

*Samples unclassified by either classifier, labelled NONE, were excluded in calculating these statistics.

Figure 1B:
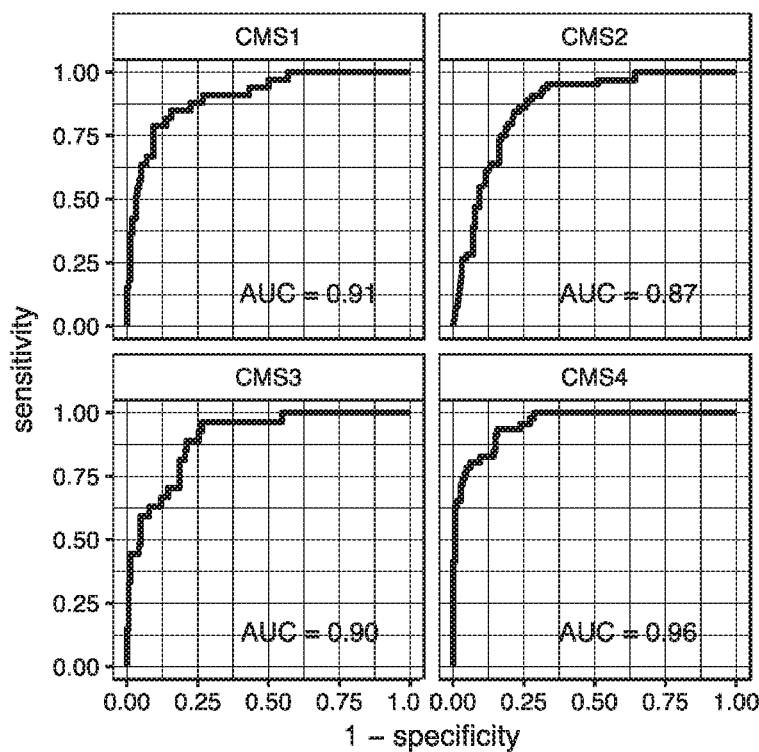

Validation of CMS Classification Method in Affymetrix and COAD Validation Cohorts, and READ The significance of each CMS score defined above was validated as a predictor of CRCSC CMS subtype membership with receiver operator characteristic (ROC) plots and area under the curve (AETC) values in the Affymetrix validation set and COAD validation set FIGS. 1A-1B illustrate receiver operator characteristic (ROC) curves for (A) the Affymetrix validation set, and (B) the COAD validation set. Each panel plots the ROC curve for predicting membership in the CRCSC CMS subtype with the corresponding inventive CMS score. Area under the curve (AETC) values assess the accuracy of the prediction; values closer to 1 indicate greater accuracy. Because all AETC values were at least 0.87, this was evidence that the CMS scores were strong predictors of CMS subtype membership in these cohorts.

The inventive CMS classifier, defined above, classified 85% and 86% of samples into CMS subtypes in the Affymetrix validation set and COAD validation set, respectively. In comparison, CRCSC classified 89 and 88% into a CMS subtype in these cohorts. Table 5 presents CMS subtypes predicted by the inventive CMS classifier compared to the CRCSC CMS subtypes in confusion matrices for the Affymetrix and COAD validation sets, including the sensitivity, specificity and balanced accuracies. Agreement of the inventive CMS predicted subtypes with CRCSC subtypes exhibited balanced accuracies for CMS1-4 of 0.90. 0.91, 0.91, 0.88 in Affymetrix validation set, and 0.92, 0.94, 0.83, 0.87 in the COAD validation set. The overall prediction of CMS subtype by the inventive CMS classifier was statistically significant in Affymetrix validation set [overall accuracy 0.85 (95% CI 0.83-0.87), no information rate 0.42, p-value<$2.0 \times 10^{-16}$] and COAD validation set[overall accuracy 0.86 (95% CI 0.80-0.91), no information rate 0.38, p-value<$2.0 \times 10^{-16}$].

CMS Classifier/Methodology Predicts CMS in Samples for the PETACC3 Clinical Trial Tissue samples from patients in the PETACC3 clinical trial were stored using formalin-fixed paraffin-embedded (FFPE) methodology. Previously, mRNA was extracted from a set of samples from PETACC3 patients (Cohort C, n=688) and hybridized to an Almac customized Affymetrix microarray platform. To facilitate the translation of the CMS classifier/methodology to this platform, Cohort C was partitioned to a training set (n=342) and validation set (n=346).

Typical of Affymetrix based microarray platforms, many genes are represented by multiple array probes. Thus, executing the CMS classifier algorithm for Cohort C, required selecting, for each of the 20 genes in the preferred CMS classifier panel, a representative probe. To do so, for each CMS classifier panel gene we selected the probe whose risk score in the Cohort C training set was most significantly predictive of the corresponding CRCSC-CMS subtype.

Having selected probes for the CMS classifier panel genes, the CMS scores for each of CMS 1-4 were computed for Cohort C training set from probe risk scores as for the Affymetrix training set. The CMS scores were then computed for the Cohort C validation set using the Cohort C training set as a reference set.

The AETC values for the CMS scores for CMS 1-4 in the Cohort C validation set were 0.78, 0.83, 0.92, 0.87, respectively. The subsequent classification of samples in CMS subtypes using the scores agreed with CRCSC-CMS subtypes with accuracy 0.81 and balanced accuracies 0.76, 0.88, 0.93, 0.86 for CMS1-4, respectively. This result shows that CMS classifier can be executed using FFPE tissue samples.

CMS Classifier/Methodology Predicts Response to Cetuximab Therapy

Some embodiments include determining and/or administering a treatment protocol based at least in part on the CMS classification determined with embodiments of the present

TABLE 5

|  | Affymetrix validation (n = 1205) CRCSC subtypes | | | | | COAD validation (n = 193) CRCSC subtypes | | | | |
| --- | --- | --- | --- | --- | --- | --- | --- | --- | --- | --- |
|  | CMS1 | CMS2 | CMS3 | CMS4 | NONE | CMS1 | CMS2 | CMS3 | CMS4 | NONE |
| CMS1 | 124 | 9 | 17 | 27 | 20 | 22 | 0 | 2 | 4 | 1 |
| CMS2 | 1 | 329 | 2 | 17 | 21 | 0 | 59 | 4 | 5 | 6 |
| CMS3 | 6 | 20 | 112 | 2 | 22 | 3 | 0 | 13 | 1 | 5 |
| CMS4 | 12 | 22 | 1 | 212 | 27 | 0 | 1 | 0 | 31 | 1 |
| NONE | 27 | 62 | 40 | 25 | 48 | 8 | 4 | 8 | 5 | 10 |
| sensitivity* | 0.87 | 0.87 | 0.85 | 0.82 |  | 0.88 | 0.98 | 0.68 | 0.76 |  |
| specificity* | 0.93 | 0.96 | 0.96 | 0.95 |  | 0.95 | 0.89 | 0.97 | 0.99 |  |
| balanced accuracy* | 0.90 | 0.91 | 0.91 | 0.88 |  | 0.92 | 0.94 | 0.83 | 0.87 |  |

*Samples unclassified by either classifier, labelled NONE, were excluded in calculating these statistics.

The distributions of CRCSC CMS 1-4 subtypes in the READ rectal cancer cohort were 3%, 46%, 13%, 29%, respectively. These differences compared to colon cancer are to be expected because the CMS1 tumors are largely proximal, and CMS2 tumors are largely distal. The CMS classifier scores were computed for the READ rectal cancer cohort using the COAD training set as a reference set of samples, and the inventive CMS classification was computed with the same thresholds as for COAD. The inventive CMS classifier/methodology exhibits significant agreement with CRCSC CMS classification [overall accuracy 0.83 (95% CI 0.75-0.90), no information rate 0.51, p-value=$1.4 \times 10^{-12}$] and balanced accuracies for CMS1-4, 0.76, 0.85, 0.95, 0.87, respectively.

disclosure. Illustratively, some embodiments include using the CMS classifier scores to predict differential response to cetuximab among CMS subtypes in colorectal cancer metastases. Specifically, the role of CMS signature scores was assessed in colorectal cancer metastasis samples (GSE5851, n=68, Affymetrix microarray) in predicting response to cetuximab. Progression-free survival (PFS) was the primary endpoint. The predictive significance of CMS classifier scores relative to KRAS mutation status was also studied using multivariate Cox proportional hazards models.

Cetuximab is a monoclonal antibody that inhibits activity of the gene EGFR. Based on the results of multiple clinical trials, the NCCN supports treatment with cetuximab for metastatic colorectal cancer patients with wild-type KRAS gene (www(dot)nccn(dot)org/professionals/physician_gls/pdf/col.on(dot)pdf). Subset analysis of the clinical trials reported above suggest that colon cancers are heterogeneous in their responsiveness to cetuximab. Thus, physicians need a diagnostic test that separates the patients likely to respond to cetuximab from those who are likely resistant to cetuximab. Embodiments of the present invention meet this need and solve this problem in the art, as described in further detail below, by providing a CMS classifier score that is predictive of positive response to cetuximab for patients with metastatic colon cancer, and for cetuximab resistance.

The cohort analyzed here (GSE5851) consisted of 80 colon cancer metastases hybridized to hgu133a Affymetrix microarrays. Clinical characteristics of the patients, 68 of which were treated with cetuximab, are found in Table 6 (Traits of GSE5851).

TABLE 6

| TRAIT | n |
|---|---|
| biopsy tissue (liver/other) | 61/19 |
| KRAS status (mutated/WT/NA) | 27/43/10 |
| response to cetuximab (CR/PR/SD/PD/UTD) | 1/5/19/43/12 |

The CMS classifier scores can be computed precisely for datasets based on Affymetrix hgu133plus2 arrays, RNA-seq and/or some other platforms. However, some of the hgu133plus2 probes used to compute the CMS classifier scores are missing from the hgu133a platform. For that reason, we computed approximations to the CMS classifier scores using the expression values of the hgu133a probes in the Affymetrix training set as follows.

ETsing the risk scores for panel genes represented by probes in hgu133a, we first computed l33a-pre-scores for each CMS subtype in the Affymetrix training set as the mean of the relevant risk scores. Because CMS classifier scores were defined for each sample in the Affymetrix training set, each l33a-pre-score value approximates CMS classifier score values through these samples. To create a smooth, steadily increasing approximation, we fit a loess smooth curve with response variable CMS classifier score and covariate l33a-pre-scores for the Affymetrix training set. This smooth curve is defined to be the CMS score-l33a approximated through the hgu133a panel genes. One such score exists for each of CMS1-4. The root mean square error of the ability of the CMS score-l33a to approximate the CMS classifier score, for each of CMS1-4 were CMS1: 0.07, CMS2: 0.03, CMS3: 0.12, CMS4: 0.04, showing that these approximations were sufficiently close so that tests of treatment response with respect to each were likely to yield comparable results.

For each sample s in GSE5851 and each CMS subtype, the CMS score-l33a for a was computed by finding the sample t in the Affymetrix Training set with the pre-score-l33a closest to the pre-score-l33a of s; then the CMS score-l33a of t was the score value for S. Using the CMS classifier scores, the CMS subtypes, CMS1-4 were defined as they were for Affymetrix training and validation cohorts.

The ability of the CMS classifier scores to predict responsiveness to cetuximab treatment was tested with Cox proportional hazards survival models with days of progression-free survival as endpoint. We found that the CMS2 score-l33a was significantly predictive of a positive response to cetuximab with p-value $9 \times 10^{-5}$ is the GSE5851 samples treated with cetuximab (n=68), and predictive with p-value 0.02 in those treated samples with wild type KRAS (n=39). None of the other CMS scores were significantly predictive of response or resistance using progression-free survival as endpoint.

Responsiveness to cetuximab were also reported in discrete categories, CR=complete response, PR=partial response, SD=stable disease, PD=progressive disease. The CMS1 subtype defined by the CMS classifier/methodology was distinguished in that all 8 samples in the subtype had progressive disease, indicating likely resistance to cetuximab in this subtype.

Thus, the CMS2 score was predictive of positive response to cetuximab in a cohort (GSE5851) of samples from patients with metastatic colon cancer and samples in the CMS1 subtype defined by the CMS classifier/methodology were resistant to cetuximab. CMS classifier/methodology predicts response to FOLFIRI treatment The most frequently used chemotherapy regimen for treating colorectal cancer is FOLFOX, a combination of leucovorin calcium (folinic acid), fluorouracil, and oxaliplatin. An alternative regimen is FOLFIRI, a multidrug cocktail that replaces oxaliplatin with irinotecan. FOLFIRI may be used instead of FOLFOX, especially for metastatic patients. In the overall population of colon cancer patients, FOLFOX is the standard of care. This choice is based on the PETACC-3 clinical trial, in which a random population of stage III colon cancer patients, those treated with FOLFIRI had comparable long-term expected relapse-free survival to those treated with FOLFOX. However, some subpopulations of colon cancer patients appear to be resistant to FOLFOX, in particular, the mesenchymal CMS4 subtype.

Embodiments of the present disclosure were able to determine, in two independent cohorts, CMS4 patients that were highly responsive to FOLFIRI.

Affymetrix hgu133plus 2 microarray data (Cohort F) from colorectal cancer tumors (primary and metastatic) treated with FOLFIRI were obtained from GSE72970 and GSE62080 (n=106). Each patient has been classified as a "responder" or a "non-responder" based on the rate of progression of the disease following treatment.

To discover hypotheses of the relationship between the inventive CMS scores and FOLFIRI responsiveness, we use Cohort G (n=239), derived from samples in GSE14333 and GSE17536. Using a previously published signature predictive of FOLFIRI response, samples in Cohort G were classified as likely to be responsive or non-responsive to FOLFIRI.

The samples in Cohort G and Cohort F were normalized together using fRMA and ComBat to control for batch effects. Recall that samples in Cohort G were included in the Affymetrix training and validation sets, hence, the inventive CMS scores were previously defined for these samples. The inventive CMS scores were fit to all samples in this study using previously described methods with Cohort G as a reference set.

Cohort G was used to discover hypothetical dependencies of FOLFIRI response to the inventive CMS scores. We found that FOLFIRI response has the strongest dependence on CMS4 score ($p < 2.2 \times 10^{-16}$). The best partition of samples by FOLFIRI response was as CMS4 score>0.4 (responsive) and CMS4 score≤0.4 (non-responsive). Adding other CMS scores in a multi-variable model did not improve on CMS4 score alone.

The CMS4 predictor of FOLFIRI response was verified in Cohort F. Patients in Cohort F with CMS4 score>0.4 were significantly ($p = 8.0 \times 10^{-4}$) more likely to be responsive to FOLFIRI (38 responders, 26 non-responders) than patients with CMS4 score≤0.4 (11 responders, 31 non-responders).

Thus, in the cohort of patients from GSE72970 and GSE62080 treated with FOLFIRI (n=106), patients with CMS4 score>0.4 are likely to respond positively to FOLFIRI and those with CMS4 score≤0.4 are likely to be resistant to FOLFIRI. Combining these results, supports the use of the CMS classifier to select colorectal cancer patients who are more likely to respond to FOLFIRI than to FOLFOX.

CMS and Risk Classifiers/Methodologies Identify High-Risk Stage II Colon Cancer Patients Responsive to Standard Chemotherapy Clinical trials such as QUASAR showed that stage II colon cancer patients treated with standard chemotherapy (5-Fu) did not have better outcomes than those who only received observation. Based on these results, the standard of care for stage IIA and IIB colon cancer patients is to not administer chemotherapy post-surgery, even though 15% of these patients are likely to relapse within five years. Analysis of sensitivity to 5-Fu by consensus molecular subtype showed that patients in CMS 1-3 may respond to 5-Fu, while those in CMS4 are likely resistant to the treatment. Because clinical trials like QUASAR could not segregate patients by CMS, this differential response was not identified.

Using the inventive CMS classifier/methodology, a stage IIA and IIB colon cancer patient can be diagnosed as CMS1-4, or Mixed. Patients classified or diagnosed with CMS4 colon cancer can be treated with FOLFIRI (based on an analysis of FOLFIRI sensitivity herein). For a patient not in CMS4 (i.e., CMS1-3, or Mixed subtype), the inventive Risk classifier can be used to identify the patient as at high risk of relapse, or low risk of relapse. If the patient is at high risk of relapse, then treatment with 5-Fu can be recommended and/or administered. If the patient is at low risk of relapse, then observation alone can be recommended and/or administered (e.g., after surgery). Thus, embodiments of the present disclosure can inform and/or dictate modification and/or confirmation of a particular treatment protocol based in CMS and/or Risk information not previously available to the physician and patient at clinic.

Additional Preferred Embodiments

Inspection of the p-value column in Table 3a, above, shows that many genes besides the preferred 5 genes are significantly predictive of the subtypes, suggesting that significant predictive scores for CMS subtypes could be defined with alternative sets of genes. This hypothesis is tested below, along with the evaluation of scores derived from sets of 2, 3, 7, or 10 genes, to establish the following assertions.

Analysis of the significance of scores as predictive of CMS subtypes derived from sets of genes establish the following assertions:
1. Scores derived from 2 or 3 of the top 25 genes are likely to be commercially viable but inferior to CMS classifier scores based on the preferred 5 genes;
2. Scores derived from 5 of the top 50 genes are likely to be commercially viable and all but the CMS2 score will be equivalent to CMS classifier scores based on the preferred 5 genes;
3. Scores derived from 5 of the top 100 genes are likely to be commercially viable but inferior to CMS classifier scores based on the preferred 5 genes;
4. Scores derived from 7 of the top 50 genes are likely to be equivalent to CMS classifier scores based on the preferred 5 genes;
5. Scores derived from 7 of the top 100 genes are likely to be commercially viable and all but the CMS2 score are likely to be equivalent to CMS classifier scores based on the preferred 5 genes;
6. Scores derived from 10 of the top 100 genes are likely to be equivalent to CMS classifier scores based on the preferred 5 genes;

Based on evaluations of CMS prediction tools in the literature, we considered a predictive score to be "commercially viable" if the AUC is at least 0.80. Based on the levels of significance of CMS classifier scores in validation sets, we considered a tool to be "equivalent to CMS classifier scores based on the preferred 5 genes" if the AUC is at least 0.88. Our assertions were tested by computing AUC values in the Affymetrix validation set.

Considering Item 3 above, e.g., it was impractical to test each of the 300 million possible 5-gene scores generated from the 400 genes in Table 3a. Instead, we estimated the significance of an arbitrary 5-gene score using probabilistic sampling, which states that the AUC of an arbitrary 5-gene score is effectively the same as the AUC of an arbitrary 5-gene score from a large subset of possible scores. For this study, we generated and analyzed a set of 500 randomly sampled scores. We further asserted that a predictive score was "likely" to be commercially viable if at least 0.70 of the 500 generated scores were commercially viable.

To test Item 3, e.g., we randomly sampled 500 5-gene sets from the top 100 genes in Table 3a for each of CMS1-4. We then computed the corresponding CMS1-4 scores, 500 each, and then the AUC values of the scores in the Affymetrix validation set. The predictive significance of an arbitrary such score was then assessed by computing the fraction of such AUC values that were above 0.80 (commercially viable) and above 0.88 (equivalent to CMS classifier scores based on the preferred 5 genes).

Simulations were carried out to assess the levels of significance of scores defined from 2, 3, 5, 7, 10 genes sampled from the top 10, 25, 50, 100 candidate genes, with results reported in Table 7. These results establish Items 1-6.

TABLE 7

| CMS subtype | Panel length | Ranks of genes | Probability >0.88 | Probability >0.80 |
|---|---|---|---|---|
| CMS1 | 2 | 1 to 10 | 0.26 | 0.69 |
| CMS2 | 2 | 1 to 10 | 0 | 1 |
| CMS3 | 2 | 1 to 10 | 0.4 | 1 |
| CMS4 | 2 | 1 to 10 | 1 | 1 |
| CMS1 | 2 | 1 to 25 | 0.18 | 0.76 |
| CMS2 | 2 | 1 to 25 | 0.03 | 0.98 |
| CMS3 | 2 | 1 to 25 | 0.35 | 0.98 |
| CMS4 | 2 | 1 to 25 | 1 | 1 |
| CMS1 | 3 | 1 to 10 | 0.4 | 0.87 |
| CMS2 | 3 | 1 to 10 | 0 | 1 |
| CMS3 | 3 | 1 to 10 | 0.81 | 1 |
| CMS4 | 3 | 1 to 10 | 1 | 1 |
| CMS1 | 3 | 1 to 25 | 0.4 | 0.93 |
| CMS2 | 3 | 1 to 25 | 0.11 | 1 |
| CMS3 | 3 | 1 to 25 | 0.62 | 1 |
| CMS4 | 3 | 1 to 25 | 1 | 1 |
| CMS1 | 5 | 1 to 25 | 0.68 | 0.99 |
| CMS2 | 5 | 1 to 25 | 0.3 | 1 |
| CMS3 | 5 | 1 to 25 | 0.87 | 1 |
| CMS4 | 5 | 1 to 25 | 1 | 1 |
| CMS1 | 5 | 1 to 50 | 0.82 | 1 |
| CMS2 | 5 | 1 to 50 | 0.49 | 1 |
| CMS3 | 5 | 1 to 50 | 0.75 | 1 |

TABLE 7-continued

| CMS subtype | Panel length | Ranks of genes | Probability >0.88 | Probability >0.80 |
|---|---|---|---|---|
| CMS4 | 5 | 1 to 50 | 1 | 1 |
| CMS1 | 5 | 1 to 100 | 0.83 | 1 |
| CMS2 | 5 | 1 to 100 | 0.36 | 1 |
| CMS3 | 5 | 1 to 100 | 0.71 | 1 |
| CMS4 | 5 | 1 to 100 | 1 | 1 |
| CMS1 | 7 | 1 to 50 | 0.89 | 1 |
| CMS2 | 7 | 1 to 50 | 0.7 | 1 |
| CMS3 | 7 | 1 to 50 | 0.94 | 1 |
| CMS4 | 7 | 1 to 50 | 1 | 1 |
| CMS1 | 7 | 1 to 100 | 0.94 | 1 |
| CMS2 | 7 | 1 to 100 | 0.66 | 1 |
| CMS3 | 7 | 1 to 100 | 0.88 | 1 |
| CMS4 | 7 | 1 to 100 | 1 | 1 |
| CMS1 | 10 | 1 to 100 | 0.99 | 1 |
| CMS2 | 10 | 1 to 100 | 0.89 | 1 |
| CMS3 | 10 | 1 to 100 | 0.95 | 1 |
| CMS4 | 10 | 1 to 100 | 1 | 1 |

Recurrence Risk

The purpose of the inventive Recurrence Risk classifier/methodology is to identify patients at high risk of relapse independent of the CMS subtype. In particular, the inventive classifier/methodology accomplishes this purpose using an identified subset of genes found to be highly prognostic for recurrence. The mean risk of relapse for CMS4 samples is higher than that of the other subtypes; i.e., the majority of CMS4 samples are poor prognosis. The inventive Recurrence Risk classifier/methodology was designed to identify poor prognosis samples that may not be in CMS4.

To identify genes for inclusion in the Risk classifier gene panel, we formed gene risk scores, as in the derivation of CMS classifier methodology. We ranked these genes by significance of predicting relapse in the CMS 1-3 training set using a Cox proportional hazards model with gene risk score as the sole variable.

An illustrative 75-gene panel for assessing risk of recurrence is presented in Table 8a, below. The direction column is "+" if risk of relapse increase with values of gene expression, and the direction column is "−" if risk of relapse decreases as values of gene expression increase.

TABLE 8a

| Symbol | p-value | Rank | Direction |
|---|---|---|---|
| GTSE1 | 6.95E-09 | 1 | − |
| TM4SF1 | 7.18E-07 | 2 | + |
| MYADM | 1.31E-05 | 3 | + |
| RAPGEF6 | 3.34E-05 | 4 | − |
| AHNAK2 | 4.26E-05 | 5 | + |
| PRPF38B | 4.66E-05 | 6 | + |
| RTN2 | 5.59E-05 | 7 | + |
| BLACAT1 | 6.16E-05 | 8 | + |
| ATP9A | 7.27E-05 | 9 | + |
| TMEM43 | 7.58E-05 | 10 | + |
| SERPINE1 | 8.13E-05 | 11 | + |
| SMARCC2 | 8.72E-05 | 12 | + |
| ZSCAN18 | 9.41E-05 | 13 | + |
| ARHGEF7 | 1.09E-04 | 14 | + |
| KNL1 | 1.11E-04 | 15 | − |
| SRGAP1 | 1.15E-04 | 16 | + |
| NUP37 | 1.27E-04 | 17 | − |
| SRSF5 | 1.31E-04 | 18 | + |
| CARMN | 1.45E-04 | 19 | + |
| RARG | 2.07E-04 | 20 | + |
| ESCO2 | 2.40E-04 | 21 | − |
| MPHOSPH9 | 2.71E-04 | 22 | − |
| PAPPA | 2.78E-04 | 23 | + |
| GUCY1A2 | 2.78E-04 | 24 | + |
| DHRS9 | 3.01E-04 | 25 | + |

TABLE 8a-continued

| Symbol | p-value | Rank | Direction |
|---|---|---|---|
| PNRC1 | 3.07E-04 | 26 | + |
| B3GNT7 | 3.28E-04 | 27 | + |
| ARHGEF10 | 3.32E-04 | 28 | + |
| CHEK1 | 3.32E-04 | 29 | − |
| RHBDD1 | 3.34E-04 | 30 | + |
| PSD4 | 3.53E-04 | 31 | + |
| SIN3B | 3.58E-04 | 32 | + |
| PLXNA3 | 3.96E-04 | 33 | + |
| KCNE4 | 4.00E-04 | 34 | + |
| TM2D1 | 4.14E-04 | 35 | + |
| TRAK1 | 4.17E-04 | 36 | + |
| GGT7 | 4.52E-04 | 37 | + |
| TMEM237 | 4.52E-04 | 38 | − |
| LAMB3 | 4.86E-04 | 39 | + |
| DIS3L2 | 5.01E-04 | 40 | − |
| RABL3 | 5.41E-04 | 41 | + |
| AMACR | 5.54E-04 | 42 | − |
| ABCC3 | 5.57E-04 | 43 | + |
| ATAD2B | 5.67E-04 | 44 | + |
| LARP7 | 5.67E-04 | 45 | + |
| SEC23B | 5.98E-04 | 46 | − |
| FAM3C | 6.56E-04 | 47 | + |
| NAA25 | 6.96E-04 | 48 | − |
| OBSL1 | 7.09E-04 | 49 | + |
| MUM1 | 7.26E-04 | 50 | + |
| HDAC9 | 7.63E-04 | 51 | − |
| PLXND1 | 7.64E-04 | 52 | + |
| FLT1 | 7.73E-04 | 53 | + |
| CALM1 | 7.84E-04 | 54 | + |
| FN1 | 7.97E-04 | 55 | + |
| KLK8 | 7.97E-04 | 56 | + |
| SREK1 | 8.00E-04 | 57 | − |
| DOCK6 | 8.12E-04 | 58 | + |
| RALGDS | 8.17E-04 | 59 | + |
| IDI1 | 8.31E-04 | 60 | + |
| TJP2 | 8.72E-04 | 61 | + |
| GABPB1-AS1 | 8.80E-04 | 62 | + |
| DDX11 | 9.04E-04 | 63 | + |
| ZNF107 | 9.32E-04 | 64 | − |
| SLC35D2 | 9.34E-04 | 65 | + |
| LINC00668 | 9.57E-04 | 66 | − |
| ATF7IP | 9.61E-04 | 67 | + |
| WDR36 | 9.84E-04 | 68 | − |
| APOL6 | 0.001063344 | 69 | − |
| DENR | 0.001075993 | 70 | − |
| SFXN4 | 0.001109455 | 71 | + |
| RAF1 | 0.001127751 | 72 | + |
| AP1G2 | 0.001127751 | 73 | + |
| SLC26A3 | 0.001127751 | 74 | + |
| TMEM144 | 0.001146234 | 75 | − |

Variables to include in the model were chosen from X, defined above to be the set of all risk scores in the Affymetrix training set for all Affymetrix hgu133plus2 probes that are annotated to an Entrez ID, and have an equivalent risk score in the COAD training set. For each element of X we computed a Cox proportional hazards model in the Affymetrix training set with endpoint 5-year relapse-free survival and risk score as the only variable. The elements of X were ordered by the p-values of these CPH models. Candidate prognostic scores P10, P15, P20, P25, P30 were defined as the mean values of the top 10, 15, 20, 25, or 30 risk scores in X, respectively. Using risk scores equivalent to the risk scores in X, we defined corresponding candidate prognostic scores in the COAD training set. After comparing the p-values of CPH models for these candidate prognostic models in both the Affymetrix and COAD training sets, we selected the 25-gene score as Recurrence Risk.

An illustrative 25-gene panel for assessing risk of recurrence is presented in Table 8b, below.

TABLE 8b

| symbol | ENTREZ ID | rank | values enriched by relapse cases |
|---|---|---|---|
| GTSE1 | 51512 | 1 | low |
| AHNAK2 | 113146 | 2 | high |
| MYADM | 91663 | 3 | high |
| TM4SF1 | 4071 | 4 | high |
| NUP37 | 79023 | 5 | low |
| FN1 | 2335 | 6 | high |
| PAPPA | 5069 | 7 | high |
| SERPINE1 | 5054 | 8 | high |
| CARMN | 728264 | 9 | high |
| RTN2 | 6253 | 10 | high |
| KCNE4 | 23704 | 11 | high |
| SRSF5 | 6430 | 12 | high |
| RAPGEF6 | 51735 | 13 | low |
| ATP9A | 10079 | 14 | high |
| CHEK1 | 1111 | 15 | low |
| PRPF38B | 55119 | 16 | high |
| LAMB3 | 3914 | 17 | high |
| GUCY1A2 | 2977 | 18 | high |
| BLACAT1 | 101669762 | 19 | high |
| TMEM237 | 65062 | 20 | low |
| MPHOSPH9 | 10198 | 21 | low |
| USP6NL | 9712 | 22 | low |
| TMEM43 | 79188 | 23 | high |
| ATP1A1-AS1 | 84852 | 24 | low |
| ARHGEF7 | 8874 | 25 | high |

Figure 2A:
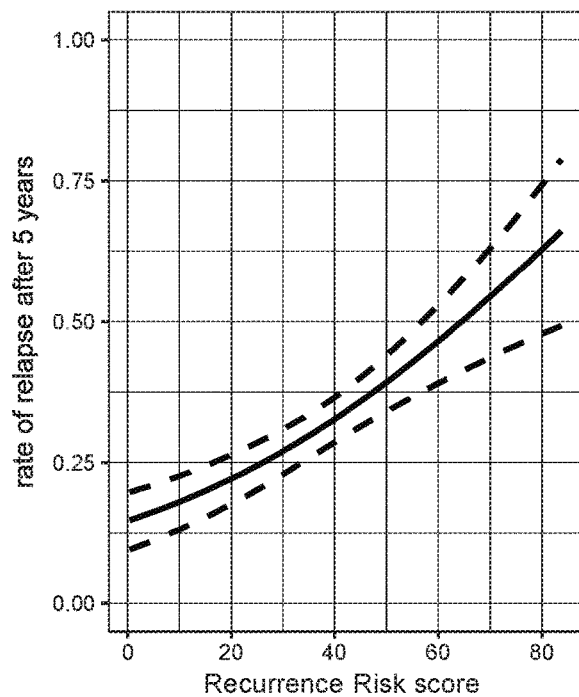
FIGS. 2A-2B illustrate the expected rate of relapse after 5 years for values of the Recurrence Risk score for (A) Cohort D validation set, and (B) Cohort B validation set.
Figure 2B:
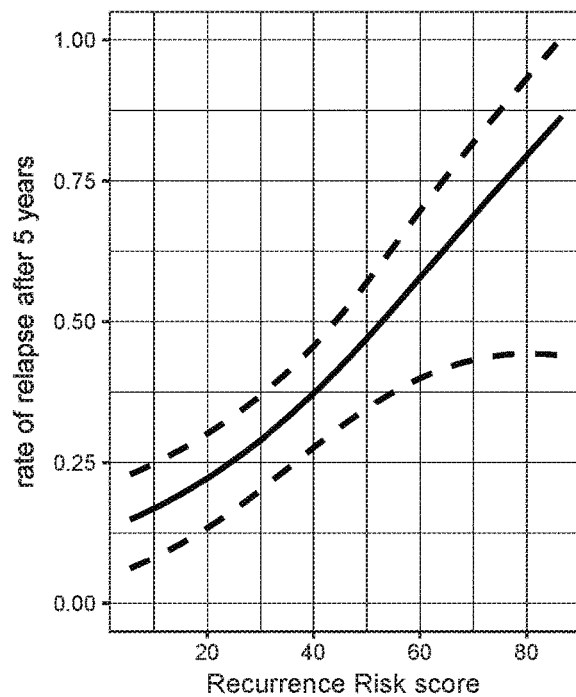

Validation of the Prognostic Significance of Recurrence Risk Classifier/Methodology, Independent of CMS Classification and Stage The inventive Risk classifier score was shown to be prognostic of 5-year relapse-free survival, assessed with the hazard ratio of Risk classifier score in increments of 50, in the Cohort D validation set [HR: 3.14 (95% CI 2.1-4.7); p=$1.0\times10^{-8}$] and COAT) validation set [HR: 4.7 (95% CI 2.3-9.5); p=$2.0\times10^{-5}$]. FIGS. 2A-2B illustrate the expected rate of relapse after 5 years for values of the Risk classifier score for (A) Cohort D validation set, and (B) Cohort B validation set. The Risk classifier score was significantly prognostic of relapse-free survival censored to 5 years in both Cohort D validation set [hazard ratio in increments of 50: 3.14 (95% CI 2.1-4.7); p=$1.0\times10^{-8}$] and Cohort B validation set [hazard ratio in increments of 50: 4.7 (95% CI 2.3-9.5); p=$2.0\times10^{-5}$]. The likelihood of relapse after 5 years increased steadily with Risk classifier score in both cohorts. Because of the similarity in prognostic significance between the two cohorts, subsequent analyses were performed in the pooled validation sets.

Figure 3A:
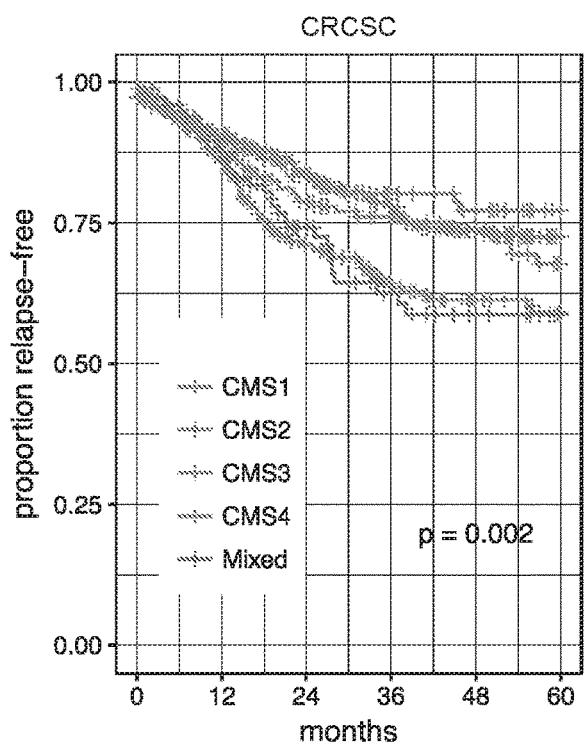
FIGS. 3A-3B illustrate Kaplan-Meier plots in the combined Cohort D and Cohort B validation sets for (A) CRCSC CMS classification, and (B) inventive CMS classification.
Figure 3B:
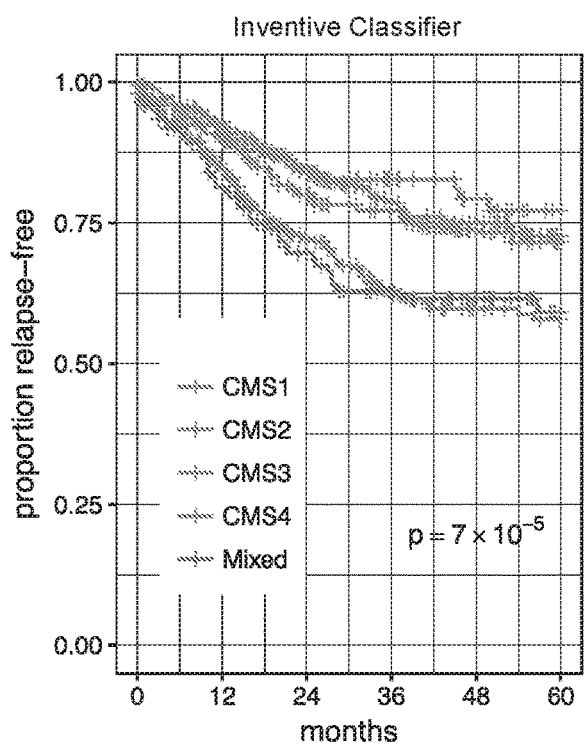

The CMS classification was also found to be prognostic of relapse-free survival, with CMS4 and the Mixed subgroups having poorer prognosis than the other subtypes in both the CRCSC (p=0.002) and inventive (p=$7.0\times10^{-5}$) CMS subtype systems/methodologies. FIGS. 3A-3B illustrate Kaplan-Meier plots in the combined Cohort D and Cohort B validation sets for (A) CRCSC CMS classification, and (B) inventive CMS classification. For the results in FIG. 3A, with respect to CRCSC CMS and selecting CMS1 for comparison, the hazard ratio of CMS4 to CMS1 is 1.44 (95% CI 0.98-2.1) and the hazard ratio of the Mixed subtype to CMS1 is 1.42 (95% CI 0.89-2.27). For the results in FIG. 3B, with respect to the CMS classifier, the hazard ratio of CMS4 to CMS1 is 1.66 (95% CI 1.1 1-2.48) and the hazard ratio of the Mixed subtype to CMS1 is 1.69 (95% CI 1.10-2.64). In both systems, the proportions relapse-free are comparable for CMS 1-3 and lower for CMS4 and Mixed.

The prognostic independence of the Recurrence Risk classifier from CMS subtype was tested in the following analyses. We showed that Risk classifier was prognostic independent of CMS subtype in the combined validation set; specifically, an additive multivariate Cox proportional hazard model with variables for CMS and Risk was more significant than a Cox proportional hazard model using only CMS (p-value of the difference in log-likelihoods=$2.1\times10^{-9}$).

Figure 4:
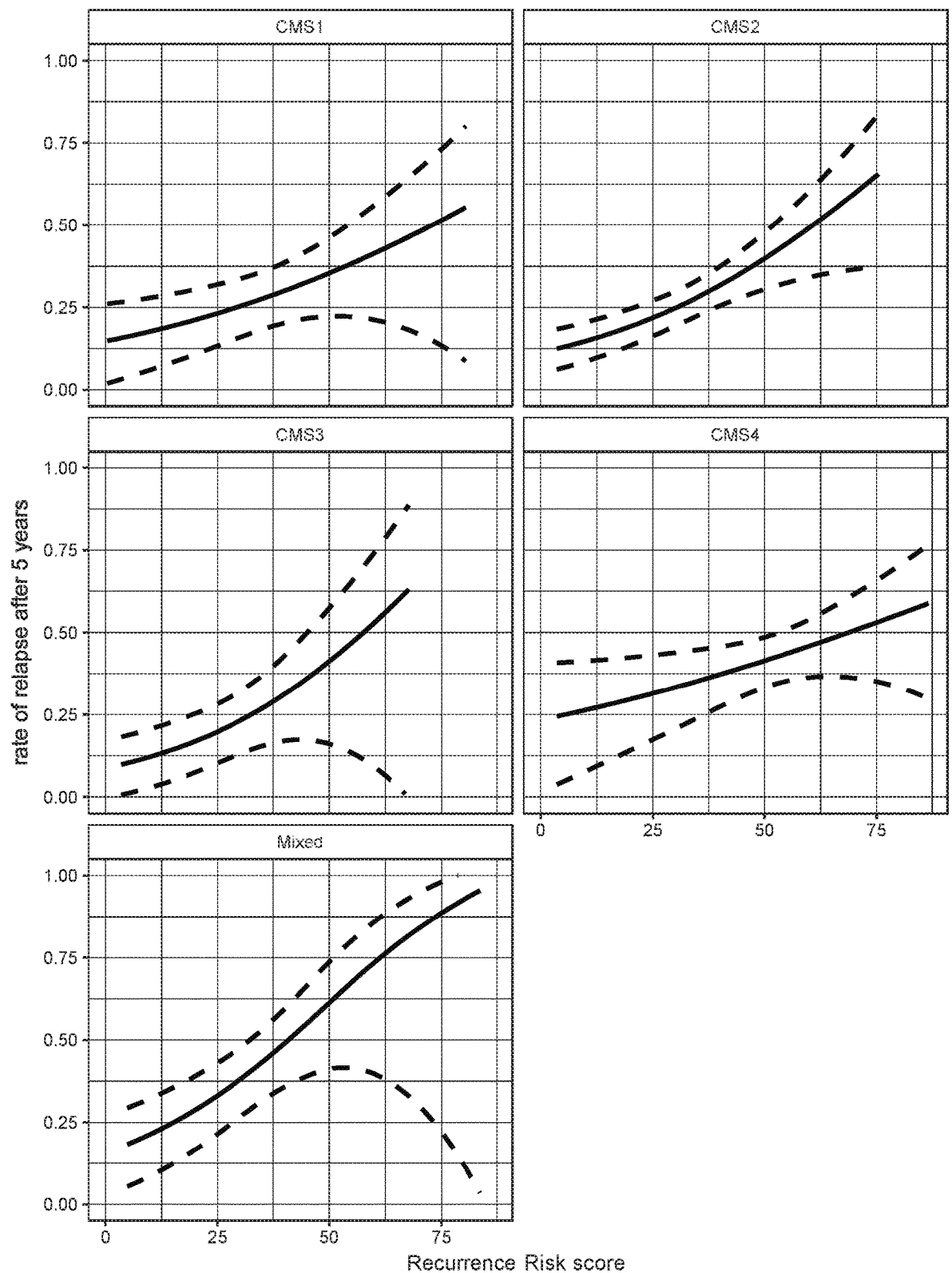
FIG. 4 illustrates the expected rate of relapse after 5 years for values of the Recurrence Risk score for the various inventive CMS subtype classification in the combined Cohort B and Cohort D validation sets (solid line) and 95% confidence intervals (dashed lines).

Moreover, the risk of relapse after 5 years increased steadily with Risk classifier score in each CMS subtype. FIGS. 4A-4B illustrate the expected rate of relapse after 5 years for values of the Risk classifier score for the CMS subtypes in the combined Cohort B and Cohort D validation sets (solid line) and 95% confidence intervals (dashed lines). Hazard ratios for the Risk classifier score in increments of 50 (95% CI) for CMS1-4, Mixed, were 2.75 (1.01-7.44), 4.23 (2.14-8.44), 5.82 (1.49-22.75), 2.00 (0.89-4.49), 5.58 (2.01-15.49), respectively. The hazard ratio for Risk in each subtype except CMS4 was significantly different from CMS1. Moreover, analyses of interaction effects showed that for none of the subtypes was the hazard ratio of Risk significantly different from that of CMS1 (p-values for comparisons to CMS2-4, Mixed, were 0.5, 0.4, 0.6, 0.3, respectively). These analyses showed that the Risk classifier offered significant prognostic information for each subtype in the combined validation set.

Figure 5:
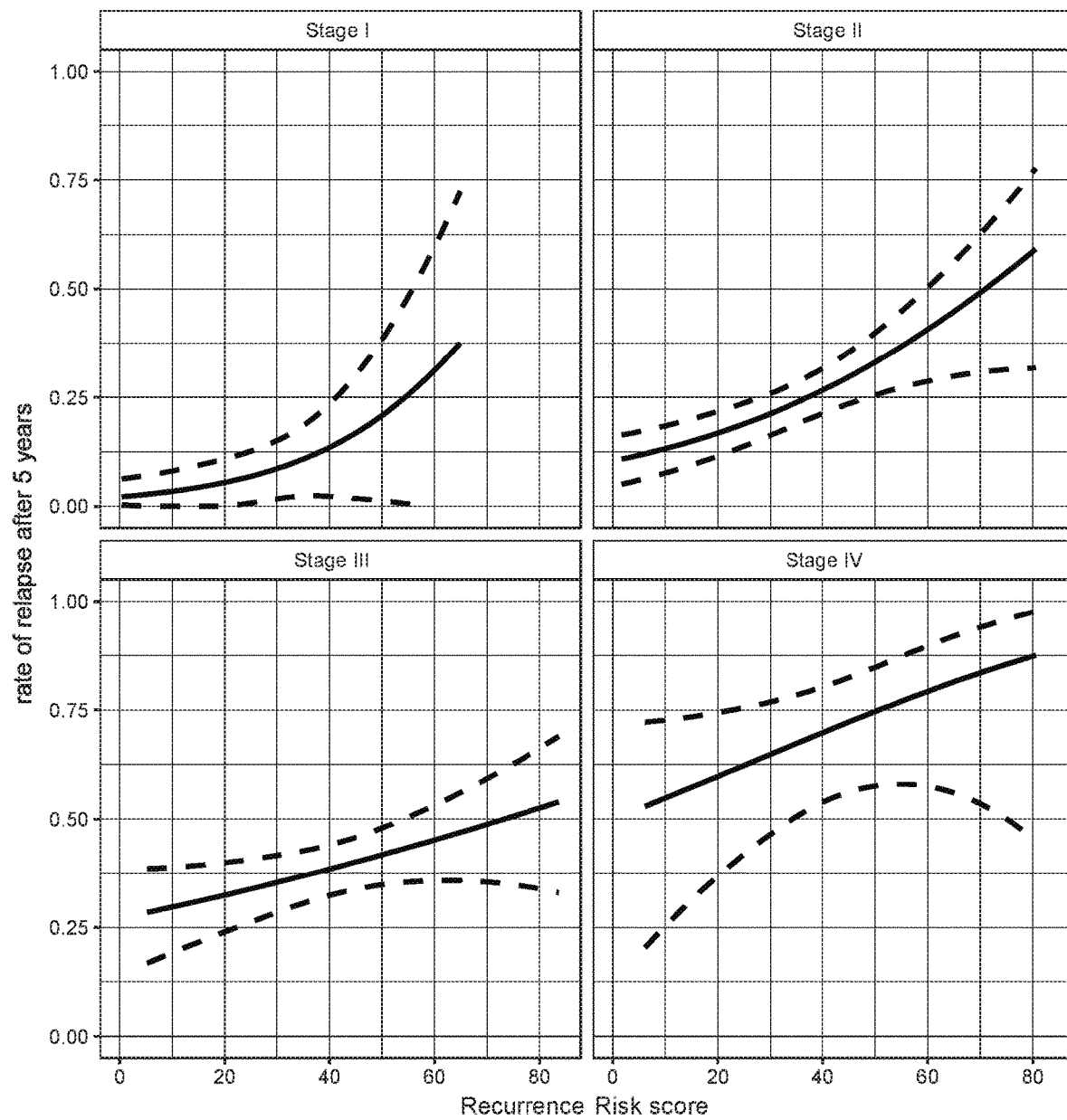
FIG. 5 illustrates the expected rate of relapse after 5 years for values of the Recurrence Risk score for stage I-IV in the combined Cohort B and Cohort D validation sets (solid line) and 95% confidence intervals (dashed lines).

Similar analyses were used to test the prognostic independence of Risk score from tumor stage. Stage was a significant risk factor in the combined validation set (p<$10^{-16}$). An additive Cox proportional hazard model with variables for Risk and stage was significantly more significant than a Cox proportional hazard model with stage alone (p-value of the difference in log-likelihoods=$1.6\times10^{-6}$). Using an additive Cox proportional hazard model, we also showed that Risk classifier score adds significantly to the prognostic information provided by the combination of CMS classification and stage. Restricted to each stage, the risk of relapse increases with Risk classifier score. FIG. 5 illustrates the expected rate of relapse after 5 years for values of the Risk classifier score for stage I-IV in the combined Cohort B and Cohort D validation sets (solid line) and 95% confidence intervals (dashed lines). Hazard ratios for the Risk classifier score in increments of 50 (95% CI) for stage I-IV, were 10.73 (0.92-124.9), 3.68 (1.93-7.03), 1.71 (1.01-2.90), 1.98 (0.88-4.46), respectively. Risk classifier score was most significant in stage II tumors [logrank score test p-value=$7.0\times10^{-5}$, HR 3.68 (95% CI 1.93-7.02)].

Stratification of Risk Score in Stage II and Stage III Tumors

Because, at a basic level, a chemotherapy treatment decision is binary—i.e., treat or do not treat—a partition of patients by thresholds of Risk score are useful for exploring the potential impact of such a decision. Determining the optimal thresholds for different subgroups of patients or possible treatment decisions may require further analysis. Standards of care are observation following surgery for stage II patients, with T-stage<4, and chemotherapy for stage III patients. The inventive Recurrence Risk classifier/methodology can also identify poor prognosis stage II patients who may benefit from (adjuvant) chemotherapy, and very good prognosis stage III patients who may not receive a significant added benefit from chemotherapy. To explore the Risk classifier features that may inform such decisions, we partition stage II patients in Cohorts B and D at Risk=41, the boundary between the second and third tertiles, and we partition stage III patients in Cohorts B and D at Risk=23, the boundary between the first and second tertiles.

Figure 6A:
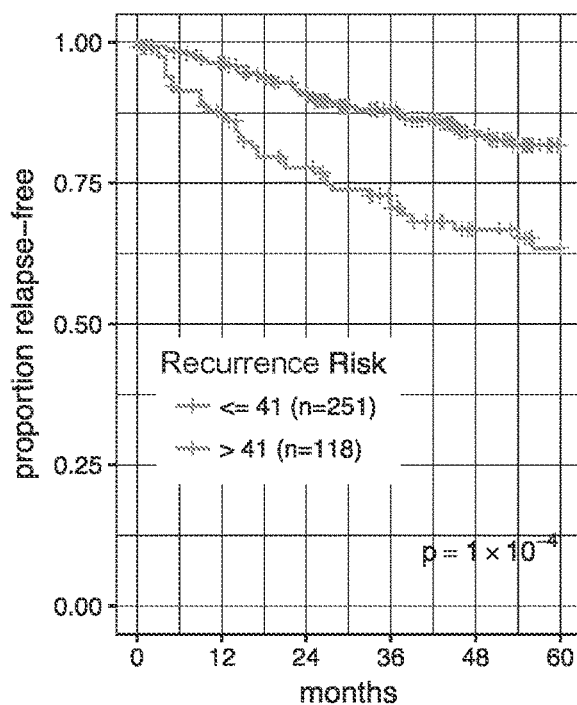
FIGS. 6A-6B illustrate Kaplan-Meier plots in the combined Cohort B and Cohort D validation sets for (A) stage II patients stratified as Recurrence Risk≤41 or Recurrence Risk>41, or (B) stage III patients stratified as Recurrence Risk≤23 or Recurrence Risk>23.
Figure 6B:
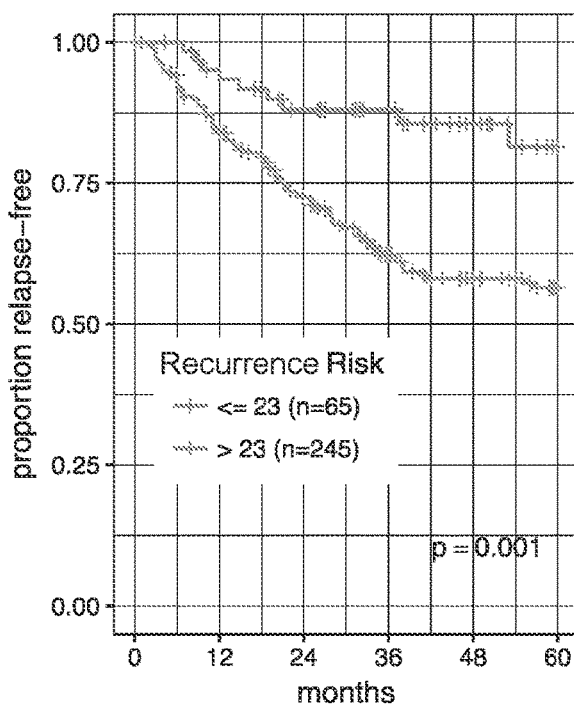

FIGS. 6A-6B illustrate Kaplan-Meier plots in the combined Cohort B and Cohort D validation sets for (A) stage II patients stratified as Risk≤41 or Risk>41, or (B) stage III patients stratified as Risk≤23 or Risk>23. The thresholds were the boundaries between tertiles for the Risk classifier. Expected relapse-free survival after 5 years (95% CI) was 0.82 (0.76-0.88), 0.64 (0.54-0.74) in stage II for low-risk and poor-risk strata, respectively, and 0.82 (0.70-0.94), 0.56 (0.50-0.64) in stage III for low-risk and poor-risk strata, respectively.

Figure 7A:
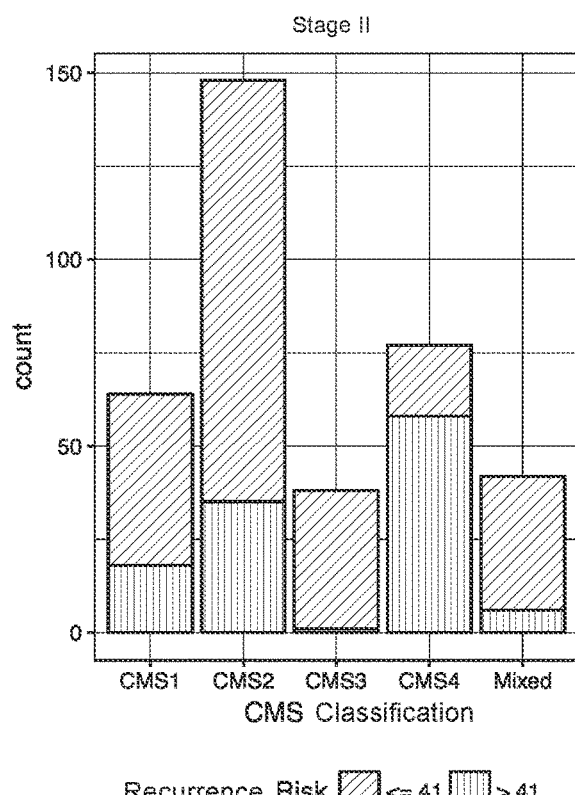
FIGS. 7A-7B illustrate the distribution of risk strata in CMS subtypes in the combined Cohort B and Cohort D validation sets in (A) stage II, and (B) stage III.
Figure 7B:
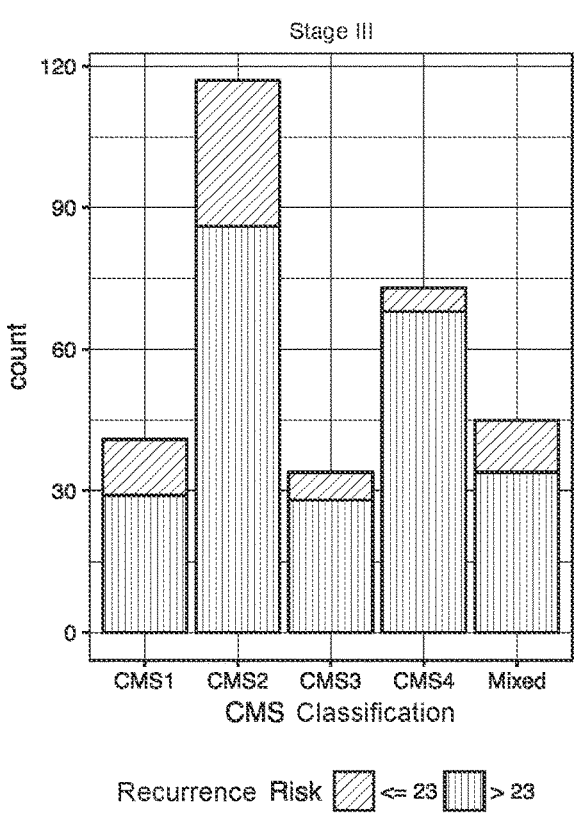

The Risk classifier/methodology stratification was significantly prognostic in the stage II subgroup of combined Cohort B and Cohort D validation sets (see FIG. 6A, for which the hazard ratio is 2.41 (95% CI 1.52-3.81), p=1.0× $10^{-4}$). Similarly, the alternative Risk stratification was significantly prognostic in the stage III subgroup of the validation sets (see FIG. 6A, for which the hazard ratio is 2.99 (95/CI 1.51-5.92), p=0.001). Reflecting the independence of Risk and CMS, these risk strata were distributed across the CMS subtypes. FIGS. 7A-7B illustrate the distribution of risk strata in CMS classifier subtypes in the combined Cohort B and Cohort D validation sets in (A) stage II, and (B) stage III. While a disproportionate number of the poor prognosis stage II patients are in CMS4, the Risk classifier stratification is also significantly prognostic in the stage II patients not in CMS4 in the combined validation sets [hazard ratio 2.72 (95% CI 1.54-4.80), p=3.0×$10^4$]. Similarly, the alternative Risk classifier stratification was significantly prognostic in the stage II patients not in CMS4 in the combined validation sets [hazard ratio 3.07 (95% CI 1.47-6.39), p=0.002].

Stage II patients with high Risk classifier score>41, with estimated proportion relapse-free after 5 years 0.64 (95% CI 0.54-0.74), may be candidates for more aggressive therapy. Following appropriate clinical studies, this risk assessment, optionally combined with CMS classifier subtyping, can help physicians to better personalize treatment, avoid unnecessary exposure to chemotherapeutics, improve patient outcomes, and reduce healthcare costs.

Alternative Embodiments

In some embodiments of the present disclosure, a suitable number of genes that are statistically predictive (or prognostic) of colorectal cancer recurrence can be included in a group of representative genetic elements, from which a smaller number of representative genes can be selected for analysis. Based on the gene expression level (e.g., as measured through RNA quantification) of each of the representative genes from the group of genetic elements, a prognostic score representative of a probability that the colorectal cancer will recur can be determined. For example, in at least one embodiment, the 50 highest ranking genes (e.g., by p-value analysis), that are statistically predictive of relapse can be included in the group of genes. The expression level of 15 of these 50 genes can be determined and used to calculate a prognostic score representative of a probability that the colorectal cancer will recur.

Alternatively, the 20 highest ranking genes, 25 highest ranking genes, 30 highest ranking genes, 35 highest ranking genes, 40 highest ranking genes, 45 highest ranking genes, 60 highest ranking genes, 70 highest ranking genes, 80 highest ranking genes, and so forth, that are statistically predictive of relapse can be included in the group of genes. In certain embodiments, any suitable number of genes between the 15 highest ranking genes about 75 highest ranking genes that are statistically predictive of relapse can be included in the group of genes. It will again be appreciated that the highest-ranking genes need not always be included in the group of genes or selected from the group of genes during Risk classification.

Moreover, any suitable number of representative genes, out of or from the group of genes, can be selected for analysis. For example, at least 10 genes, 15 genes, 20 genes, 25 genes, etc., from the group of genes can be selected for analysis. The respective expression levels of these at least 10, etc., representative genes (or the RNA transcripts thereof) can be determined and used to calculate the prognostic score representative of a probability that the colorectal cancer will recur. Thus, the Risk classifier methodology can include determining, based on the expression level of each of the at least 10, etc. RNA transcripts from a group of genetic elements, a prognostic Risk score representative of a probability that the colorectal cancer will recur. In some embodiments, at least 11, 12, 13, 14, 15, 16, 17, 18, 19, 20, 21, 22, 23, 24, 25, 26, 27, 28, 29, or 30 genes (or RNA transcripts) from the group can be measured to calculate the prognostic Risk score. In some embodiments, less than 80, 75, 70, 60, 50, 40, 30, 25, 20, or 15 genes (or RNA transcripts) from the group can be measured to calculate the prognostic Risk score. In some embodiments, (about) between 15 and 50, between 15 and 40, between 15 and 30, between 15 and 25, between 15 and 20, genes (or RNA transcripts), or any number of genes or range of numbers of genes therebetween, from the group can be measured to calculate the prognostic Risk score.

In some embodiments, the selected representative genes (or RNA transcripts), or number thereof can be the top genes or number of genes (i.e., the most predictive of cancer recurrence). In certain embodiments, some of the selected representative genes (or RNA transcripts), or number thereof can be among the top genes or number of genes predictive of cancer recurrence, while others of the selected representative genes (or RNA transcripts), or number thereof, can be less predictive of cancer recurrence than other genes (or RNA transcripts) that are not included in the group or set of representative genes (or RNA transcripts). In certain embodiments, the selected representative genes (or RNA transcripts), or number thereof, can be less predictive of cancer recurrence than genes (or RNA transcripts) that are not included in the group or set of representative genes (or RNA transcripts).

In at least one embodiment, scores derived from any 15 of the top 50 prognostic genes (e.g., found in Table 8a) may result in a significantly prognostic score. To select a preferred score: given an integer n, one may compute a level n prognostic score $s_n$ by taking the mean of the n highest ranked gene risk scores. By comparing the significance of $s_n$ for increasing values of n, one may determine that a score using the 25 highest ranked genes is optimal. In at least one embodiment, inclusion of more than 25 genes from the prognostic group of genes may not add further to (or enhance) the prognostic nature of the Risk score calculated therefrom.

Figure 8:
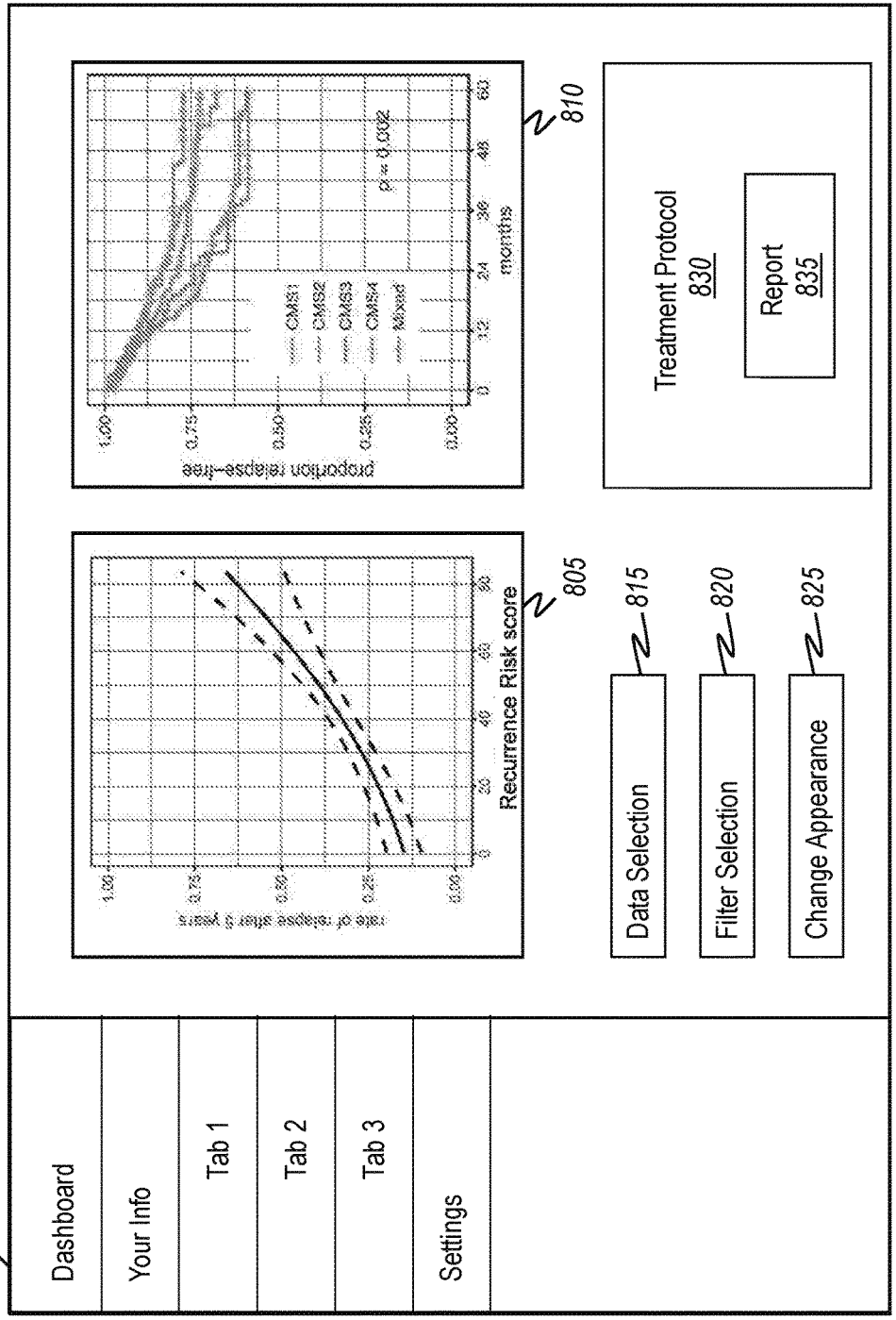
FIG. 8 illustrates a user interface in accordance with an embodiment or aspect of the present disclosure.

By testing multiple thresholds within Risk-training, one may alternatively determine, for example, that a Risk value of 30 is an effective separator of colon tumors into good and poor prognosis subsets, and a threshold of 35 is optimal within stage II colon cancer. Computer systems, storage, software, and related methods FIG. 8 illustrates an example user interface 800 that may be used to visually display any of the information described above. For instance, user interface 800 may display any number of graphs, such as graph 805 and graph 810. Here, graph 805 is representative of the illustration provided in FIG. 2A (e.g., the expected rate of relapse) and graph 810 is representative of the illustration provided in FIG. 3A (e.g., a Kaplan-Meier plot). Of course, any other plots or graphs may be visually presented in user interface 800 as well. Alternatively, or in addition, user interface 800 may display any number of scores, such as one or more CMS scores and/or one or more Risk scores, as described herein. Illustratively, a graph 805 and/or a graph 810 may be or comprise one or more tables, lists, charts, etc., which present or convey data in the user interface 800. In certain embodiments, a graph 805 and/or a graph 810 may present or convey a CMS classification or subtype determination. In some embodiments, CMS score(s) may be presented without a specific diagnosis or CMS determination. However, the CMS score(s) can be representative, informative, and/or determinative with regards to CMS classification, in some embodiments. Similarly, a graph 805 and/or a graph 810 may present or convey a (percent or ratio) probability of cancer recurrence.

User interface 800 also includes an option 815 to select different data on which to display a plot or graph. That is, by selecting option 815, a user can manually change while data he/she is using and working with. As such, user interface 800 is highly configurable and flexibly allows a user to operate with any amount of data. User interface 800 also includes an option 820 to apply one or more filter(s) onto the data. The filters may include any kind of filter. For instance, the data may be filtered by user, by date, by data type (e.g., colorectal cancer data as opposed to other types cancer data), health care provider, primary care physician, and so on. Any other filter may be used as well, where these filters allow a user to refine, or rather to narrow, the focus of the data that is current being viewed and/or manipulated. User interface 800 also includes an option 825 to change the visual appearance of user interface 800. For instance, by selecting option 825, a user can change or otherwise modify the background features of user interface 800 in an effort to customize or tailor user interface 800 in accordance with that user's personal preferences (e.g., language selection, font selection, font size selection, and so on).

User interface 800 also includes a section for visually displaying a treatment protocol 830 that has been developed, in accordance with the principles described above. This treatment protocol 830 may be provided to assist the user in more fully understanding a person's current ailment and how that ailment may be remedied. In some cases, a report 835, which includes the information described earlier, may also be visually displayed within user interface 800. Accordingly, it will be appreciated that user interface 800 may visually present information in accordance with a predefined visual layout. This visual layout may be configured, tailored, or otherwise customized in any manner to improve how the user interacts with the computer system. As such, user interface 800 provides substantial benefits and helps users in understanding the disclosed operations.

Figure 9:
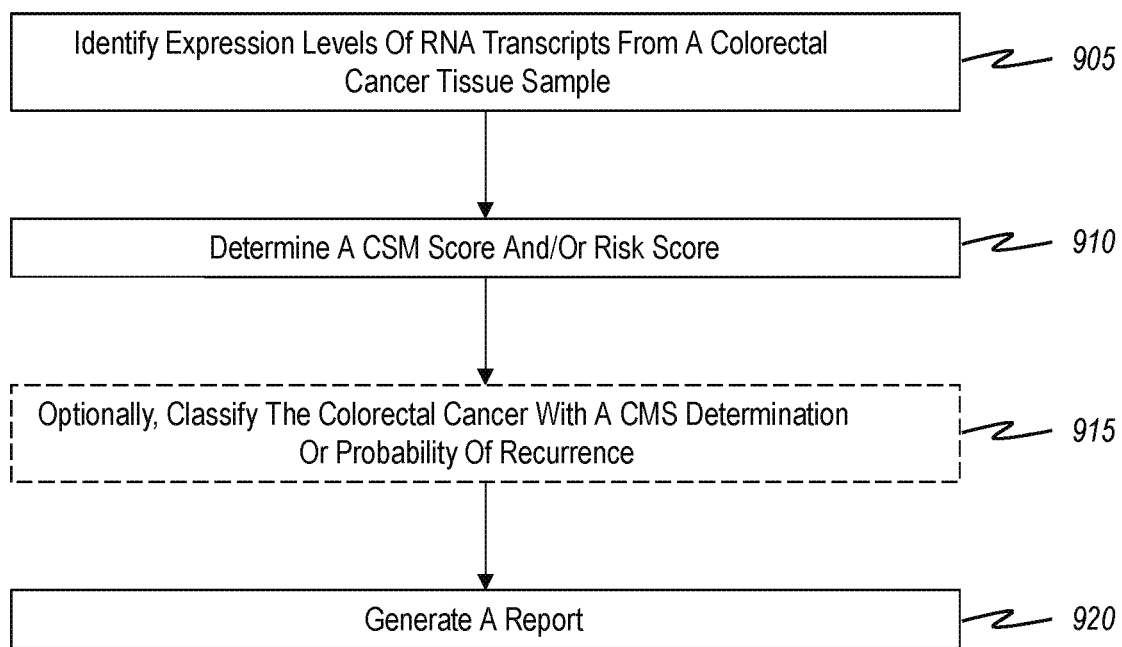
FIG. 9 illustrates a flowchart outlining a method in accordance with an embodiment or aspect of the present disclosure.

FIG. 9 illustrates a flowchart of an example method 900 for visually displaying a treatment protocol for a patient, where the treatment protocol is specific for a particular type of colorectal cancer. It will be appreciated that any of the displayed information may be displayed in the user interface 800 of FIG. 8. Furthermore, it will be appreciated that method 900 may be performed by a computer system, such as the one shown in FIG. 10, which will be discussed later. In some embodiments, one or more acts of method 900 can include multiple sub-acts.

Method 900 initially includes an act 905 of identifying expression levels of RNA transcripts from a colorectal cancer tissue sample. This act may be performed in any of the manners discussed earlier. In some embodiments, for example, act 905 includes identify expression levels of (each of at least twelve) RNA transcripts from a colorectal cancer tissue sample. The colorectal cancer can be of unknown consensus molecular subtype (CMS). The RNA transcripts can comprise at least three RNA transcripts from each of one, two, three, or four groups of genetic elements, each of the groups of genetic elements can define, represent, or correspond to a CMS gene expression profile specific for a different one of CMS1, CMS2, CMS3, and/or CMS4. In some embodiments, the RNA transcripts can be from a group of genetic elements that define, represent, or correspond to a risk of recurrence for the colorectal cancer.

Furthermore, a database or clearinghouse may be provided to store each patient's information. In some cases, the embodiments may obtain information about the sample from the database.

Method 900 also includes act 910 of determining a score. In some embodiments, the score can be a CMS score, as described herein. Act 910 can include, for example, determining, based on the expression level of each of (at least three) RNA transcripts from each of one, two, three, or four groups of genetic elements, a first, second, third, and/or fourth CMS score representative of a probability that the CMS of the colorectal cancer is CMS1, CMS2, CMS3, and/or CMS4, as described herein. In some embodiments, this act first includes determining, based on the expression level of each of the at least three RNA transcripts from a first group of the four groups of genetic elements, a first CMS score representative of a probability that the CMS of the colorectal cancer is CMS1. Then, this act includes determining, based on the expression level of each of the at least three RNA transcripts from a second group of the four groups of genetic elements, a second CMS score representative of a probability that the CMS of the colorectal cancer is CMS2. This act may additionally include determining, based on the expression level of each of the at least three RNA transcripts from a third group of the four groups of genetic elements, a third CMS score representative of a probability that the CMS of the colorectal cancer is CMS3. Finally, this act may include determining, based on the expression level of each of the at least three RNA transcripts from a fourth group of the four groups of genetic elements, a fourth CMS score representative of a probability that the CMS of the colorectal cancer is CMS4. All of the foregoing acts (or sub-acts) as described herein.

In some embodiments, the score can be a recurrence Risk score. Act 910 can include, for example, determining, based on the expression level of (at least fifteen) RNA transcripts, a risk score representative of a probability of recurrence for the colorectal cancer, as described herein.

Method 900 also includes an optional act 915 of classifying the colorectal cancer, as described herein. Act 910 can include, for example, classifying the colorectal cancer with a CMS determination corresponding to a particular CMS and/or based at least in part on the CMS scores (e.g., when one or more of the CMS scores are above a respective predictive threshold), as described herein. Act 910 can include classifying the colorectal cancer with a likelihood, risk, or probability of recurrence, as described herein.

Method 900 is also shown as including act 920 of generating a report. The report can display the CMS scores and/or Risk score, a probability or likelihood related thereto, and/or a determination based at least in part thereon. This report may be displayed as report 835 from FIG. 8. In some embodiments, this act includes generating a report indicating one or more of the first, second, third, and/or fourth CMS scores. In some cases, the report also indicates the probability that the CMS of the colorectal cancer is CMS1, CMS2, CMS3, and/or CMS4. In some cases, (i) one or more of the first, second, third, and/or fourth CMS scores and (ii) the probability that the CMS of the colorectal cancer is CMS1, CMS2, CMS3, and/or CMS4 signifies, at least in part, a treatment protocol specific for the CMS of the colorectal cancer, such as treatment protocol 830 shown in FIG. 8. In some embodiments, the report can display and/or indicate one or more of (i) the probability of recurrence for the colorectal cancer and (ii) a treatment protocol based at least in part on the probability of recurrence for the colorectal cancer. Any of the foregoing as described herein.

Additional and/or alternative method steps and/or acts, as described herein, can be incorporated into method 900.

Accordingly, the disclosed embodiments are able to perform a number of different operations in order to dynamically develop a treatment protocol for a user. This treatment protocol may then be visually displayed on a user interface for the user to view and interact with. For instance, if the treatment protocol requires the user to perform multiple steps, then the user interface can track the progression of the user's progress and provide a progression report. Additionally, the user interface can provide milestones or benchmark goals that the user should try to reach. The user interface can monitor the user's performance in achieving these goals.

In some cases, if the user prematurely ends a session or treatment step, then the user interface can record the user's current status with regard to the treatment protocol and can prompt the user to pick up where he/she previously left off. In this regard, one or more alerts can be provided to the user to alert the user regarding his/her status relative to the treatment protocol.

Attention will now be directed to FIG. 10 which illustrates an example computer system 1000 that may be used to facilitate the disclosed methods. It will be appreciated that computer system 1000 may be configured within various form factors. For example, computer system 1000 may be embodied as a tablet 1000A or a desktop 1000B. The ellipsis 1000C demonstrates that computer system 1000 may be embodied in various other forms too. For instance, computer system 1000 may also be a distributed system that includes one or more connected computing components/devices that are in communication with computer system 1000, a laptop computer, a mobile phone, a server, a data center, and/or any other computer system. The ellipsis 1000C also indicates that other system subcomponents may be included or attached with the computer system 1000, including, for example, sensors that are configured to detect user attributes (e.g., heart rate sensors, tissue sample analyzers, etc.), as well as sensors like cameras and other sensors that are configured to detect user data, all of which sensor data may comprise different types of information used during application of the disclosed embodiments.

In its most basic configuration, computer system 1000 includes various different components. For example, FIG. 10 shows that computer system 1000 includes at least one processor 1005 (aka a "hardware processing unit"), input/output ("I/O") 1010, and storage 1015.

Storage 1015 is shown as including executable code/instructions 1020. Storage 1015 may be physical system memory, which may be volatile, non-volatile, or some combination of the two. The term "memory" may also be used herein to refer to non-volatile mass storage such as physical storage media. If computer system 1000 is distributed, the processing, memory, and/or storage capability may be distributed as well. As used herein, the term "executable module," "executable component," or even "component" can refer to software objects, routines, or methods that may be executed on computer system 1000. The different components, modules, engines, and services described herein may be implemented as objects or processors that execute on computer system 1000 (e.g. as separate threads).

The disclosed embodiments may comprise or utilize a special-purpose or general-purpose computer including computer hardware, such as, for example, one or more processors (such as processor 1005) and system memory (such as storage 1015), as discussed in greater detail below. Embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are physical computer storage media. Computer-readable media that carry computer-executable instructions are transmission media. Thus, by way of example and not limitation, the current embodiments can comprise at least two distinctly different kinds of computer-readable media: computer storage media and transmission media.

Computer storage media are hardware storage devices, such as RAM, ROM, EEPROM, CD-ROM, solid state drives (SSDs) that are based on RAM, Flash memory, phase-change memory (PCM), or other types of memory, or other optical disk storage, magnetic disk storage or other magnetic storage devices, or any other medium that can be used to store desired program code means in the form of computer-executable instructions, data, or data structures and that can be accessed by a general-purpose or special-purpose computer.

Computer system 1000 may also be connected (via a wired or wireless connection) to external sensors (e.g., one or more remote cameras, blood pressure sensors, heart rate monitors, tissue analyzers, etc.). Further, computer system 1000 may also be connected through one or more wired or wireless networks 1025 to remote systems(s) that are configured to perform any of the processing described with regard to computer system 1000.

A graphics rendering engine may also be configured, with processor 1005, to render one or more images within a user interface of computer system 1000 (e.g., user interface 800 from FIG. 8). EO 1010 may include the graphics rendering engine as well as any other hardware or software used to visually display information (e.g., user interface 800). In this regard, I/O 1010 may include monitors, input devices (e.g., a mouse and keyboard), acoustic devices, and so on.

A "network," like the network 1025 shown in FIG. 10, is defined as one or more data links and/or data switches that enable the transport of electronic data between computer systems, modules, and/or other electronic devices. When information is transferred, or provided, over a network (either hardwired, wireless, or a combination of hardwired and wireless) to a computer, the computer properly views the connection as a transmission medium. Computer system 1000 will include one or more communication channels that are used to communicate with the network 1025. Transmissions media include a network that can be used to carry data or desired program code means in the form of computer-executable instructions or in the form of data structures. Further, these computer-executable instructions can be accessed by a general-purpose or special-purpose computer. Combinations of the above should also be included within the scope of computer-readable media.

Upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a network interface card or "NIC") and then eventually transferred to computer system RAM and/or to less volatile computer storage media at a computer system. Thus, it should be understood that computer storage media can be included in computer system components that also (or even primarily) utilize transmission media.

Computer-executable (or computer-interpretable) instructions comprise, for example, instructions that cause a general-purpose computer, special-purpose computer, or special-purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The embodiments may also be practiced in distributed 3o system environments where local and remote computer systems that are linked (either by hardwired data links, wireless data links, or by a combination of hardwired and wireless data links) through a network each perform tasks (e.g. cloud computing, cloud services and the like). In a distributed system environment, program modules may be located in both local and remote memory storage devices.

Additionally, or alternatively, the functionality described herein can be performed, at least in part, by one or more hardware logic components (e.g., the processor 1005). For example, and without limitation, illustrative types of hardware logic components that can be used include Field-Programmable Gate Arrays (FPGAs), Program-Specific or Application-Specific Integrated Circuits (ASICs), Program-Specific Standard Products (ASSPs), System-On-A-Chip Systems (SOCs), Complex Programmable Logic Devices (CPLDs), Central Processing Units (CPUs), and other types of programmable hardware.

It will be appreciated that computer system 1000 may include one or more processors (e.g., processor(s) 1005) and one or more computer-readable hardware storage devices (e.g., storage 1015), where the storage devices include computer-executable instructions that are executable by the one or more processors to perform any method (e.g., method 900 presented in FIG. 9). In this regard, computer system 1000 is also highly flexible and can perform numerous operations.

RNA Quantification

Briefly, gene expression levels (or RNA expression levels, or RNA transcript levels, etc.) can be measured as known in the art. For instance, in some embodiments, RNA sequencing (RNA-Seq), including high throughput sequencing, can be used to determine which genes (or RNA transcripts) are expressed and quantify (or quantitate) the expression levels of these genes (or RNA transcripts).

Illustratively, (total) RNA for each sample can be converted into a sequencing library of template molecules for sequencing. Library preparation, as known in the art, on an Illumina Cluster Station and Genome Analyzer according to the protocol for the Illumina mRNA Sample preparation kit (Part #1004898, Rev A: Illumina, San Diego, Calif.). It will be appreciated, however, that other platforms, systems, apparatus, and protocols are known in the art and contemplated herein. Briefly, RNA (e.g., poly-A mRNA) can be purified or isolated from other components (e.g., from total RNA (2 µg) using poly-T oligo-attached magnetic beads). The mRNA can then be fragmented, and the first strand of cDNA can be synthesized from the cleaved RNA fragments using reverse transcriptase and (random) primers. Following the synthesis of the second strand of cDNA (to form double stranded DNA representing the RNA transcripts), end repair can (optionally) be performed on overhangs using T4 DNA polymerase and Klenow DNA polymerase, followed by ligation of sequencing Adapters to the ends of the DNA fragments.

The cDNA fragments can be purified using a gel run (e.g., at 80 V for approximately 3 hours until the Orange G dye band reached the bottom of the gel). The gel can be stained with SYBR green to visualize the DNA band. Illustratively, a band (e.g., at 350-450 bp) can be excised vertically from the gel, which can then be dissolved at room temperature using a QIAquick Gel Extraction Kit (Qiagen, Valencia, Calif.). The purified cDNA templates can be enriched (e.g., for 15 cycles of PCR amplification) and validated (e.g., using a BioAnalyzer) to assess size, purity and concentration of the purified cDNA libraries. The cDNA libraries can then be processed for single end cluster generation (e.g., by being placed on an Illumina Cluster Station, according to the protocol outlined in the Illumina Genome Analysis User Guide (Part #11251649, RevA)).

The template cDNA libraries (1.5 µg) can then be hybridized to a plate, chip, or array grid (e.g., a flow cell), amplified and linearized and denatured to create a flow cell with ssDNA ready for sequencing. Each flow cell can then be sequenced (e.g., on an Illumina GAIIX Genome Analyzer). Illustratively, each sample can undergo a single lane of sequencing (e.g., using single end sequencing for 76 cycles according to the protocol outlined in the Illumina Genome Analysis User Guide (Part #11251649, RevA)). After completion of the (76 cycle) sequencing run, quality control on reads can optionally be performed, and the raw sequence data can enter the CMS classifier or Risk classifier workflow described herein.

Alternatively, RT-PCR may be used to measure, collect, and/or quantify gene expression levels, as understood by those skilled in the art and/or described herein. Illustratively, the quantification of mRNA using RT-PCR can be achieved as either a one-step or a two-step reaction. The difference between the two approaches lies in the number of tubes used when performing the procedure. In the one-step approach, the entire reaction from cDNA synthesis to PCR amplification occurs in a single tube. On the other hand, the two-step reaction requires that the reverse transcriptase reaction and PCR amplification be performed in separate tubes.

In some embodiments, microarray expression profiling may also be used to measure, collect, and/or quantify gene expression levels, as understood by those skilled in the art and/or described herein. Illustratively, 2 ug of total RNA of sample and Stratagene Universal Human Reference can be amplified and labeled using Agilent's Low RNA Input Linear Amplification Kit. Sample and reference can be co-hybridized on a Custom Agilent 244K Gene Expression Microarray. The expression data can be Lowess normalized and the ratio of the Cy5 channel (sample) and Cy3 channel (reference) can be log 2 transformed to create gene expression values for 23,199 probesets. Probesets without gene annotations and genes with missing data in ≥20% of the samples can be removed, with remaining genes available for further analysis. Missing values in the remaining genes can be imputed with the mean value across all samples.

Compositions

Some embodiments can comprise a composition. The composition can comprise a mixture of cDNA molecules corresponding to (at least twelve or at least fifteen) RNA transcripts, as described herein. The (at least twelve) RNA transcripts can comprise (at least three) RNA transcripts from (each of two, three, or four) groups of genetic elements. Each of the (two, three, or four) groups of genetic elements can define, represent, or correspond to a CMS gene expression profile specific for a different one of CMS1, CMS2, CMS3, and CMS4, as described herein. The (at least fifteen) RNA transcripts can be from a group of genetic elements that define, represent, or correspond to a risk of recurrence for a colorectal cancer, as described herein.

Cancer Treatments

Various cancer treatments or treatment protocols, including surgical removal of cancer, tumor(s), and/or tissue, chemotherapy, antibody/immunotherapy, radiation therapy, observation, etc. are known in the art and contemplated herein. In some cases, one or more (particular) treatment(s) or treatment protocol(s) can be or are known to be more effective than others, based at least in part on the type, stage, grade, CMS, risk of recurrence, or other characteristic or feature of the cancer. Commonly used chemotherapy drugs for colon cancer include leucovorin, fluorouracil, irinotecan, oxaliplatin, capecitabine, trifluridine, andtipiracil. Those skilled in the art will appreciate and understand which drug(s) are best suited to treat which cancers with which characteristic(s) or feature(s). The NCCN guidelines (2018) also gives guidance as to when to use 5-FU, FOLFOX, CAPEOX, cetuximab, panitumumab, vemurafenib, pembrolizumab, bevacizumab, nivolumab, and regorafenib for colon cancer.

Some patients (e.g., with advanced colon cancer) may benefit from immunotherapy with antibodies such as pembrolizumab (Keytruda), nivolumab (Opdivo), cetuximab, and so forth. External beam radiation therapy (EBRT) is also used to target certain cancer(s), tumor(s), or tissue(s).

Healthcare providers and patients empowered with the results, outcomes, information, recommendations, and diagnosis generated through or with embodiments of the present disclosure can make better and/or more-informed decisions with regards to treatments and treatment protocols. Indeed, certain embodiments can include determining and/or administering a treatment protocol based at least in part on the results, outcomes, information, recommendations, and diagnosis generated through or with embodiments of the present disclosure.

CONCLUSION

Existing systems and methods for determining the consensus molecular subtype (CMS) of a colorectal cancer tumor and/or or an appropriate treatment protocol based on the CMS of a colorectal cancer tumor may be prohibitively expensive, time consuming, and/or technically challenging normal clinical application and/or cancer patients with limited financial means. Embodiments of the present disclosure provide systems and methods for determining the CMS of a colorectal cancer tumor and/or or an appropriate treatment protocol based on the CMS of a colorectal cancer tumor based on the positive predictive value (PPV) of an abbreviated gene expression profile. Specifically, While the present disclosure makes reference to specific exemplary embodiments, the present disclosure may also be embodied or implemented in other specific forms without departing from its spirit or essential characteristics. Accordingly, the disclosed embodiments are to be considered in all respects only as illustrative and not restrictive. For instance, various substitutions, alterations, and/or modifications of the inventive features described and/or illustrated herein, and additional applications of the principles described and/or illustrated herein, which would occur to one skilled in the relevant art and having possession of this disclosure, can be made to the described and/or illustrated embodiments without departing from the spirit and scope of the disclosure. Such substitutions, alterations, and/or modifications are to be considered within the scope of this disclosure.

The scope of the invention is indicated by the appended claims rather than by the foregoing description of the present disclosure. The limitations recited in the claims are to be interpreted broadly based on the language employed in the claims and not limited to specific examples described in the present disclosure, including the detailed description, which examples are to be construed as non-exclusive and non-exhaustive. All changes which come within the meaning and range of equivalency of the claims are to be embraced within their scope.

It will also be appreciated that various features of certain embodiments can be compatible with, combined with, included in, and/or incorporated into other embodiments of the present disclosure. For instance, systems, methods, and/or products according to certain embodiments of the present disclosure may include, incorporate, or otherwise comprise features described in other embodiments disclosed and/or described herein. Thus, disclosure of certain features relative to a specific embodiment of the present disclosure should not be construed as limiting application or inclusion of said features to the specific embodiment.

In addition, unless a feature is described as being required in a particular embodiment, features described in the various embodiments can be optional and may not be included in other embodiments of the present disclosure. Moreover, unless a feature is described as requiring another feature in combination therewith, any feature herein may be combined with any other feature of a same or different embodiment disclosed herein. It will be appreciated that while features may be optional in certain embodiments, when features are included in such embodiments, they can be required to have a specific configuration as described in the present disclosure.

Likewise, any steps recited in any method or process described herein and/or recited in the claims can be executed in any suitable order and are not necessarily limited to the order described and/or recited, unless otherwise stated (explicitly or implicitly). Such steps can, however, also be required to be performed in a specific order or any suitable order in certain embodiments of the present disclosure.

Furthermore, various well-known aspects of illustrative systems, methods, products, and the like are not described herein in particular detail in order to avoid obscuring aspects of the example embodiments. Such aspects are, however, also contemplated herein.

What is claimed is:

1. A method of accurately determining a consensus molecular subtype (CMS) of a colorectal cancer from a tissue sample of a patient, the method comprising:

obtaining a gene expression profile from the tissue sample and determining a CMS probability score for a CMS1, CMS2, CMS3, CMS4 or mixed CMS for the patient, wherein each CMS has a CMS genetic profile of gene expression, wherein the CMS1 genetic profile comprises expression of three or more genes selected from the group consisting of: ENTREZ IDs 6148 (SET), 9219 (MTA2), 10855 (HPSE), 3191 (HNRNPL), 9037 (SEMA5A), 10079 (ATP9A), 83737 (ITCH), 10140 (TOB1), 8313 (AXIN2), 54891 (INO80D), 57798 (GATAD1), 998 (CDC42), 7105 (TSPAN6), 23475 (QPRT), 6431 (SRSF6), 3725 (JUN), 81786 (TRIM7), 9554 (SEC22B), 1602 (DACH1), 57168 (ASPHD2), 401474 (SAMD12), 139322 (APOOL), 1783 (DYNC1L12), 29966 (STRN3), 80183 (RUBCNL), 8019 (BRD3), 3549 (IHH), 27330 (RPS6KA6), and 10451 (VAV3);

wherein the CMS2 genetic profile comprises expression of three or more genes selected from the group consisting of: ENTREZ IDs 5326 (PLAGL2), 112858 (TP53RK), 1057 (CELP), 6780 (STAU1), 23509 (POFUT1), 51497 (NELFCD), 430 (ASCL2), 171023 (ASXL1), 25980 (AAR2), 23475 (QPRT), 22919 (MAPRE1), 80183 (RUBCNL), 51526 (OSER1), 28951 (TRIB2), 1056 (CEL), 1846 (DUSP4), 644 (BLVRA), 9054 (NFS1), (DDX27), 54894 (RNF43), 58490 (RPRD1B), and 4212 (MEIS2);

wherein the CMS3 genetic profile comprises expression of three or more genes selected from the group consisting of: ENTREZ IDs 4217 (MAP3K5), 84666 (RETNLB), 8857 (FCGBP), 7078 (TIMP3), 80150 (ASRGL1), 4151 (MB), 54596 (L1TD1), 143458 (LDLRAD3), 84189 (SLITRK6), 7410 (VAV2), 5937 (RBMS1), 25837 (RAB26), 10753 (CAPN9), 192134 (B3GNT6), 201501 (ZBTB7C), 9509 (ADAMTS2), 140828 (LINC00261), 84624 (FNDC1), 1290 (COL5A2), 405753 (DUOXA2), 1278 (COL1A2), 2335 (FN1), 1295 (COL8A1), 3488 (IGFBP5), 9254 (CACNA2D2), and 155465 (AGR3);

wherein the CMS4 genetic profile comprises expression of three or more genes selected from the group consisting of: ENTREZ IDs 23414 (ZFPM2), 30008 (EFEMP2), 27295 (PDLIM3), 2737 (GLI3), 143903 (LAYN), 154810 (AMOTL1), 11037 (STON1), 7145 (TNS1), 9590 (AKAP12), 5178 (PEG3), 23194 (FBXL7), 4256 (MGP), 10000 (AKT3), 1410 (CRYAB), 862 (RUNX1T1), 4286 (MITF), 83871 (RAB34), 4211 (MEIS1), 165 (AEBP1), 6695 (SPOCK1), 1292 (COL6A2), 9353 (SLIT2), 4131 (MAP1B), 8639 (AOC3), 5549 (PRELP), 54796 (BNC2), 147906 (DACT3), and 8828 (NRP2);

determining, based on the expression levels of genes for each of the CMS genetic profiles, a probability score for CMS1, CMS2, CMS3, and CMS4; and generating a report to provide a treatment plan for the patient that is specific for the CMS1, CMS2, CMS3 and CMS4 determined to have the highest probability score; and administering a treatment protocol to the patient, wherein the treatment protocol is consistent with the treatment plan for the specific CMS1, CMS2, CMS3 and CMS4 having the highest probability score.

2. The method of claim 1, wherein the report is visually displayed on a graphical user interface, the report being generated by a computer system coupled to the graphical user interface, the computer system comprising:

one or more processor(s); and one or more computer-readable hardware storage devices having stored thereon computer-executable instructions that are executable by the one or more processor(s) to cause the computer system to visually display the report.

3. The method of claim 1, wherein determining a respective CMS probability score comprises:

matching the expression level of each gene or RNA transcript with a reference expression level of said gene or RNA transcript in a reference data set, each reference expression level corresponding to a scaled value representing the probability that the CMS of a patient is CMS1, CMS2, CMS3, or CMS4, to provide a scaled value; and calculating the respective CMS scores based on the respective scaled values for each of the genes or RNA transcripts.

4. The method of claim 3, wherein the reference data set comprises a curve fit of a population of expression levels of the respective gene or RNA transcript, the curve fit reflecting the probability that the CMS of a patient CMS1, CMS2, CMS3, or CMS4.

5. The method of claim 3, wherein calculating the respective CMS scores comprises calculating a mean of the respective scaled values for each of the gene expression levels or RNA transcripts.

6. The method of claim 5, wherein calculating the respective CMS scores comprises:

producing a first CMS pre-score that informs membership in CMS1 by ranking risk scores of genes by level of significance in predicting membership in CMS1 in the CMS1 reference data set; and selecting at least three of the genes corresponding to at least three of the highest rank genes in the CMS1 reference data set that are also among the highest ranked genes in a second CMS1 reference data set;

wherein calculating the second CMS score further comprises:

producing a second CMS pre-score that informs membership in CMS2 by ranking risk scores of genes by level of significance in predicting membership in CMS2 in the CMS2 reference data set; and selecting at least three of the genes corresponding to at least three of the highest rank genes in the CMS2 reference data set that are also among the highest ranked genes in a second CMS2 reference data set;

wherein calculating the third CMS score further comprises:

producing a third CMS pre-score that informs membership in CMS3 by ranking risk scores of genes by level of significance in predicting membership in CMS3 in the CMS3 reference data set; and selecting at least three of the genes corresponding to at least three of the highest rank genes in the CMS3 reference data set that are also among the highest ranked genes in a second CMS3 reference data set;

wherein calculating the fourth CMS score further comprises:

producing a fourth CMS pre-score that informs membership in CMS4 by ranking risk scores of genes by level of significance in predicting membership in CMS4 in the CMS4 reference data set; and selecting at least three of the genes corresponding to at least three of the highest rank genes in the CMS4 reference data set that are also among the highest ranked genes in a second CMS4 reference data set.

7. The method of claim 1, wherein the treatment protocol specific for the colorectal cancer subtype is determined by stage of the cancer, grade of the cancer, metastatic state of the cancer, and presence or absence of one or more genetic mutations of the patient tissue sample.

8. The method of claim 7, wherein each step of obtaining an expression level of the genes or RNA transcripts comprises:

extracting RNA transcripts from a colorectal cancer tissue sample from the patient; and quantifying the expression level of the genes or RNA transcripts.

9. The method of claim 8, wherein the colorectal cancer tissue sample is a formalin-fixed paraffin-embedded (FFPE) colorectal cancer tissue sample and wherein extracting RNA transcripts from the colorectal cancer tissue sample comprises extracting RNA transcripts from the formalin-fixed paraffin-embedded (FFPE) colorectal cancer tissue sample.

10. The method of claim 1, wherein each CMS score comprises a number having a scaled value between 0 and 1 or between 0 and 100, or an equivalent thereof.

11. The method of claim 1, wherein the report further indicates one or more of:

the CMS determination of the colorectal cancer; and a treatment protocol that is consistent with the CMS determination.

12. The method of claim 1, wherein:

the CMS1 genetic profile of gene expression comprises gene expression levels of three or more genes selected from the group consisting of ENTREZ IDs 9219 (MTA2), 57168 (ASPHD2), 7105 (TSPAN6), 23475 (QPRT), and 998 (CDC42);

the CMS2 genetic profile of gene expression comprises gene expression levels of three or more genes selected from the group consisting of ENTREZ IDs 112858 (TP53RK), 5326 (PLAGL2), 23509 (POFUT1), 6780 (STAU1), and 1846 (DUSP4);

the CMS3 genetic profile of gene expression comprises gene expression levels of three or more genes selected from the group consisting of ENTREZ IDs 7078 (TIMP3), 80150 (ASRGL1), 84189 (SLITRK6), 84666 (RETNLB), and 5937 (RBMS1); and the CMS4 genetic profile of gene expression comprises gene expression of three or more genes selected from the group consisting of ENTREZ IDs 143903 (LAYN), 23414 (ZFPM2), 11037 (STON1), 27295 (PDLIM3), and 165 (AEBP1).

13. A method of classifying a human colorectal cancer tumor into a consensus molecular subtype (CMS) from a CMS probability score report prepared from an abbreviated gene expression profile of the tumor, the method comprising:

obtaining an expression level of at least three RNA transcripts from a colorectal cancer tissue sample of the tumor, the at least three RNA transcripts being specific for a first group of genes that define a first CMS profile for CMS1, CMS2, CMS3, or CMS4;

determining, based on the expression level of each of the RNA transcripts from the first group of genes, a first CMS probability score that the CMS of the colorectal cancer tumor corresponds with the first CMS profile;

classifying the colorectal cancer tumor as having the first CMS profile where the first CMS probability score is above a predictive threshold; and administering a treatment protocol that is consistent with a treatment plan for the CMS of the tumor classified as having the first CMS profile.

14. The method of claim 13 further comprising:

obtaining an expression level of at least three RNA transcripts for genes selected from a second group of genes to determine a second CMS profile for CMS1, CMS2, CMS3, or CMS4, the second CMS profile being different from the first CMS profile; and determining, based on the expression level of each of the at least three RNA transcripts for the second group of genes, a second CMS score representative of a probability that the CMS of the colorectal cancer corresponds with the CMS of the second CMS profile.

15. The method of claim 14, wherein the step of classifying the colorectal cancer with a CMS determination corresponding to the CMS of the first CMS profile is determined in reference to the second CMS score.

16. The method of claim 13 further comprising generating a treatment protocol based at least in part on the CMS determination.

17. The method of claim 13, wherein determining a CMS score comprises:

matching the expression level of each RNA transcript with a reference expression level of said RNA transcript in a respective reference data set, each reference expression level corresponding to a scaled value representing the probability that the CMS of a colorectal cancer expressing said RNA transcript at said reference expression level is CMS1, CMS2, CMS3, or CMS4; and calculating the CMS score based on the respective scaled values for each of the RNA transcripts.

18. The method of claim 13, wherein the first group of genes comprises a panel of genes expressed in a population of tissue samples of colorectal cancers determined to be CMS1, CMS2, CMS3, or CMS4.

* * * * *

UNITED STATES PATENT AND TRADEMARK OFFICE
CERTIFICATE OF CORRECTION

PATENT NO. : 11,198,911 B2
APPLICATION NO. : 16/978903
DATED : December 14, 2021
INVENTOR(S) : Buechler Page 1 of 1

It is certified that error appears in the above-identified patent and that said Letters Patent is hereby corrected as shown below:

In the Specification

In Column 2, please delete at Line 20:
"stage II or stage II colon", and substitute therefore --stage II or stage III colon--

In Column 2, please delete at Line 26:
"Some stage H colon cancer", and substitute therefore --Some stage II colon cancer--

Signed and Sealed this
Nineteenth Day of April, 2022

Katherine Kelly Vidal
*Director of the United States Patent and Trademark Office*